US009748496B2

(12) United States Patent
Mizutani et al.

(10) Patent No.: US 9,748,496 B2
(45) Date of Patent: Aug. 29, 2017

(54) NITROGENATED HETEROCYCLIC DERIVATIVE, ELECTRON-TRANSPORTING MATERIAL FOR ORGANIC ELECTROLUMINESCENT ELEMENTS, AND ORGANIC ELECTROLUMINESCENT ELEMENT USING SAME

(75) Inventors: Sayaka Mizutani, Ibaraki (JP); Takayasu Sado, Chiba (JP); Hiroki Ishida, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 791 days.

(21) Appl. No.: 13/982,879

(22) PCT Filed: Feb. 1, 2012

(86) PCT No.: PCT/JP2012/052319
§ 371 (c)(1),
(2), (4) Date: Jul. 31, 2013

(87) PCT Pub. No.: WO2012/105629
PCT Pub. Date: Aug. 9, 2012

(65) Prior Publication Data
US 2013/0306955 A1 Nov. 21, 2013

(30) Foreign Application Priority Data
Feb. 2, 2011 (JP) ................. 2011-021240

(51) Int. Cl.
| | | |
|---|---|---|
| H01L 51/54 | (2006.01) |
| C09K 11/06 | (2006.01) |
| H01L 51/00 | (2006.01) |
| C07D 235/18 | (2006.01) |
| C07D 235/26 | (2006.01) |
| C07D 239/36 | (2006.01) |
| C07D 403/10 | (2006.01) |
| C07D 403/14 | (2006.01) |
| C07D 471/04 | (2006.01) |
| C07D 487/04 | (2006.01) |
| C07D 513/04 | (2006.01) |
| C07D 401/04 | (2006.01) |
| C07D 235/02 | (2006.01) |
| C07D 401/10 | (2006.01) |
| C07D 403/04 | (2006.01) |
| C07D 405/10 | (2006.01) |
| C07D 239/70 | (2006.01) |
| C07D 417/04 | (2006.01) |
| C07D 473/28 | (2006.01) |
| C07D 487/06 | (2006.01) |
| C07D 493/04 | (2006.01) |
| C07F 5/02 | (2006.01) |
| H01L 51/50 | (2006.01) |

(52) U.S. Cl.
CPC ........ *H01L 51/0072* (2013.01); *C07D 235/02* (2013.01); *C07D 235/18* (2013.01); *C07D 235/26* (2013.01); *C07D 239/36* (2013.01); *C07D 239/70* (2013.01); *C07D 401/04* (2013.01); *C07D 401/10* (2013.01); *C07D 403/04* (2013.01); *C07D 403/10* (2013.01); *C07D 403/14* (2013.01); *C07D 405/10* (2013.01); *C07D 417/04* (2013.01); *C07D 471/04* (2013.01); *C07D 473/28* (2013.01); *C07D 487/04* (2013.01); *C07D 487/06* (2013.01); *C07D 493/04* (2013.01); *C07D 513/04* (2013.01); *C07F 5/02* (2013.01); *C07F 5/025* (2013.01); *H01L 51/0052* (2013.01); *H01L 51/0053* (2013.01); *H01L 51/0054* (2013.01); *H01L 51/0067* (2013.01); *H01L 51/0073* (2013.01); *H01L 51/5072* (2013.01); *H01L 51/5076* (2013.01)

(58) Field of Classification Search
None
See application file for complete search history.

(56) References Cited

U.S. PATENT DOCUMENTS

| | | | |
|---|---|---|---|
| 5,645,948 A | 7/1997 | Shi et al. | |
| 2007/0069638 A1* | 3/2007 | Matsuura | C09K 11/06 313/504 |

(Continued)

FOREIGN PATENT DOCUMENTS

| | | | |
|---|---|---|---|
| JP | 04320485 A | * | 11/1992 |
| JP | 10-246973 A | | 9/1998 |
| JP | 11-345687 A | | 12/1999 |
| JP | 2002-38141 A | | 2/2002 |
| JP | 2004-146368 A | | 5/2004 |
| JP | 2005-72012 A | | 3/2005 |
| JP | 2006-176448 A | | 7/2006 |
| JP | 2008-164776 A | | 7/2008 |
| JP | 2010-10576 A | | 1/2010 |
| WO | WO 2007/063760 A1 | | 6/2007 |
| WO | WO 2010/136401 A2 | | 12/2010 |

OTHER PUBLICATIONS

Machine translation of JP04-320485. Date of publication: Nov. 11, 1992.*

(Continued)

*Primary Examiner* — Andrew K Bohaty
(74) *Attorney, Agent, or Firm* — Oblon, McClelland, Maier & Neustadt, L.L.P.

(57) ABSTRACT

A specific nitrogen-containing heterocyclic compound having a urea structure, an electron transporting material containing the nitrogen-containing heterocyclic compound, and an organic electroluminescence device including a light emitting layer and an electron transporting layer between a cathode and an anode in which the electron transporting layer includes the electron transporting material or the nitrogen-containing heterocyclic derivative. An organic EL device exhibiting high emission efficiency even at low voltage and a material for organic EL devices are described.

33 Claims, No Drawings

(56) References Cited

U.S. PATENT DOCUMENTS

| | | | |
|---|---|---|---|
| 2008/0111473 A1 | 5/2008 | Kawamura et al. | |
| 2009/0284134 A1 | 11/2009 | Iida et al. | |
| 2010/0149471 A1* | 6/2010 | Palto .................. | G02F 1/134363 349/117 |

OTHER PUBLICATIONS

Jeffrey T. Kuethe, et al., "Synthesis of Disubstituted Imidazol [4,5-b] pyridin-2-ones", Journal of Organic Chemistry 2004, vol. 69, Table 2, Jul. 1, 2004, pp. 7752-7754.

J.S. Yadav, et al., "NbCl5-catalyzed Rapid and Efficient Synthesis of 3,4-Dihydropyrimidinones Under Ambient Conditions", Chemistry Letters, vol. 33, No. 7, Scheme 1., Table 1, Mar. 18, 2004, pp. 926-927 (with cover pages).

Kevin Lewandowski, et al., "A Combinatorial Approach to Recognition of Chirality: Preparation of Highly Enantioselective Aryl-Dihydropyrimidine Selectors for Chiral HPLC", Journal of Combinatorial Chemistry, vol. 1, No. 1, Figure 1., Figure 3, Sep. 8, 1998, pp. 105-112.

Handbook of Chemistry (Pure Chemistry II, 1984, p. 493, edited by The Chemical Society of Japan ).

International Search Report issued Apr. 17, 2012 in PCT/JP2012/052319.

* cited by examiner

NITROGENATED HETEROCYCLIC DERIVATIVE, ELECTRON-TRANSPORTING MATERIAL FOR ORGANIC ELECTROLUMINESCENT ELEMENTS, AND ORGANIC ELECTROLUMINESCENT ELEMENT USING SAME

TECHNICAL FIELD

The present invention relates to nitrogen-containing heterocyclic derivatives, electron transporting materials for organic electroluminescence devices, and organic electroluminescence devices employing the electron transporting materials.

BACKGROUND ART

Organic electroluminescence (EL) devices utilizing organic substances are much expected to be useful as inexpensive, large-sized full color display devices of solid state emission type and many developments have been made thereon. An organic EL device is generally constructed from a light emitting layer and a pair of opposite electrodes sandwiching the light emitting layer. When an electric field is applied between the electrodes, electrons are injected from a cathode and holes are injected from an anode. The injected electrons recombine with the injected holes in the light emitting layer to form excited states. When the excited states return to the ground state, the energy is released as light.

As compared with inorganic light emitting diodes, conventional organic EL devices require high driving voltage, exhibit low emission efficiency, and cause significant deterioration in their properties. Therefore, the organic EL device has not yet been put into practical use. Recently, although the properties of organic EL device have been improved gradually, a higher emission efficiency at a lower driving voltage is still required.

To meet such requirement, Patent Document 1 discloses a device which includes a compound having a benzimidazole structure as a light emitting material. It is reported that the device emits at a luminance of 200 cd/m$^2$ under a voltage of 9 V. Patent Document 2 describes a compound having a benzimidazole ring and an anthracene skeleton. Patent Document 3 describes a compound having an imidazole ring, which is used in the light emitting layer and the hole blocking layer. However, it has been still required to develop an organic EL device which can be driven at lower voltage and exhibits a higher emission efficiency as compared with organic EL devices employing the compounds proposed in the patent documents.

PRIOR ART DOCUMENTS

Patent Documents

Patent Document 1: U.S. Pat. No. 5,645,948
Patent Document 2: JP 2002-38141A
Patent Document 3: JP 2004-146368A

SUMMARY OF THE INVENTION

Problems to be Solved by the Invention

The present invention has been made to solve the above problems. An object of the invention is to provide a novel nitrogen-containing heterocyclic derivative which is useful for use in organic EL devices. Another object of the invention is to realize an organic EL device exhibiting a high emission efficiency even when driving the device at low voltage, while using the nitrogen-containing heterocyclic derivative in at least one layer of the organic thin film layer.

Means for Solving the Problems

As a result of extensive research for achieving the above object, the inventors have found that the oxygen of urea structures is negatively polarized by a mesomeric effect and this negative polarization increases the affinity with metals to improve the electron injection from metals. It has been further found that the driving voltage is reduced while increasing the efficiency by using a nitrogen-containing heterocyclic derivative including an urea structure substituted with an aryl group or a heterocyclic group in at least one layer of the organic thin film layer of organic EL devices. The present invention is based on these findings.

Regardless of the fact that only the use as a host material or a hole transporting material has been reported about the compounds having an urea structure, the new use as an electron transporting material has been found by the inventors.

The present invention, wherein the definition of hydrogen atom includes a heavy hydrogen atom, provides:
1. An electron transporting material represented by formula (1):

$$A_1(\text{-}L_1\text{-}L_2\text{-}L_3\text{-}L_4\text{-}Ar_1)_m \qquad (1)$$

wherein:
each of $L_1$, $L_2$, $L_3$, and $L_4$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$Ar_1$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms;

$A_1$ represents an m-valent residue of a ring-containing compound represented by formula (2); and m represents an integer of 1 or more:

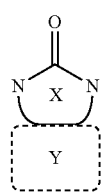

(2)

wherein:
ring X is a substituted or unsubstituted, saturated or unsaturated 5- to 8-membered ring having a ring nitrogen atom and a ring carbon atom;
the ring X may be fused to one or more rings Y; and
the ring Y represents a substituted or unsubstituted hydrocarbon ring or a substituted or unsubstituted heteroring;

2. An electron transporting material represented by formula (1-1):

$$A_{11}(-L_{11}-L_{21}-L_{31}-L_{41}-Ar_{11})_p \quad (1\text{-}1)$$

wherein:
each of $L_{11}$, $L_{21}$, $L_{31}$, and $L_{41}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$Ar_{11}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms;

$A_{11}$ represents a p-valent residue of a ring-containing compound represented by formula (2-1); and p represents an integer of 1 or more:

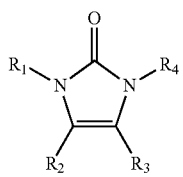

(2-1)

wherein;
each of $R_1$ to $R_4$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, a boryl group, a phosphino group, an amino group, a halogen atom, a cyano group, a nitro group, a hydroxyl group, a carboxyl group, or a valence bonded to $L_{11}$; or a pair of $R_1$ and $R_2$, $R_2$ and $R_3$, or $R_3$ and $R_4$ are bonded to each other to form a ring Y represented by a substituted or unsubstituted hydrocarbon ring or a substituted or unsubstituted heteroring;

3. The electron transporting material according to item 2, wherein $A_{11}$ represents a p-valent residue of a ring-containing compound represented by formula (2-1-1), (2-1-2), or (2-1-3):

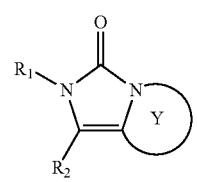

(2-1-1)

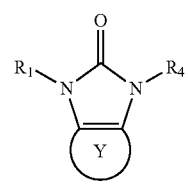

(2-1-2)

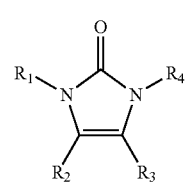

(2-1-3)

wherein:
each of $R_1$ to $R_4$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, a boryl group, a phosphino group, an amino group, a halogen atom, a cyano group, a nitro group, a hydroxyl group, a carboxyl group, or a valence bonded to $L_{11}$; and Y represents the ring Y;

4. The electron transporting material according to item 2 or 3, wherein $A_{11}$ represents a p-valent residue of a compound represented by formula (2-1-2-1);

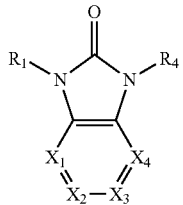

(2-1-2-1)

wherein:

each of $X_1$ to $X_4$ independently represents $CR_5$ or N;

each of $R_1$, $R_4$, and $R_5$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{11}$; or $R_1$, $R_4$, and $R_5$ are each bonded to each other to form a ring which forms a part of the ring Y;

5. The electron transporting material according to any one of items 2 to 4, wherein the electron transporting material is represented by formula (1-1-1):

$$Ar_{11a}\text{-}L_{41a}\text{-}L_{31a}\text{-}L_{21a}\text{-}L_{11a}\text{-}A_{11}\text{-}L_{11b}\text{-}L_{21b}\text{-}L_{41b}\text{-}L_{41b}\text{-}Ar_{11b} \quad (1\text{-}1\text{-}1)$$

wherein:

each of $L_{11a}$, $L_{21a}$, $L_{31a}$, $L_{41a}$, $L_{11b}$, $L_{21b}$, $L_{31b}$, and $L_{41b}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$A_{11}$ represents a divalent residue of a compound represented by formula (2-1), (2-1-1), (2-1-2), (2-1-3), or (2-1-2-1);

$Ar_{11a}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms; and $Ar_{11b}$ represents a substituted or unsubstituted aryl group having 12 to 30 ring carbon atoms or a substituted or unsubstituted heteroaryl group having 12 to 30 ring atoms;

6. An electron transporting material represented by formula (1-2):

$$A_{12}(\text{-}L_{12}\text{-}L_{22}\text{-}L_{32}\text{-}L_{42}\text{-}Ar_{12})_q \quad (1\text{-}2)$$

wherein:

each of $L_{12}$, $L_{22}$, $L_{32}$, and $L_{42}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$Ar_{12}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms;

$A_{12}$ represents a q-valent residue of a compound represented by formula (2-2), (2-3), or (2-4); and q represents an integer of 1 or more:

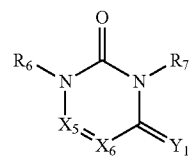

(2-2)

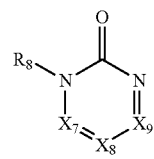

(2-3)

-continued (2-4)

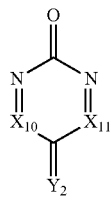

(2-3-1)

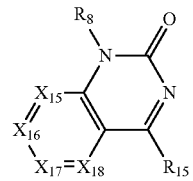

wherein:
each of $X_5$ to $X_{11}$ independently represents $CR_9$ or N;
each of $Y_1$ and $Y_2$ independently represents $CR_{10}R_{11}$ or $NR_{12}$;
each of $R_6$ to $R_{12}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{12}$; or $R_6$ to $R_{12}$ are each bonded to each other to form a ring Y selected from a substituted or unsubstituted hydrocarbon ring and a substituted or unsubstituted heteroring;

7. The electron transporting material according to item 6, wherein $A_{12}$ represents a q-valent residue of a compound represented by formula (2-2-1) or (2-3-1);

(2-2-1)

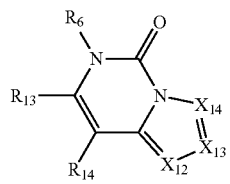

wherein:
each of $X_{12}$ to $X_{18}$ independently represents $CR_{16}$ or N;
each of $R_6$, $R_8$, and $R_{13}$ to $R_{16}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{12}$; or $R_6$, $R_8$, and $R_{13}$ to $R_{16}$ are each bonded to each other to form a substituted or unsubstituted hydrocarbon ring or a substituted or unsubstituted heteroring;

8. The electron transporting material according to item 6 or 7, wherein $A_{12}$ represents a q-valent residue of a compound represented by formula (2-2-1-1):

(2-2-1-1)

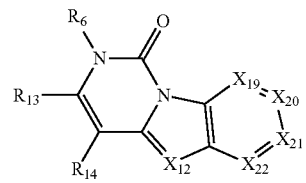

wherein:
each of $X_{12}$ and $X_{19}$ to $X_{22}$ independently represents $CR_{17}$ or N;

each of $R_6$, $R_{13}$, $R_{14}$, and $R_{17}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{12}$; or $R_6$, $R_{13}$, $R_{14}$, and $R_{17}$ are each bonded to each other to form a substituted or unsubstituted hydrocarbon ring or a substituted or unsubstituted heteroring;

9. The electron transporting material according to any one of items 6 to 8, wherein the electron transporting material is represented by formula (1-2-1):

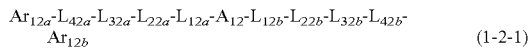

(1-2-1)

wherein:

each of $L_{12a}$, $L_{22a}$, $L_{32a}$, $L_{42a}$, $L_{12b}$, $L_{22b}$, $L_{32b}$, and $L_{42b}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$A_{12}$ represents a divalent residue of a compound represented by formula (2-2), (2-2-1), (2-2-1-1), (2-3), (2-3-1), or (2-4);

$Ar_{12a}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms; and $Ar_{12b}$ represents a substituted or unsubstituted aryl group having 12 to 30 ring carbon atoms or a substituted or unsubstituted heteroaryl group having 12 to 30 ring atoms;

10. The electron transporting material according to any one of items 1 to 9, wherein the ring Y represents a substituted or unsubstituted non-fused aromatic hydrocarbon ring having 6 to 30 ring carbon atoms, a substituted or unsubstituted fused aromatic hydrocarbon ring having 10 to 30 ring carbon atoms, a substituted or unsubstituted non-fused heteroring having 5 to 30 ring atoms, or a substituted or unsubstituted fused heteroring having 10 to 30 ring atoms;

11. A nitrogen-containing heterocyclic derivative represented by formula (1-1);

(1-1)

wherein;

each of $L_{11}$, $L_{21}$, $L_{31}$, and $L_{41}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$Ar_{11}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms;

$A_{11}$ represents a p-valent residue of a ring-containing compound represented by formula (2-1);

p represents an integer of 1 or more;

provided that at least one of $L_{11}$, $L_{21}$, $L_{31}$, and $L_1$ represents a group selected from a substituted or unsubstituted anthracenylene group, a substituted or unsubstituted phenanthrenylene group, a substituted or unsubstituted chrysenylene group, a substituted or unsubstituted pyrenylene group, a substituted or unsubstituted acenaphthylenylene group, a substituted or unsubstituted acenaphthenylene group, a substituted or unsubstituted fluoranthenylene group, a substituted or unsubstituted fluorenylene group, a substituted or unsubstituted naphthylene group, a substituted or unsubstituted benzofluoranthenylene group, a substituted or unsubstituted benzophenanthrenylene group, a substituted or unsubstituted benzochrysenylene group, a substituted or unsubstituted benzotriphenylenylene group, a substituted or unsubstituted benzanthracenylene group, a substituted or unsubstituted dibenzophenanthrenylene group, and a substituted or unsubstituted triphenylenylene group; or $Ar_{11}$ represents a group selected from a substituted or unsubstituted anthracenyl group, a substituted or unsubstituted chrysenyl group, a substituted or unsubstituted pyrenyl group, a substituted or unsubstituted acenaphthylenyl group, a substituted or unsubstituted acenaphthenyl group, a substituted or unsubstituted fluoranthenyl group, a substituted or unsubstituted fluorenyl group, a substituted or unsubstituted naphthyl group, a substituted or unsubstituted benzofluoranthenyl group, a substituted or unsubstituted benzophenanthrenyl group, a substituted or unsubstituted benzochrysenyl group, a substituted or unsubstituted benzotriphenylenyl group, a substituted or unsubstituted benzanthracenyl group, a substituted or unsubstituted dibenzophenanthrenyl group, and a substituted or unsubstituted triphenylenyl group:

(2-1)

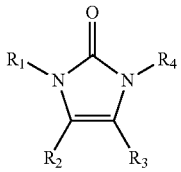

wherein:
each of $R_1$ to $R_4$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted arylthio group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted alkyl group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{11}$; or a pair of $R_1$ and $R_2$, $R_2$ and $R_3$, or $R_3$ and $R_4$ are bonded to each other to form a ring Y represented by a substituted or unsubstituted hydrocarbon ring or a substituted or unsubstituted heteroring;

12. The nitrogen-containing heterocyclic derivative according to item 11, wherein $A_{11}$ represents a p-valent residue of a compound represented by formula (2-1-1), (2-1-2), or (2-1-3):

(2-1-1)

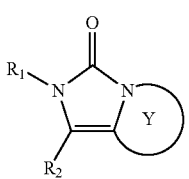

(2-1-2)

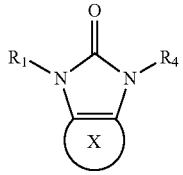

(2-1-3)

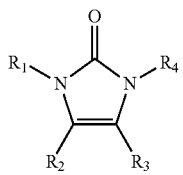

wherein:
each of $R_1$ to $R_4$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{11}$; and
Y represents the ring Y;

13. The nitrogen-containing heterocyclic derivative according to item 11 or 12, wherein $A_{11}$ represents a p-valent residue of a compound represented by formula (2-1-2-1);

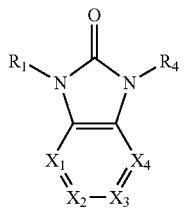

(2-1-2-1)

wherein:
each of $X_1$ to $X_4$ independently represents $CR_5$ or N;
each of $R_1$, $R_4$, and $R_5$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{11}$; or $R_1$, $R_4$, and $R_5$ are each bonded to each other to form a ring which forms a part of the ring Y;

14. The nitrogen-containing heterocyclic derivative according to any one of items 11 to 13, wherein the nitrogen-containing heterocyclic derivative is represented by formula (1-1-1):

$$Ar_{11a}\text{-}L_{41a}\text{-}L_{31a}\text{-}L_{21a}\text{-}L_{11a}\text{-}A_{11}\text{-}L_{11b}\text{-}L_{21b}\text{-}L_{31b}\text{-}L_{41b}\text{-}Ar_{11b} \quad (1\text{-}1\text{-}1)$$

wherein:
each of $L^{11a}$, $L_{21a}$, $L_{31a}$, $L_{41a}$, $L_{11b}$, $L_{21b}$, $L_{31b}$, and $L_{41b}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$A_{11}$ represent a divalent residue of a compound represented by formula (2-1), (2-1-1), (2-1-2), (2-1-3), or (2-1-2-1);

$Ar_{11a}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms; and $Ar_{11b}$ represents a substituted or unsubstituted aryl group having 12 to 30 ring carbon atoms, or a substituted or unsubstituted heteroaryl group having 12 to 30 ring atoms;

15. A nitrogen-containing heterocyclic derivative represented by formula (1-2):

$$A_{12}(\text{-}L_{12}\text{-}L_{22}\text{-}L_{32}\text{-}L_{42}\text{-}Ar_{12})_q \quad (1\text{-}2)$$

wherein:
each of $L_{12}$, $L_{22}$, $L_{32}$, and $L_{42}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$Ar_{12}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms;

$A_{12}$ represents a q-valent residue of a ring-containing compound represented by formula (2-2), (2-3), or (2-4); and q represents an integer of 1 or more;

provided that at least one of $L_{12}$, $L_{22}$, $L_{32}$, and $L_{42}$ represents a substituted or unsubstituted arylene group having 12 to 30 carbon atoms, or $Ar_{12}$ represents a substituted or unsubstituted aryl group having 12 to 30 carbon atoms:

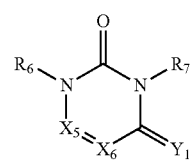

(2-2)

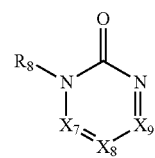

(2-3)

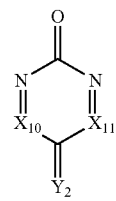

(2-4)

wherein:
each of $X_5$ to $X_{11}$ independently represents $CR_9$ or N;
each of $Y_1$ and $Y_2$ independently represents $CR_{10}R_{11}$ or $NR_{12}$;
each of $R_6$ to $R_{12}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{12}$; or $R_6$ to $R_{12}$ are each bonded to each other to form a ring Y represented by a substituted or unsubstituted hydrocarbon ring and a substituted or unsubstituted heteroring;

16. The nitrogen-containing heterocyclic derivative according to item 15, wherein $A_{12}$ represents a q-valent residue of a compound represented by formula (2-2-1) or (2-3-1):

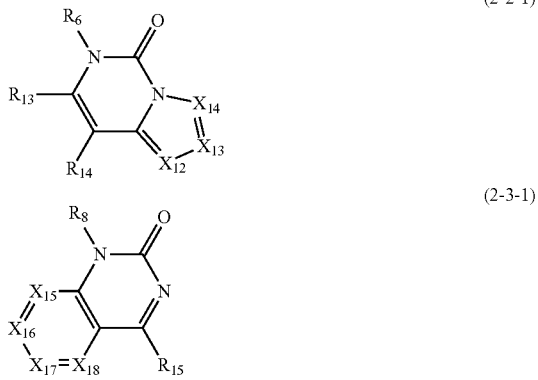

wherein:
each of $X_{12}$ to $X_{18}$ independently represents $CR_{16}$ or N;

each of $R_6$, $R_8$, and $R_{13}$ to $R_{16}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{12}$; or $R_6$, $R_8$, and $R_{13}$ to $R_{16}$ are each bonded to each other to form a substituted or unsubstituted hydrocarbon ring or a substituted or unsubstituted heteroring;

17. The nitrogen-containing heterocyclic derivative according to item 15 or 16, wherein $A_{12}$ represents a q-valent residue of a compound represented by formula (2-2-1-1):

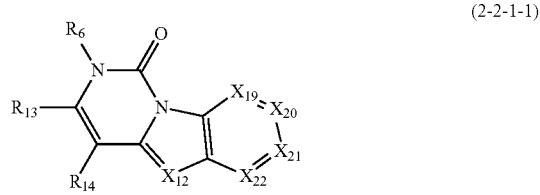

wherein:
each of $X_{12}$ and $X_{19}$ to $X_{22}$ independently represents $CR_{17}$ or N;
each of $R_6$, $R_{13}$, $R_{14}$, and $R_{17}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{12}$; or $R_6$, $R_{13}$, $R_{14}$, and $R_{17}$ are each bonded to each other to form a substituted or unsubstituted hydrocarbon ring or a substituted or unsubstituted heteroring;

18. The nitrogen-containing heterocyclic derivative according to any one of items 15 to 17, which is represented by formula (1-2-1):

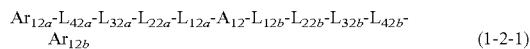

$Ar_{12a}-L_{42a}-L_{32a}-L_{22a}-L_{12a}-A_{12}-L_{12b}-L_{22b}-L_{32b}-L_{42b}-Ar_{12b}$ (1-2-1)

wherein:

each of $L_{12a}$, $L_{22a}$, $L_{32a}$, $L_{42a}$, $L_{12b}$, $L_{22b}$, $L_{32b}$, and $L_{42b}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$A_{12}$ represents a divalent residue of a compound represented by formula (2-2), (2-2-1), (2-2-1-1), (2-3), (2-3-1, or (2-4);

$Ar_{12a}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms; and $Ar_{12b}$ represents a substituted or unsubstituted aryl group having 12 to 30 ring carbon atoms, or a substituted or unsubstituted heteroaryl group having 12 to 30 ring atoms;

19. The nitrogen-containing heterocyclic derivative according to any one of items of 11 to 18, wherein the ring Y is selected from a substituted or unsubstituted non-fused aromatic hydrocarbon ring having 6 to 30 ring carbon atoms, a substituted or unsubstituted fused aromatic hydrocarbon ring having 10 to 30 ring carbon atoms, a substituted or unsubstituted non-fused heteroring having 5 to 30 ring atoms, and a substituted or unsubstituted fused heteroring having 10 to 30 ring atoms;

20. A material for organic electroluminescence devices comprising the aromatic heterocyclic derivative according to any one of items 11 to 19;

21. An organic electroluminescence device comprising a light emitting layer and an electron transporting layer which are disposed between a cathode and an anode, wherein the electron transporting layer comprises the electron transporting material according to any one of items 1 to 10;

22. An organic electroluminescence device comprising a light emitting layer and an electron transporting layer which are disposed between a cathode and an anode, wherein the electron transporting layer comprises the nitrogen-containing heterocyclic derivative according to any one of items 11 to 19;

23. The organic electroluminescence device according to item 21 or 22, wherein the electron transporting layer further comprises a reducing dopant;

24. The organic electroluminescence device according to item 23, wherein the reducing dopant is a compound comprising at least one metal selected from the group consisting of alkali metals, alkaline earth metals, and rare earth metals; and 25. The organic electroluminescence device according to item 24, wherein the reducing dopant is at least one selected from the group consisting of alkali metals, alkali metal oxides, alkali metal halides, alkaline earth metal oxides, alkaline earth metal halides, rare earth metal oxides, and rare earth metal halides.

Effect of the Invention

By using the nitrogen-containing heterocyclic derivative of the invention, an organic EL device having a high emission efficiency even at a low driving voltage is obtained.

MODE FOR CARRYING OUT THE INVENTION

The present invention provides an electron transporting material represented by formula (1):

$A_1(-L_1-L_2-L_3-L_4-Ar_1)_m$ (1)

wherein:

each of $L_1$, $L_2$, $L_3$, and $L_4$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$Ar_1$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms;

$A_1$ represents an m-valent residue of a ring-containing compound represented by formula (2); and m represents an integer of 1 or more:

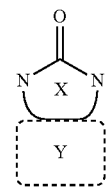

(2)

wherein:
ring X is a substituted or unsubstituted, saturated or unsaturated 5- to 8-membered ring having a ring nitrogen atom and a ring carbon atom;
the ring X may be fused to one or more rings Y; and
the ring Y represents a substituted or unsubstituted hydrocarbon ring or a substituted or unsubstituted heteroring;
The ring Y preferably represents a substituted or unsubstituted non-fused aromatic hydrocarbon ring having 6 to 30 ring carbon atoms, a substituted or unsubstituted fused aromatic hydrocarbon ring having 10 to 30 ring carbon atoms, a substituted or unsubstituted non-fused heteroring having 5 to 30 ring atoms, or a substituted or unsubstituted fused heteroring having 10 to 30 ring atoms.

The electron transporting material of the invention is preferably represented by formula (1-1) or (1-2):

$$A_{11}(-L_{11}-L_{21}-L_{31}-L_{41}-Ar_{11})_p \quad (1\text{-}1)$$

wherein:
each of $L_{11}$, $L_{21}$, $L_{31}$, and $L_{41}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;
$Ar_{11}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms;
$A_{11}$ represents a p-valent residue of a ring-containing compound represented by formula (2-1); and
p represents an integer of 1 or more:

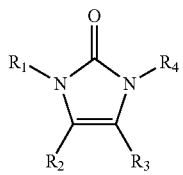

(2-1)

wherein;
each of $R_1$ to $R_4$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, a boryl group, a phosphino group, an amino group, a halogen atom, a cyano group, a nitro group, a hydroxyl group, a carboxyl group, or a valence bonded to $L_{11}$; or a pair of $R_1$ and $R_2$, $R_2$ and $R_3$, or $R_3$ and $R_4$ are bonded to each other to form a ring Y represented by a substituted or unsubstituted hydrocarbon ring or a substituted or unsubstituted heteroring.

$A_{11}$ of formula (1-1) preferably represents a p-valent residue of a compound represented by formula (2-1-1), (2-1-2), or (2-1-3):

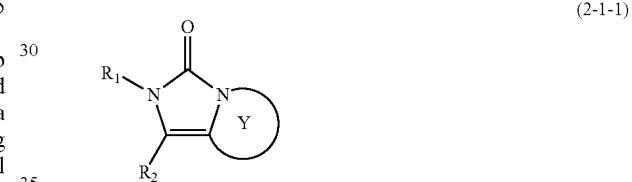

(2-1-1)

(2-1-2)

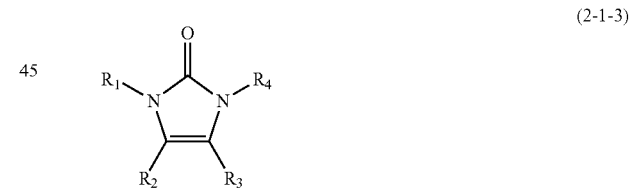

(2-1-3)

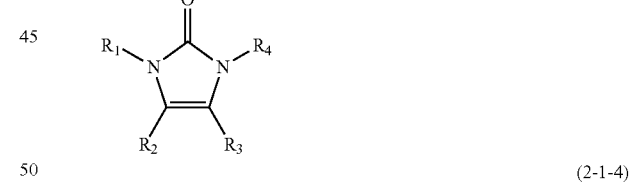

(2-1-4)

wherein:
each of $R_1$ to $R_4$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted arylthio group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, an amino group substituted by a substituted or unsubstituted alkyl group having 1 to 50 carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{11}$; and Y represents the ring Y.

Further, $A_{11}$ preferably represents a p-valent residue of a compound represented by formula (2-1-2-1):

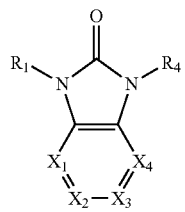

(2-1-2-1)

wherein:

each of $X_1$ to $X_4$ independently represents $CR_5$ or N;

each of $R_1$, $R_4$, and $R_5$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{11}$; or $R_1$, $R_4$, and $R_5$ are each bonded to each other to form a ring which forms a part of the ring Y.

Examples of the compound represented by formula (2-1) are shown below.

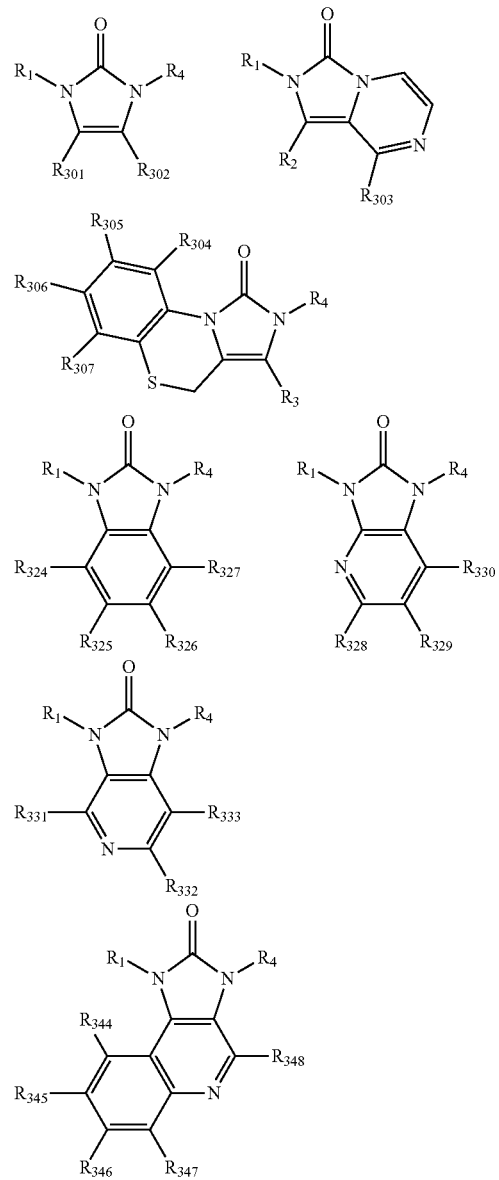

-continued

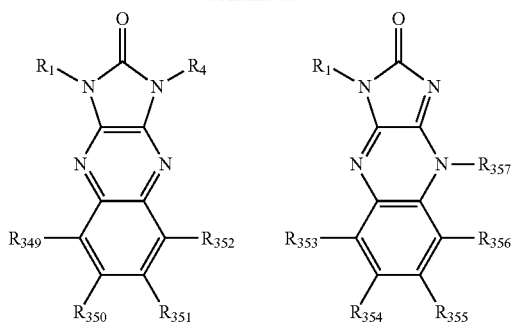

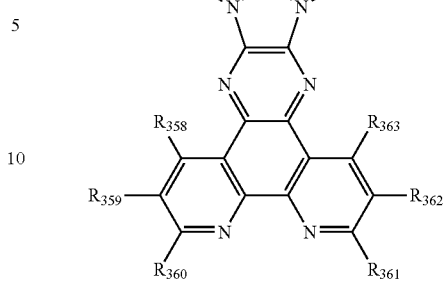

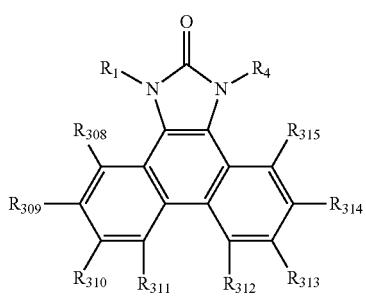

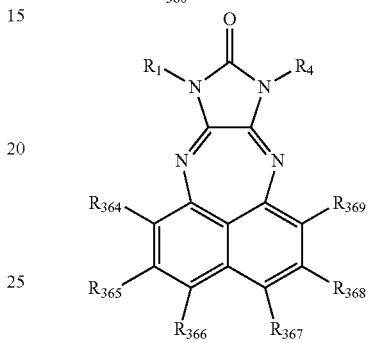

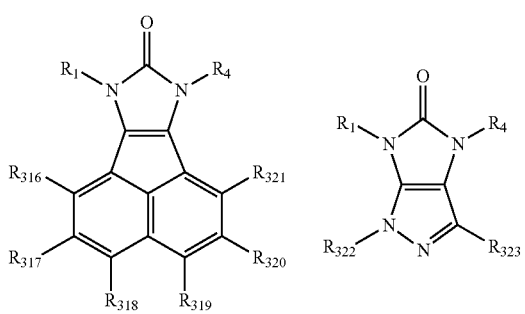

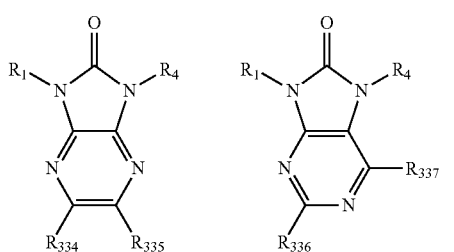

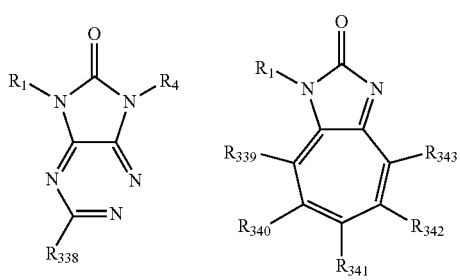

In the above formulae, each of $R_1$ to $R_4$, $R_{4'}$, and $R_{301}$ to $R_{369}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{11}$; or $R_1$, $R_4$, and $R_{301}$ to $R_{369}$ are each bonded to each other to form a substituted or unsubstituted hydrocarbon ring or a substituted or unsubstituted heteroring.

The electron transporting material represented by formula (1-1) is particularly preferably represented by formula (1-1a) or (1-1-1):

$$Ar_{21a}\text{-}A_{11a}\text{-}L_{11a}\text{-}L_{21a}\text{-}L_{31a}\text{-}L_{41a}\text{-}Ar_{11a} \quad (1\text{-}1a)$$

wherein:

each of $L_{11a}$, $L_{21a}$, $L_{31a}$, and $L_{41a}$ independently represents a single bond, an arylene group having 6 to 30 ring carbon atoms, or a heteroarylene group having 5 to 30 ring atoms;

each of $Ar_{11a}$ and $Ar_{21a}$ independently represents an alkyl group having 1 to 5 carbon atoms, a cycloalkyl group having 3 to 30 ring carbon atoms, an aryl group having 6 to 30 ring carbon atoms, or a heteroaryl group having 5 to 30 ring atoms; and $A_{11a}$ represents a divalent group represented by formula (2-1-2-1a):

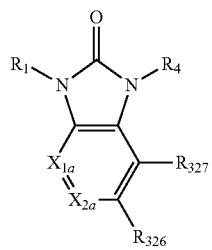

(2-1-2-1a)

wherein:

each of $X_{1a}$ and $X_{2a}$ independently represents $CR_{5a}$ or N;

each of $R_1$, $R_4$, $R_{326}$, $R_{327}$, and $R_{5a}$ independently represents a hydrogen atom, an alkyl group having 1 to 5 carbon atoms (preferably, methyl group and ethyl group), a cycloalkyl group having 5 to 18 ring carbon atoms (preferably, cyclohexyl group), an aryl group having 6 to 18 ring carbon atoms (preferably, phenyl group, biphenylyl group, and naphthyl group), a heteroaryl group having 5 to 18 ring atoms, or a valence bonded to $L_{12a}$;

at least one of $X_{1a}$ and $X_{2a}$ preferably represents $CR_{5a}$; and $R_{5a}$ preferably represents a hydrogen atom, an alkyl group having 1 to 5 carbon atoms, or a phenyl group; or $$Ar_{11a}\text{-}L_{41a}\text{-}L_{31a}\text{-}L_{21a}\text{-}L_{11a}\text{-}A_{11}\text{-}L_{11b}\text{-}L_{21b}\text{-}L_{31b}\text{-}L_{41b}\text{-}Ar_{11b} \quad (1\text{-}1\text{-}1)$$

wherein:

each of $L_{11a}$, $L_{21a}$, $L_{31a}$, $L_{41a}$, $L_{11b}$, $L_{21b}$, $L_{31b}$, and $L_{41b}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$A_{11}$ represents a divalent residue of a compound represented by formula (2-1), (2-1-1), (2-1-2), (2-1-3), or (2-1-2-1);

$Ar_{11a}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms; and $Ar_{11b}$ represents a substituted or unsubstituted aryl group having 12 to 30, preferably 13 to 30 ring carbon atoms or a substituted or unsubstituted heteroaryl group having 12 to 30, preferably 14 to 30 ring atoms.

The electron transporting material represented by formula (1-1-1) is preferable in view of achieving the effects of the invention, because $Ar_{11b}$ represents a substituted or unsubstituted aryl group having 12 to 30 ring carbon atoms or a substituted or unsubstituted heteroaryl group having 12 to 30 ring atoms, to increase the asymetricity of the molecule. In view of the asymetricity, it is preferred that $Ar_{11a}$ represents an alkyl group having 1 to 5 carbon atoms (more preferably, methyl group and ethyl group), a cycloalkyl group having 5 to 12 ring carbon atoms (more preferably, cyclohexyl group), an aryl group having 6 to 12 ring carbon atoms (more preferably, phenyl group, biphenylyl group, and naphthyl group), or a heteroaryl group having 5 to 12 ring atoms.

In formula (1-1-1), the definition and examples of $Ar_{11a}$ and $Ar_{11b}$ are the same as those of $Ar_{11}$, the definition and examples of $L_{11a}$ and $L_{11b}$ are the same as those of $L_{11}$, the definition and examples of $L_{21a}$ and $L_{21b}$ are the same as those of $L_{21}$, the definition and examples of $L_{31a}$ and $L_{31b}$ are the same as those of $L_{31}$, and the definition and examples of $L_{41a}$ and $L_{41b}$ are the same as those of $L_{41}$.

Further, the electron transporting material is preferably represented by formula (1-2):

$$A_{12}(\text{-}L_{12}\text{-}L_{22}\text{-}L_{32}\text{-}L_{42}\text{-}Ar_{12})_q \quad (1\text{-}2)$$

wherein:

each of $L_{12}$, $L_{22}$, $L_{32}$, and $L_{42}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$Ar_{12}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms;

$A_{12}$ represents a q-valent residue of a compound represented by formula (2-2), (2-3), or (2-4); and q represents an integer of 1 or more:

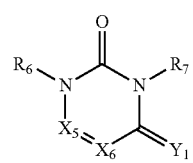

(2-2)

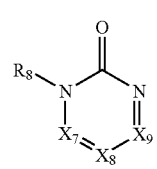

(2-3)

-continued

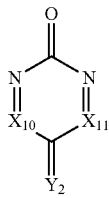

(2-4)

wherein:
each of $X_5$ to $X_{11}$ independently represents $CR_9$ or N;
each of $Y_1$ and $Y_2$ independently represents $CR_{10}R_{11}$ or $NR_{12}$;
each of $R_6$ to $R_{12}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{12}$; or $R_6$ to $R_{12}$ are each bonded to each other to form a substituted or unsubstituted hydrocarbon ring and a substituted or unsubstituted heteroring.

In formula (1-2), at least one of $L_{12}$, $L_{22}$, $L_{32}$, and $L_{42}$ preferably represents a substituted or unsubstituted anthracenylene group, a substituted or unsubstituted phenanthrenylene group, a substituted or unsubstituted chrysenylene group, a substituted or unsubstituted pyrenylene group, a substituted or unsubstituted acenaphthylenylene group, a substituted or unsubstituted acenaphthenylene group, a substituted or unsubstituted fluoranthenylene group, a substituted or unsubstituted fluorenylene group, a substituted or unsubstituted naphthylene group, a substituted or unsubstituted benzofluoranthenylene group, a substituted or unsubstituted benzophenanthrenylene group, a substituted or unsubstituted benzochrysenylene group, a substituted or unsubstituted benzotriphenylenylene group, a substituted or unsubstituted benzanthracenylene group, a substituted or unsubstituted dibenzophenanthrenylene group, or a substituted or unsubstituted triphenylenylene group; or $Ar_{12}$ preferably represents a substituted or unsubstituted anthracenyl group, a substituted or unsubstituted phenanthrenyl group, a substituted or unsubstituted chrysenyl group, a substituted or unsubstituted pyrenyl group, a substituted or unsubstituted acenaphthylenyl group, a substituted or unsubstituted acenaphthenyl group, a substituted or unsubstituted fluoranthenyl group, a substituted or unsubstituted fluorenyl group, a substituted or unsubstituted naphthyl group, a substituted or unsubstituted benzofluoranthenyl group, a substituted or unsubstituted benzophenanthrenyl group, a substituted or unsubstituted benzochrysenyl group, a substituted or unsubstituted benzotriphenylenyl group, a substituted or unsubstituted benzanthracenyl group, a substituted or unsubstituted dibenzophenanthrenyl group, or a substituted or unsubstituted triphenylenyl group.

$A_{12}$ preferably represents a q-valent residue of a compound represented by formula (2-2-1) or (2-3-1):

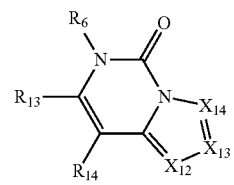

(2-2-1)

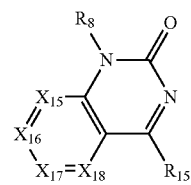

(2-3-1)

wherein:
each of $X_{12}$ to $X_{18}$ independently represents $CR_{16}$ or N;
each of $R_6$, $R_8$, and $R_{13}$ to $R_{16}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{12}$; or $R_6$, $R_8$, and $R_{13}$ to $R_{16}$ are each bonded to each other to form a substituted or unsubstituted hydrocarbon ring or a substituted or unsubstituted heteroring.

$A_{12}$ preferably represents a q-valent residue of a compound represented by formula (2-2-1-1):

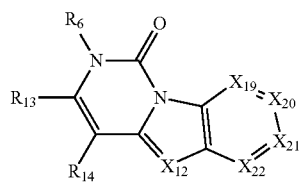

(2-2-1-1)

wherein:

each of $X_{12}$ and $X_{19}$ to $X_{22}$ independently represents $CR_{17}$ or N;

each of $R_6$, $R_{13}$, $R_{14}$, and $R_{17}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{12}$; or $R_6$, $R_{13}$, $R_{14}$, and $R_{17}$ are each bonded to each other to form a substituted or unsubstituted hydrocarbon ring or a substituted or unsubstituted heteroring.

Examples of the compounds represented by formula (2-2), (2-3), and (2-4) are shown below.

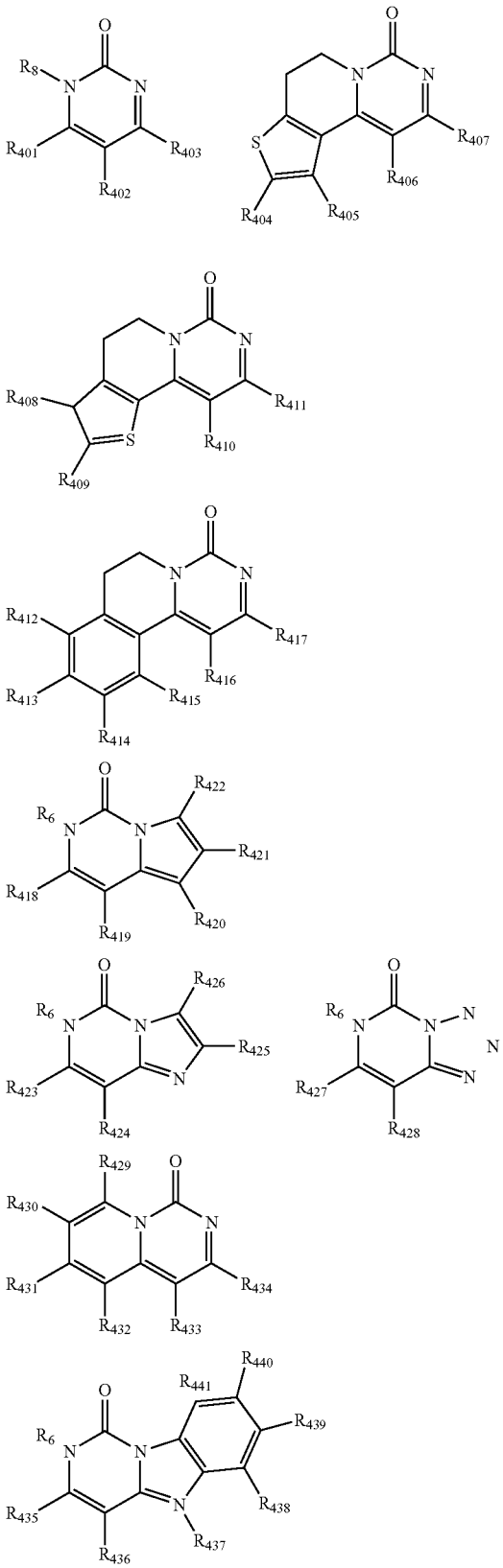

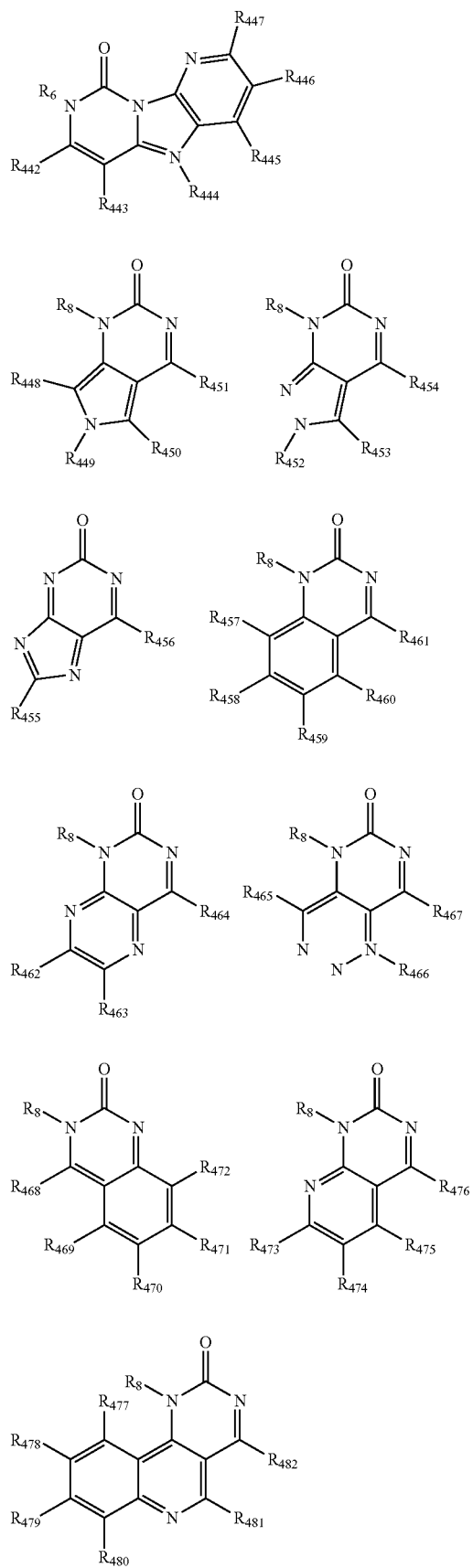
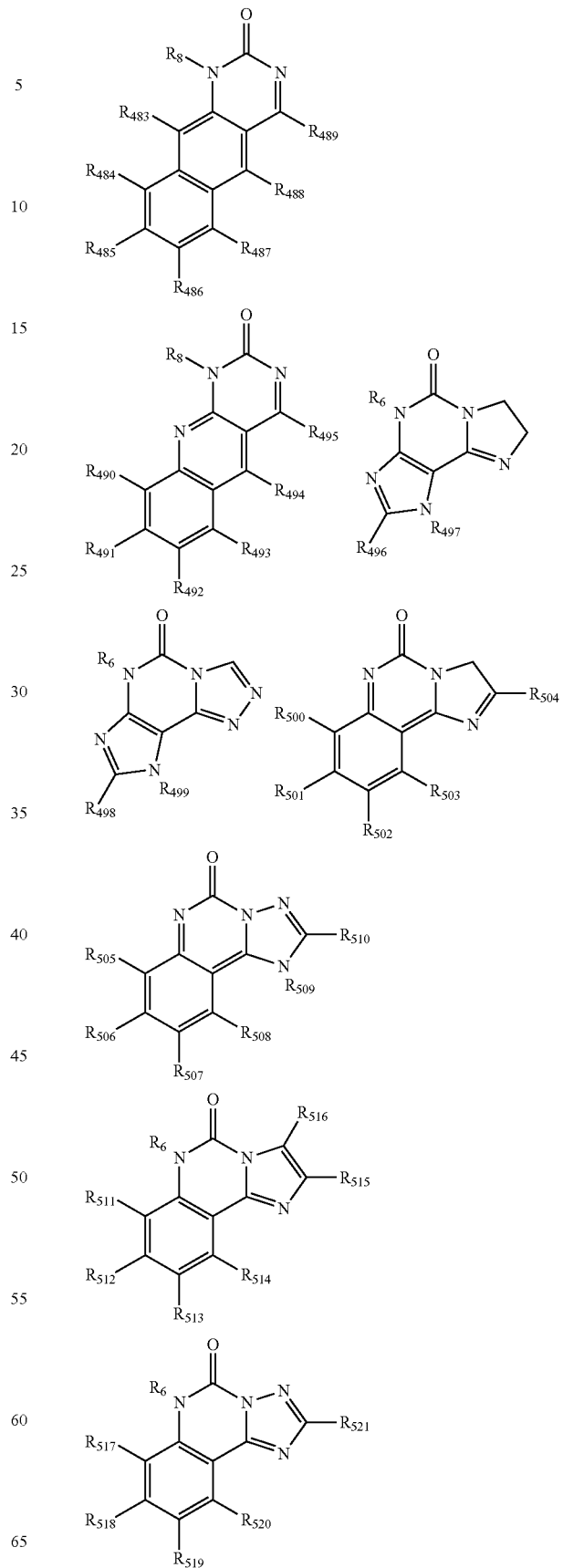

-continued

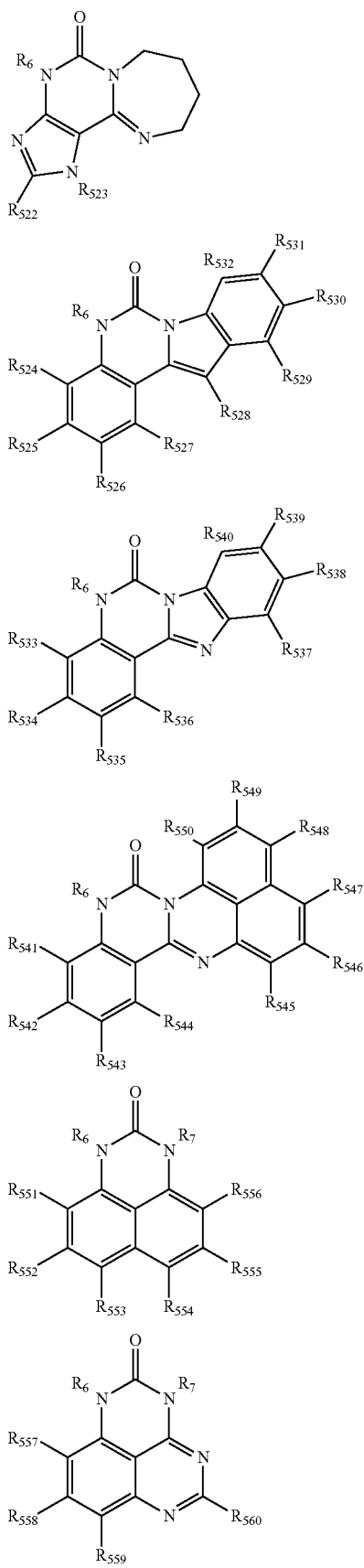

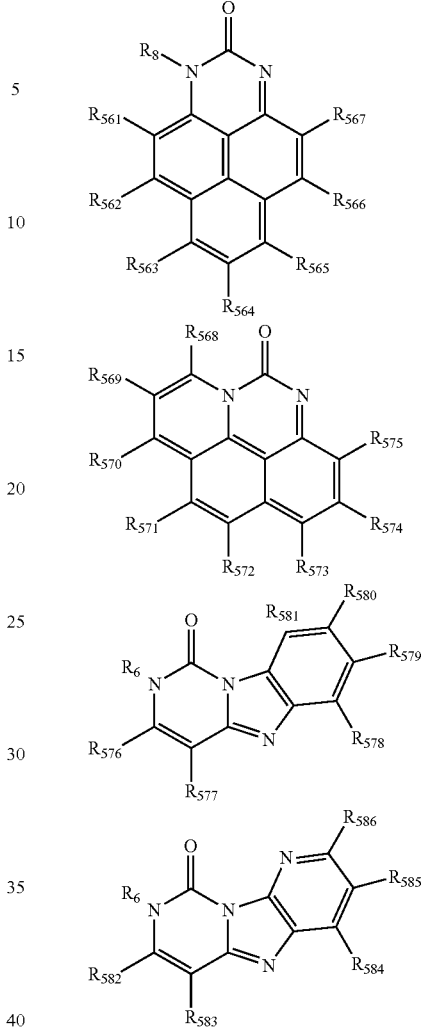

wherein:
each of $R_6$ to $R_8$ and $R_{401}$ to $R_{586}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{12}$; or $R_6$ to $R_8$ and $R_{401}$ to $R_{586}$ are each bonded to each other to form a substituted or unsubstituted hydrocarbon ring or a substituted or unsubstituted heteroring.

The electron transporting material represented by formula (1-2) is particularly preferably represented by formula (1-2a):

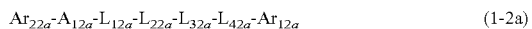

$$Ar_{22a}\text{-}A_{12a}\text{-}L_{12a}\text{-}L_{22a}\text{-}L_{32a}\text{-}L_{42a}\text{-}Ar_{12a} \qquad (1\text{-}2a)$$

wherein:

each of $L_{12a}$, $L_{22a}$, $L_{32a}$, and $L_{42a}$ independently represents a single bond, an arylene group having 6 to 30 ring carbon atoms, or a heteroarylene group having 5 to 30 ring atoms;

each of $Ar_{12a}$ and $Ar_{22a}$ represents an alkyl group having 1 to 5 carbon atoms, a cycloalkyl group having 3 to 30 ring carbon atoms, an aryl group having 6 to 30 ring carbon atoms, or a heteroaryl group having 5 to 30 ring atoms; and $A_{12a}$ represents a divalent group represented by formula (2-2-1-1a);

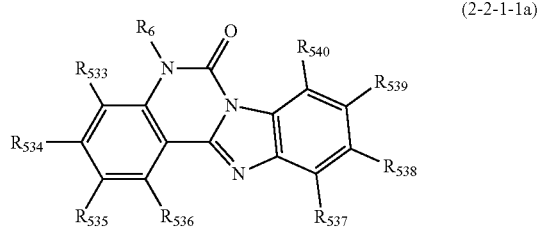

(2-2-1-1a)

wherein:

each of $R_6$ and $R_{533}$ to $R_{540}$ independently represents a hydrogen atom, an alkyl group having 1 to 5 carbon atoms (preferably, methyl group and ethyl group), a cycloalkyl group having 5 to 18 ring carbon atoms (preferably, cyclohexyl group), an aryl group having 6 to 18 ring carbon atoms (preferably, phenyl group, biphenylyl group, and naphthyl group), a heteroaryl group having 5 to 18 ring atoms, or a valence bonded to $L_{12a}$.

$R_6$ preferably represents a hydrogen atom, an alkyl group having 1 to 5 carbon atoms, or a phenyl group.

Further, the electron transporting material is preferably represented by formula (1-2-1):

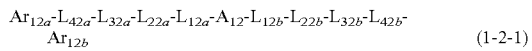

$$Ar_{12a}\text{-}L_{42a}\text{-}L_{32a}\text{-}L_{22a}\text{-}L_{12a}\text{-}A_{12}\text{-}L_{12b}\text{-}L_{22b}\text{-}L_{32b}\text{-}L_{42b}\text{-}Ar_{12b} \qquad (1\text{-}2\text{-}1)$$

wherein:

each of $L_{12a}$, $L_{22a}$, $L_{32a}$, $L_{42a}$, $L_{12b}$, $L_{22b}$, $L_{32b}$, and $L_{42}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$A_{12}$ represents a divalent residue of a compound represented by formula (2-2), (2-2-1), (2-2-1-1), (2-3), (2-3-1), or (2-4);

$Ar_{12a}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms; and $Ar_{12b}$ represents a substituted or unsubstituted aryl group having 12 to 30, preferably 13 to 30 ring carbon atoms or a substituted or unsubstituted heteroaryl group having 12 to 30, preferably 14 to 30 ring atoms.

The electron transporting material represented by formula (1-2-1) is preferable in view of achieving the effects of the invention, because $Ar_{12b}$ represents a substituted or unsubstituted aryl group having 12 to 30 ring carbon atoms or a substituted or unsubstituted heteroaryl group having 12 to 30 ring atoms, to increase the asymetricity of the molecule. In view of the asymetricity, it is preferred that $Ar_{12a}$ represents an alkyl group having 1 to 5 carbon atoms (more preferably, methyl group and ethyl group), a cycloalkyl group having 5 to 12 ring carbon atoms (more preferably, cyclohexyl group), an aryl group having 6 to 12 ring carbon atoms (more preferably, phenyl group, biphenylyl group, and naphthyl group), or a heteroaryl group having 5 to 12 ring atoms.

In formula (1-2-1), the definition and examples of $Ar_{12a}$ and $Ar_{12b}$ are the same as those of $Ar_{12}$, the definition and examples of $L_{12a}$ and $L_{12b}$ are the same as those of $L_{12}$, the definition and examples of $L_{22a}$ and $L_{22b}$ are the same as those of $L_{22}$, the definition and examples of $L_{32a}$ and $L_{32b}$ are the same as those of $L_{32}$, and the definition and examples of $L_{42a}$ and $L_{42}$ are the same as those of $L_{42}$.

Examples of the substituted or unsubstituted aryl groups and heteroaryl groups for $Ar_1$, $Ar_{11}$, $Ar_{12}$, $Ar_{11a}$, $Ar_{21a}$, $Ar_{12a}$, $Ar_{22a}$, $R_1$ to $R_{17}$, $R_{301}$ to $R_{369}$, and $R_{401}$ to $R_{586}$ include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group, fluoranthenyl group, fluorenyl group, 9,9-dimethylfluorenyl group, 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, 2,2'-bipyridyl group, 2,3'-bipyridyl group, 2,4'-bipyridyl group, 3,2'-bipyridyl group, 3,3'-bipyridyl group, 3,4'-bipyridyl group, 4,2'-bipyridyl group, 4,3'-bipyridyl group, (p-pyrid-4-yl) phenyl group, (p-pyrid-3-yl)phenyl group, (p-pyrid-2-yl) phenyl group, (m-pyrid-4-yl)phenyl group, (m-pyrid-3-yl) phenyl group, and (m-pyrid-2-yl)phenyl group, with phenyl group, naphthyl group, biphenyl group, anthracenyl group, phenanthryl group, pyrenyl group, chrysenyl group, fluoranthenyl group, and 9,9-dimethylfluorenyl group being preferred.

Examples of the substituted or unsubstituted alkyl group having 1 to 50, preferably 1 to 20, more preferably 1 to 10 carbon atoms for $Ar_1$, $Ar_{11}$, $Ar_{12}$, $A_{11a}$, $Ar_{21a}$, $Ar_{12a}$, $Ar_{22a}$, $R_1$ to $R_{17}$, $R_{301}$ to $R_{369}$, and $R_{401}$ to $R_{586}$ include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, fluoromethyl group, difluoromethyl group, trifluoromethyl group, 1-fluoroethyl group, 2-fluoroethyl group, 2,2,2-trifluoroethyl group, 3,3,3,2,2-pentafluoroethyl group, 2-fluoroisobutyl group, 1,2-fluoroethyl group, 1,3-fluoroisopropyl group, 2,3-fluoro-t-butyl group, 1,2,3-trifluoropropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, and 1,2,3-trinitropropyl group.

Examples of the substituted or unsubstituted cycloalkyl group having 3 to 50, preferably 3 to 20, more preferably 3 to 10 ring carbon atoms for $A_1$, $Ar_{11}$, $Ar_{12}$, $Ar_{11a}$, $Ar_{21a}$, $Ar_{12a}$, $Ar_{22a}$, $R_1$ to $R_{17}$, $R_{301}$ to $R_{369}$, and $R_{401}$ to $R_{586}$ include cyclopropyl group, cyclobutyl group, cyclopentyl group, cyclohexyl group, 4-methylcyclohexyl group, 1-adamantyl group, 2-adamantyl group, 1-norbornyl group, and 2-norbornyl group.

Examples of the substituted or unsubstituted aralkyl group having 6 to 50 ring carbon atoms for $A_1$, $Ar_{11}$, $Ar_{12}$, $Ar_{11a}$, $Ar_{21a}$, $Ar_{12a}$, $Ar_{22a}$, $R_1$ to $R_{17}$, $R_{301}$ to $R_{369}$, and $R_{401}$ to $R_{586}$ include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group.

The substituted or unsubstituted alkoxy group having 1 to 50 carbon atoms (preferably 1 to 20 carbon atoms, more preferably 1 to 10 carbon atoms) for $R_1$ to $R_{17}$, $R_{301}$ to $R_{369}$, and $R_{401}$ to $R_{586}$ is represented by —OZ, wherein Z is an alkyl group which is selected from those mentioned above.

The substituted or unsubstituted aryloxy group having 6 to 50 ring carbon atoms for $R_1$ to $R_{17}$, $R_{301}$ to $R_{369}$, and $R_{401}$ to $R_{586}$ is represented by —OZ', wherein Z' is an aryl group which is selected from those mentioned above.

The substituted or unsubstituted heteroaryloxy group having 5 to 30 ring atoms for $R_1$ to $R_{17}$, $R_{301}$ to $R_{369}$, and $R_{401}$ to $R_{586}$ is represented by —OZ'', wherein Z'' is a heteroaryl group which is selected from those mentioned above.

The substituted or unsubstituted arylthio group having 6 to 50 ring carbon atoms for $R_1$ to $R_{17}$, $R_{301}$ to $R_{369}$, and $R_{401}$ to $R_{586}$ is represented by —SZ', wherein Z' is an aryl group which is selected from those mentioned above.

The substituted or unsubstituted alkoxycarbonyl group having 1 to 50 carbon atoms (preferably 1 to 20 carbon atoms, more preferably 1 to 10 carbon atoms) for $R_1$ to $R_{17}$, $R_{301}$ to $R_{369}$, and $R_{401}$ to $R_{586}$ is represented by —COOZ, wherein Z is an alkyl group which is selected from those mentioned above.

The aryl group of the substituted or unsubstituted arylamino group having 6 to 30 ring carbon atoms for $R_1$ to $R_{17}$, $R_{301}$ to $R_{369}$, and $R_{401}$ to $R_{586}$ is selected from those mentioned above.

The heteroaryl group of the substituted or unsubstituted heteroarylamino group having 5 to 30 ring atoms for $R_1$ to $R_{17}$, $R_{301}$ to $R_{369}$, and $R_{401}$ to $R_{586}$ is selected from those mentioned above.

The alkyl group of the substituted or unsubstituted acyl group having 2 to 50 carbon atoms for $R_1$ to $R_{17}$, $R_{301}$ to $R_{369}$, and $R_{401}$ to $R_{586}$ is selected from those mentioned above.

The alkyl group of the substituted or unsubstituted acylamino group having 2 to 50 carbon atoms for $R_1$ to $R_{17}$, $R_{301}$ to $R_{369}$, and $R_{401}$ to $R_{586}$ is selected from those mentioned above.

The aryl group of the substituted or unsubstituted aryloxycarbonyl group having 6 to 30 ring carbon atoms for $R_1$ to $R_{17}$, $R_{301}$ to $R_{369}$, and $R_{401}$ to $R_{586}$ is selected from those mentioned above.

The alkyl group of the substituted or unsubstituted alkylcarbonyl group having 1 to 50 carbon atoms for $R_1$ to $R_{17}$, $R_{301}$ to $R_{369}$, and $R_{401}$ to $R_{586}$ is selected from those mentioned above.

The alkyl group of the substituted or unsubstituted alkylthio group having 1 to 50 carbon atoms for $R_1$ to $R_{17}$, $R_{301}$ to $R_{369}$, and $R_{401}$ to $R_{586}$ is selected from those mentioned above.

The sulfonyl group for $R_1$ to $R_{17}$, $R_{301}$ to $R_{369}$, and $R_{401}$ to $R_{586}$ is represented by —SO$_2$Z, wherein Z is an alkyl group which is selected from those mentioned above.

The halogen atom for $R_1$ to $R_{17}$, $R_{301}$ to $R_{369}$, and $R_{401}$ to $R_{586}$ is a fluorine atom, a fluorine atom, a chlorine atom, a bromine atom, or an iodine atom, with a fluorine atom being preferred.

The halogen atom for $R_1$ to $R_{17}$, $R_{301}$ to $R_{369}$, and $R_{401}$ to $R_{586}$ is a fluorine atom, a fluorine atom, a chlorine atom, a bromine atom, or an iodine atom, with a fluorine atom being preferred.

The substituted or unsubstituted alkylsilyl group having 1 to 50 carbon atoms (preferably 1 to 20 carbon atoms, more preferably 1 to 10 carbon atoms) for $R_1$ to $R_{17}$, $R_{301}$ to $R_{369}$, and $R_{401}$ to $R_{586}$ includes, for example, trimethylsilyl group, triethylsilyl group, tributylsilyl group, dimethylethylsilyl group, dimethylisopropylsilyl group, dimethylpropylsilyl group, dimethylbutylsilyl group, dimethyl-t-butylsilyl group, and diethylisopropylsilyl group.

The substituted or unsubstituted arylsilyl group having 6 to 50 ring carbon atoms for $R_1$ to $R_{17}$, $R_{301}$ to $R_{369}$, and $R_{401}$ to $R_{586}$ includes, for example, phenyldimethylsilyl group, diphenylmethylsilyl group, diphenyl-t-butylsilyl group, and triphenylsilyl group.

The substituted or unsubstituted alkylamino group having 1 to 50 carbon atoms (preferably 1 to 20 carbon atoms, more preferably 1 to 10 carbon atoms) for $R_1$ to $R_{17}$, $R_{301}$ to $R_{369}$, and $R_{401}$ to $R_{586}$ includes, for example, methylamino group, dimethylamino group, diethylamino group, and di-n-propylamino group.

The substituted or unsubstituted haloalkyl group having 1 to 50 carbon atoms (preferably 1 to 20 carbon atoms, more preferably 1 to 10 carbon atoms) for $R_1$ to $R_{17}$, $R_{301}$ to $R_{369}$, and $R_{401}$ to $R_{586}$ includes, for example, the alkyl groups mentioned above which are substituted by one or more halogen atoms.

Examples of the substituted or unsubstituted alkenyl group having 1 to 50 carbon atoms (preferably 2 to 20 carbon atoms, more preferably 2 to 10 carbon atoms) for $R_1$ to $R_{17}$, $R_{301}$ to $R_{369}$, and $R_{401}$ to $R_{586}$ include monovalent groups which are derived from the alkyl groups mentioned above by removing tow hydrogen atoms to form a double bond between two carbon atoms.

The substituted or unsubstituted alkynyl group having 1 to 50 carbon atoms (preferably 2 to 20 carbon atoms, more preferably 2 to 10 carbon atoms) for $R_1$ to $R_{17}$, $R_{301}$ to $R_{369}$, and $R_{401}$ to $R_{586}$ includes monovalent groups which are derived from the alkyl groups mentioned above by removing four hydrogen atoms to form a triple bond between two carbon atoms.

Examples of the substituted or unsubstituted alkylene group having 1 to 50 carbon atoms (preferably 1 to 20 carbon atoms, more preferably 1 to 10 carbon atoms) for $L_1$, $L_2$, $L_3$, $L_4$, $L_{11}$, $L_{21}$, $L_{31}$, $L_{41}$, $L_{12}$, $L_{22}$, $L_{32}$, and $L_{42}$ include divalent groups which are derived from the alkyl groups mentioned above by removing one hydrogen atom.

Examples of the substituted or unsubstituted alkenylene group having 1 to 50 carbon atoms (preferably 1 to 20 carbon atoms, more preferably 1 to 10 carbon atoms) for $L_1$, $L_2$, $L_3$, $L_4$, $L_{11}$, $L_{21}$, $L_{31}$, $L_{41}$, $L_{12}$, $L_{22}$, $L_{32}$, and $L_{42}$ include divalent groups which are derived from the alkylene groups mentioned above by removing two hydrogen atoms to form a double bond between two carbon atoms.

Examples of the substituted or unsubstituted alkynylene group having 1 to 50 carbon atoms (preferably 1 to 20 carbon atoms, more preferably 1 to 10 carbon atoms) for $L_1$, $L_2$, $L_3$, $L_4$, $L_{11}$, $L_{21}$, $L_{31}$, $L_{41}$, $L_{12}$, $L_{22}$, $L_{32}$, and $L_{42}$ include divalent groups which are derived from the alkylene groups by removing four hydrogen atoms to form a triple bond between two carbon atoms.

Examples of the substituted or unsubstituted cycloalkylene group having 3 to 50 ring carbon atoms (preferably 3 to 20 ring carbon atoms, more preferably 3 to 10 ring carbon atoms) for $L_1$, $L_2$, $L_3$, $L_4$, $L_{11}$, $L_{21}$, $L_{31}$, $L_{41}$, $L_{12}$, $L_{22}$, $L_{32}$, and $L_{42}$ include divalent groups which are derived from the cycloalkyl groups mentioned above by removing one hydrogen atom.

Examples of the substituted or unsubstituted arylene group having 6 to 30 ring carbon atoms for $L_1$, $L_2$, $L_3$, $L_4$, $L_{11}$, $L_{21}$, $L_{31}$, $L_{41}$, $L_{12}$, $L_{22}$, $L_{32}$, $L_{11a}$, $L_{21a}$, $L_{31a}$, $L_{41a}$, $L_{12a}$, $L_{22a}$, $L_{32a}$, $L_{42a}$, and $L_{42}$ include divalent groups which are derived from the aryl groups mentioned above by removing one hydrogen atom.

Examples of the substituted or unsubstituted heteroarylene group having 5 to 30 ring atoms for $L_1$, $L_2$, $L_3$, $L_4$, $L_{11}$, $L_{21}$, $L_{31}$, $L_{41}$, $L_{12}$, $L_{22}$, $L_{32}$, $L_{11a}$, $L_{21a}$, $L_{31a}$, $L_{41a}$, $L_{12a}$, $L_{22a}$, $L_{32a}$, $L_{42a}$, and $L_{42}$ include divalent residues which are derived from the heteroaryl groups mentioned above by removing one hydrogen atom.

In formulae (1), (1-1), (1-2), (1-1a), and (1-2a), the arylene group for $L_1$, $L_2$, $L_3$, $L_4$, $L_{11}$, $L_{21}$, $L_{31}$, $L_{41}$, $L_{12}$, $L_{22}$, $L_{32}$, $L_{11a}$, $L_{21a}$, $L_{31a}$, $L_{41a}$, $L_{12a}$, $L_{22a}$, $L_{32a}$, $L_{42a}$, and $L_{42}$ is preferably a substituted or unsubstituted phenylene group or a polycyclic aromatic group selected from a substituted or unsubstituted anthracenylene group, a substituted or unsubstituted phenanthrenylene group, a substituted or unsubstituted chrysenylene group, a substituted or unsubstituted pyrenylene group, a substituted or unsubstituted acenaphthylenylene group, a substituted or unsubstituted acenaphthenylene group, a substituted or unsubstituted fluoranthenylene group, a substituted or unsubstituted fluorenylene group, a substituted or unsubstituted naphthylene group, a substituted or unsubstituted benzofluoranthenylene group, a substituted or unsubstituted benzophenanthrenylene group, a substituted or unsubstituted benzochrysenylene group, a substituted or unsubstituted benzotriphenylenylene group, a substituted or unsubstituted benzanthracenylene group, a substituted or unsubstituted dibenzophenanthrenylene group, and a substituted or unsubstituted triphenylenylene group, with anthracenylene group, phenanthrenylene group, chrysenylene group, naphthylene group, triphenylenylene group, fluoranthenylene group, benzochrysenylene group, benzanthracenylene group, phenylene group, and pyrenylene group being more preferred, and anthracenylene group being particularly preferred.

The above arylene group for $L_1$, $L_2$, $L_3$, $L_4$, $L_{11}$, $L_{21}$, $L_{31}$, $L_{41}$, $L_{12}$, $L_{22}$, $L_{32}$, $L_{11a}$, $L_{21a}$, $L_{31a}$, $L_{41a}$, $L_{12a}$, $L_{22a}$, $L_{32a}$, $L_{42a}$, and $L_{42}$ may be substituted.

The substituent for the arylene group includes, for example, a halogen atom, a hydroxyl group, a substituted or unsubstituted amino group, a nitro group, a cyano group, a substituted or unsubstituted alkyl group, a substituted or unsubstituted alkenyl group, a substituted or unsubstituted cycloalkyl group, a substituted or unsubstituted alkoxy group, a substituted or unsubstituted aryl group, a substituted or unsubstituted heteroaryl group, a substituted or unsubstituted aralkyl group, a substituted or unsubstituted aryloxy group, a substituted or unsubstituted alkylsilyl group, a substituted or unsubstituted arylsilyl group, a substituted or unsubstituted alkoxycarbonyl group, and a carboxyl group. The aryl group is preferably a naphthyl group, a phenanthrenyl group, fluorenyl group, a 9,9-dimethylfluorenyl group, a chrysenyl group, a fluoranthenyl group, a pyrenyl group, a benzochrysenyl group or a triphenylenyl group.

If the arylene group has two or more substituents, the substituents may bond to each other to form a ring.

Examples of the heteroarylene group for $L_1$, $L_2$, $L_3$, $L_4$, $L_{11}$, $L_{21}$, $L_{31}$, $L_{41}$, $L_{12}$, $L_{22}$, $L_{32}$, $L_{11a}$, $L_{21a}$, $L_{31a}$, $L_{41a}$, $L_{12a}$, $L_{22a}$, $L_{32a}$, $L_{42a}$, and $L_{42}$ include divalent residues which are derived from a compound represented by formula (13) by removing two hydrogen atoms:

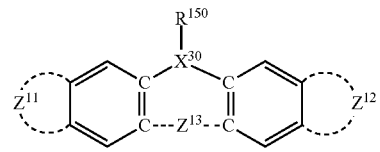

(13)

wherein $Z^{11}$ represents a substituted or unsubstituted heteroring; $Z^{12}$ represents a substituted or unsubstituted heteroring or hydrocarbon ring; $Z^{13}$ represents a divalent linking group or a single bond; $X^{30}$ represents —$NR^{150}$—, —O—, or —S—; and $R^{150}$ represents a hydrogen atom or a substituent.

Examples of the heteroring for $Z^{11}$ and $Z^{12}$ include furan ring, thiophene ring, pyridine ring, pyridazine ring, pyrimidine ring pyrazine ring, triazine ring, benzimidazole ring, oxadiazole ring, triazole ring, imidazole ring, pyrazole ring, thiazole ring, indole ring, benzimidazole ring, benzothiazole ring, benzoxazole ring, quinoxaline ring, quinazoline ring, phthalazine ring, carbazole ring, carboline ring, and carboline ring wherein the carbon atom in its hydrocarbon ring is replaced by a nitrogen atom.

Examples of the hydrocarbon ring for $Z^{12}$ in formula (13) include benzene ring, biphenyl ring, naphthalene ring, azulene ring, anthracene ring, phenanthrene ring, pyrene ring, chrysene ring, naphthacene ring, triphenylene ring, o-terphenyl ring, m-terphenyl ring, p-terphenyl ring, acenaphthene ring, coronene ring, fluorene ring, fluoranthrene ring, naphthacene ring, pentacene ring, perylene ring, pentaphene ring, picene ring, pyrene ring, pyranthrene ring, and anthraanthrene ring.

Examples of the substituent represented by $R^{150}$ of formula (13) include alkyl group, cycloalkyl group, alkenyl group, alkynyl group, aryl group, heteroring group, alkoxy group, cycloalkoxy group, aryloxy group, alkylthio group, arylthio group, alkoxycarbonyl group, aryloxycarbonyl group, sulfamoyl group, acyl group, acyloxy group, amide group, carbamoyl group, ureide group, sulfinyl group, alkylsulfonyl group, arylsulfonyl group, amino group, halogen atom, fluorohydrocarbon group, cyano group, nitro group, hydroxyl group, mercapto group, and silyl group.

These substituents may be further substituted by any of the above substituents. The substituents may be bonded to each other to form a ring.

Examples of the heteroarylene group for $L_1$, $L_2$, $L_3$, $L_4$, $L_{11}$, $L_{21}$, $L_{31}$, $L_{41}$, $L_{12}$, $L_{22}$, $L_{32}$, $L_{11a}$, $L_{21a}$, $L_{31a}$, $L_{41a}$, $L_{12a}$, $L_{22a}$, $L_{32a}$, $L_{42a}$, and $L_{42}$ includes divalent residues which are derived from the following compounds by removing two hydrogen atoms.

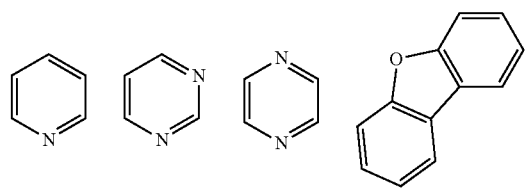

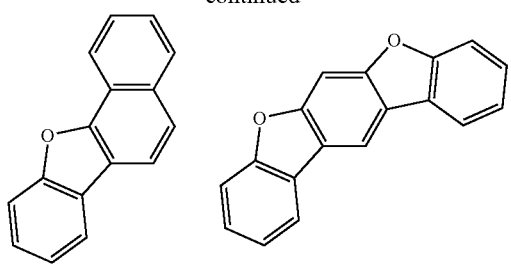
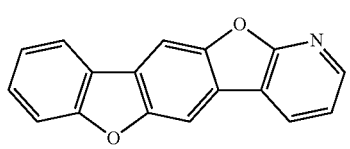
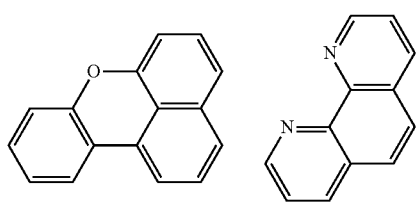
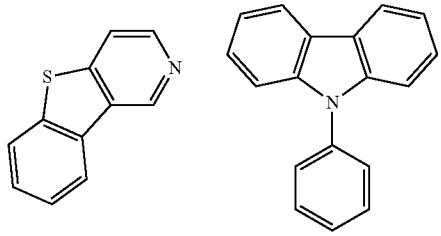
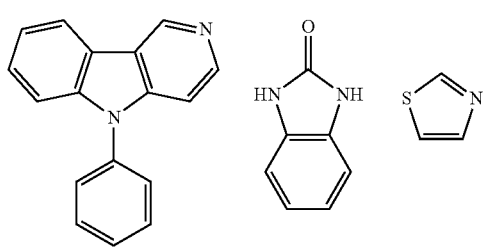
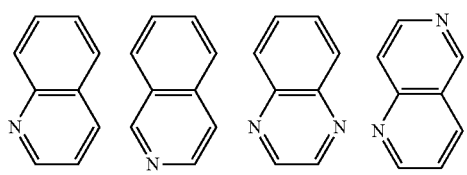
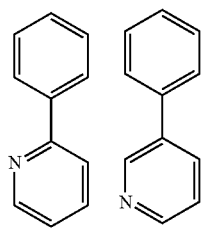

The arylene group for $L_1$, $L_2$, $L_3$, $L_4$, $L_{11}$, $L_{21}$, $L_{31}$, $L_{41}$, $L_{12}$, $L_{22}$, $L_{32}$, $L_{11a}$, $L_{21a}$, $L_{31a}$, $L_{41a}$, $L_{12a}$, $L_{22a}$, $L_{32a}$, $L_{42a}$, and $L_{42}$ is preferably represented by the following formulae:

The substituent referred to by "a substituted or unsubstituted" used herein may include a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted arylthio group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, an amino group substituted by a substituted or unsubstituted alkyl group having 1 to 50 ring carbon atoms, a substituted or unsubstituted haloalkyl group having 1 to 50 carbon atoms, an amino group substituted by a substituted or unsubstituted aryl group having 6 to 50 ring carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted alkyl group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, and a carboxyl group.

The present invention further provides a nitrogen-containing heterocyclic derivative represented by formula (1-1) or (1-2):

$$A_{11}(-L_{11}-L_{21}-L_{31}-L_{41}-Ar_{11})_p \qquad (1\text{-}1)$$

wherein:

each of $L_{11}$, $L_{21}$, $L_{31}$, and $L_{41}$ independently represents a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$Ar_{11}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms;

$A_{11}$ represents a p-valent residue of a ring-containing compound represented by formula (2-1); and p represents an integer of 1 or more;

provided that at least one of $L_{11}$, $L_{21}$, $L_{31}$, and $L_{41}$ represents a group selected from the group consisting of a substituted or unsubstituted anthracenylene group, a substituted or unsubstituted phenanthrenylene group, a substituted or unsubstituted chrysenylene group, a substituted or unsubstituted pyrenylene group, a substituted or unsubstituted acenaphthylenylene group, a substituted or unsubstituted acenaphthenylene group, a substituted or unsubstituted fluoranthenylene group, a substituted or unsubstituted fluorenylene group, a substituted or unsubstituted naphthylene group, a substituted or unsubstituted benzofluoranthenylene group, a substituted or unsubstituted benzophenanthrenylene group, a substituted or unsubstituted benzochrysenylene group, a substituted or unsubstituted benzotriphenylenylene group, a substituted or unsubstituted benzanthracenylene group, a substituted or unsubstituted dibenzophenanthrenylene group, and a substituted or unsubstituted triphenylenylene group; or $Ar_{11}$ represents a group selected from the group consisting of a substituted or unsubstituted anthracenyl group, a substituted or unsubstituted chrysenyl group, a substituted or unsubstituted pyrenyl group, a substituted or unsubstituted acenaphthylenyl group, a substituted or unsubstituted acenaphthenyl group, a substituted or unsubstituted fluoranthenyl group, a substituted or unsubstituted fluorenyl group, a substituted or unsubstituted naphthyl group, a substituted or unsubstituted benzofluoranthenyl group, a substituted or unsubstituted benzophenanthrenyl group, a substituted or unsubstituted benzochrysenyl group, a substituted or unsubstituted benzotriphenylenyl group, a substituted or unsubstituted benzanthracenyl group, a substituted or unsubstituted dibenzophenanthrenyl group, and a substituted or unsubstituted triphenylenyl group.

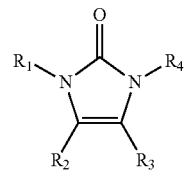

(2-1)

wherein:

each of $R_1$ to $R_4$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, an amino group substituted by a substituted or unsubstituted alkyl group having 1 to 50 ring carbon atoms, a substituted or unsubstituted haloalkyl group having 1 to 50 carbon atoms, an amino group substituted by a substituted or unsubstituted aryl group having 6 to 50 ring carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted alkyl group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{11}$; or a pair of $R_1$ and $R_2$, $R_2$ and $R_3$, or $R_3$ and $R_4$ are bonded to each other to form a ring Y represented by a substituted or unsubstituted hydrocarbon ring or a substituted or unsubstituted heteroring.

$$A_{12}(-L_{12}-L_{22}-L_{32}-L_{42}-Ar_{12})_q \qquad (1\text{-}2)$$

wherein:

each of $L_{12}$, $L_{22}$, $L_{32}$, and $L_{42}$ independently represents, a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;

$Ar_{12}$ represents a substituted or unsubstituted alkyl group having 1 to 50 carbon atoms, a substituted or unsubstituted cycloalkyl group having 3 to 50 ring carbon atoms, a substituted or unsubstituted aryl group having 6 to 30 ring carbon atoms, or a substituted or unsubstituted heteroaryl group having 5 to 30 ring atoms;

$A_{12}$ represents a q-valent residue of a ring-containing compound represented by formula (2-2), (2-3), or (2-4); and q represents an integer of 1 or more;

provided that at least one of $L_{12}$, $L_{22}$, $L_{32}$, and $L_{42}$ represents a substituted or unsubstituted arylene group having 12 to 30 carbon atoms, or $Ar_{12}$ represents a substituted or unsubstituted aryl group having 12 to 30 carbon atoms.

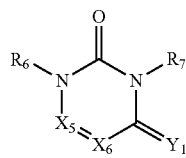

(2-2)

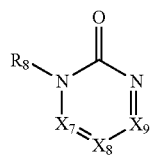

(2-3)

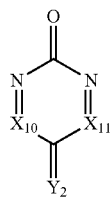

(2-4)

wherein:

each of $X_5$ to $X_{11}$ independently represents $CR_9$ or N;

each of $Y_1$ and $Y_2$ independently represents $CR_{10}R_{11}$ or $NR_{12}$;

each of $R_6$ to $R_{12}$ independently represents a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, an amino group substituted by a substituted or unsubstituted alkyl group having 1 to 50 ring carbon atoms, a substituted or unsubstituted haloalkyl group having 1 to 50 carbon atoms, an amino group substituted by a substituted or unsubstituted aryl group having 6 to 50 ring carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted alkyl group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{12}$; or $R_6$ to $R_{12}$ are each bonded to each other to form a substituted or unsubstituted hydrocarbon ring or a substituted or unsubstituted heterocyclic ring.

The details and preferred embodiments of the nitrogen-containing heterocyclic derivative of the invention are the same as those of the electron transporting material of the invention mentioned above.

Specific examples of the electron transporting materials and nitrogen-containing heterocyclic derivatives represented by formula (1), (1-1), (1-1a), (1-2), and (1-2a) are shown below, although not limited thereto.

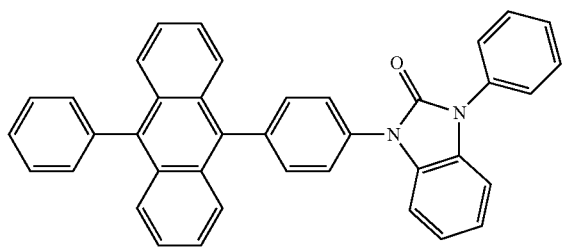

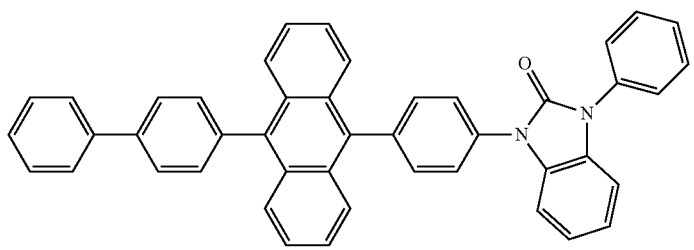
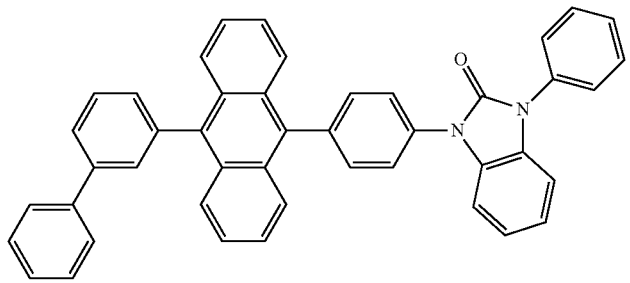
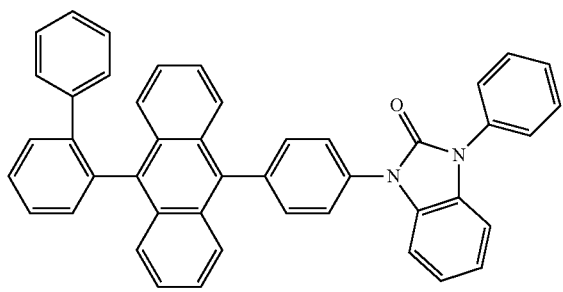
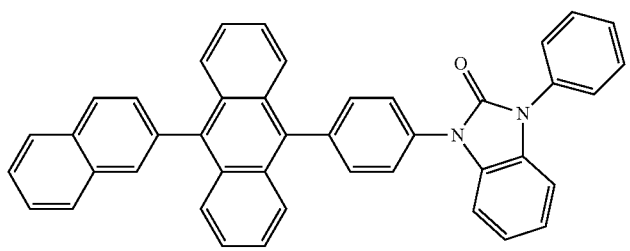
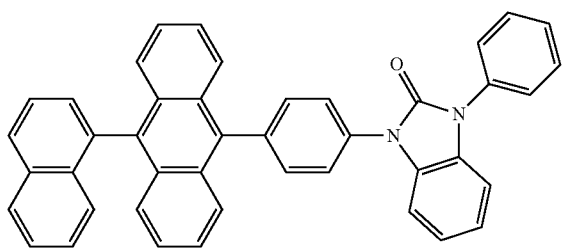
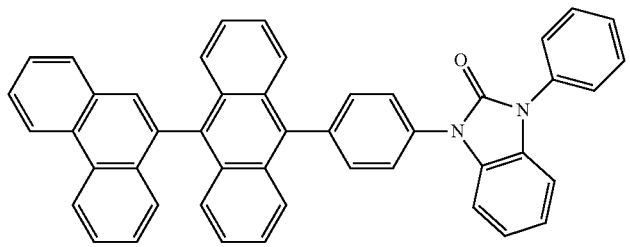

-continued
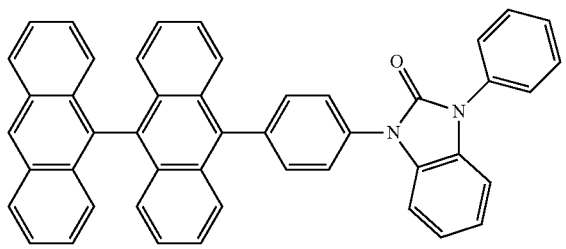
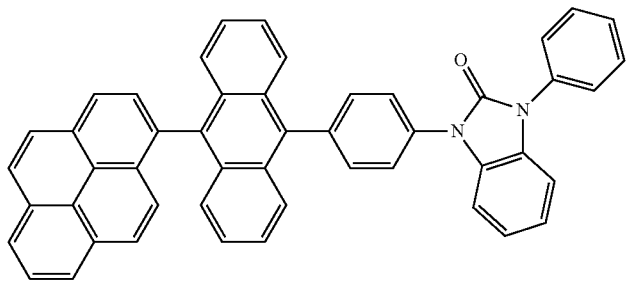
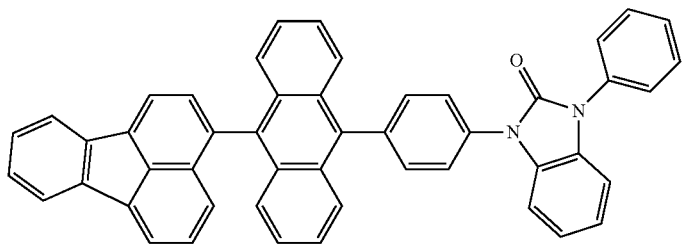
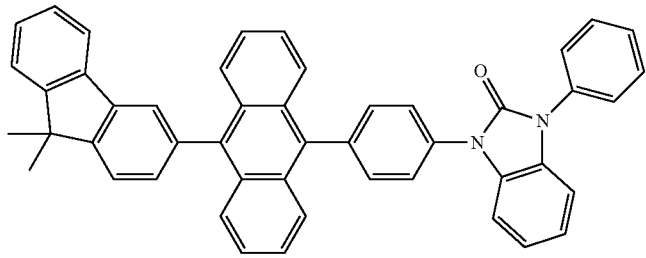
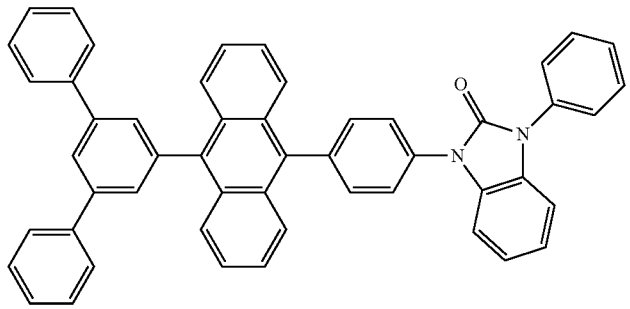
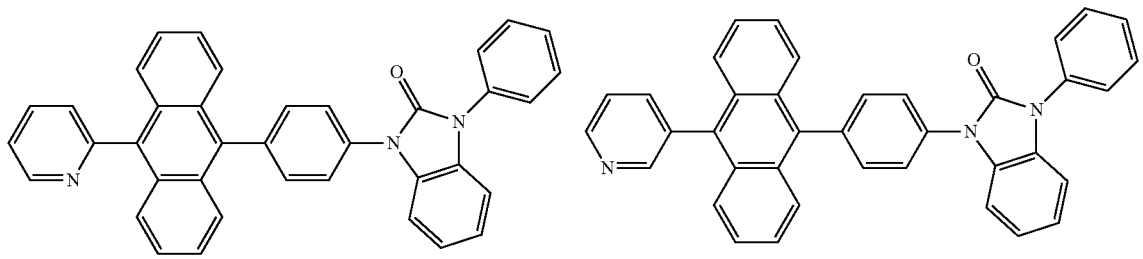

-continued
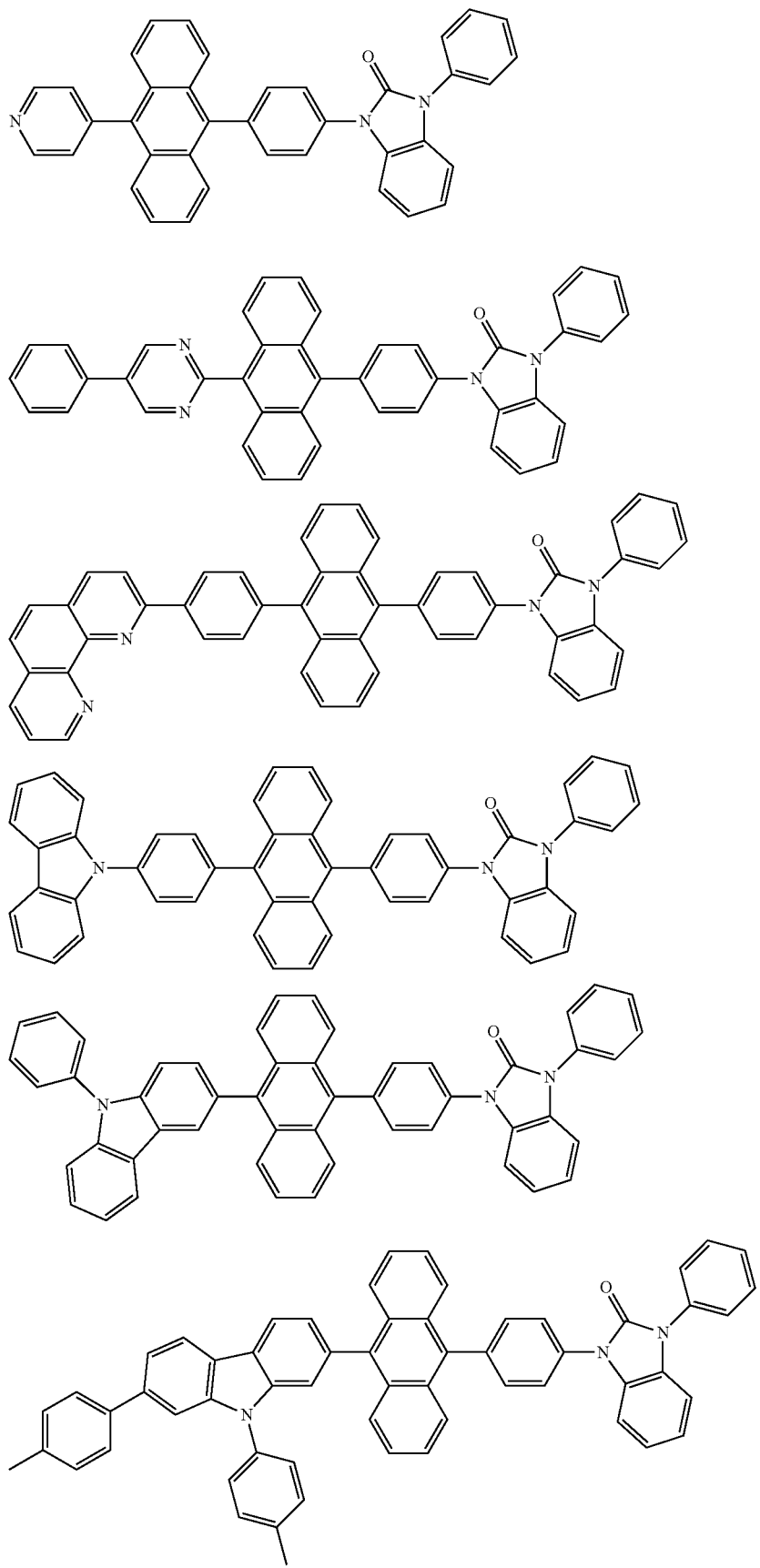

-continued
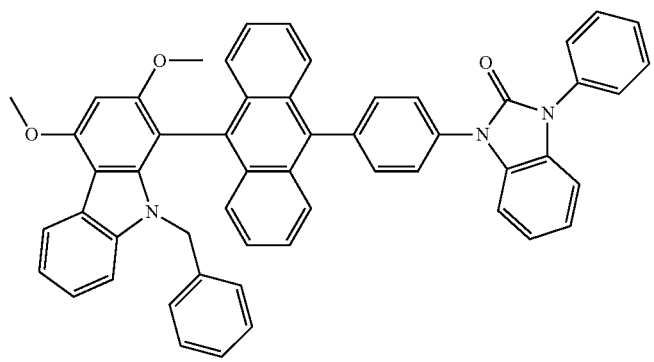
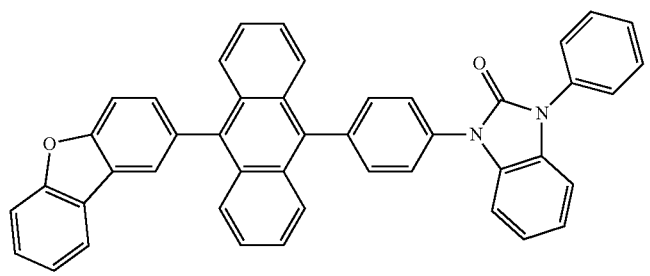
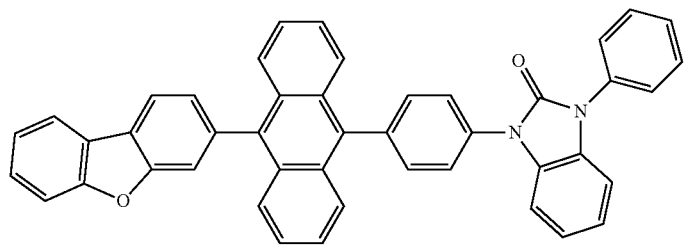
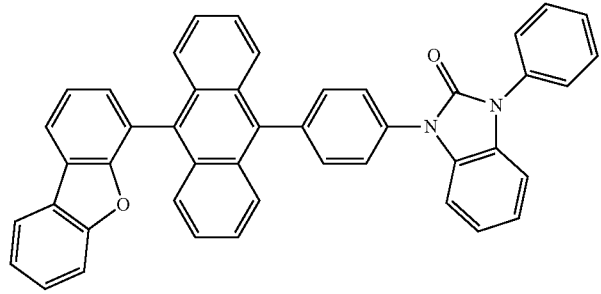
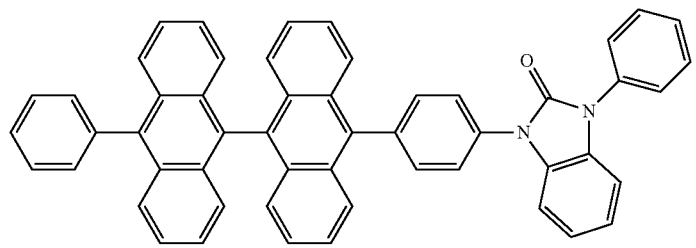
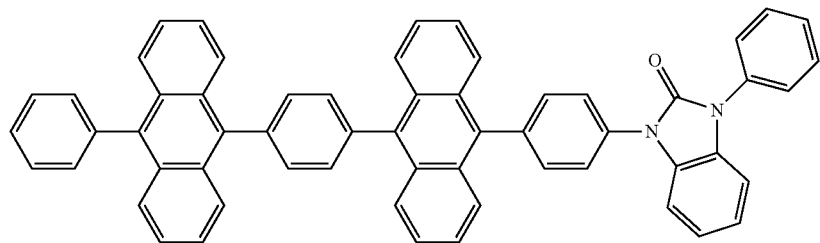

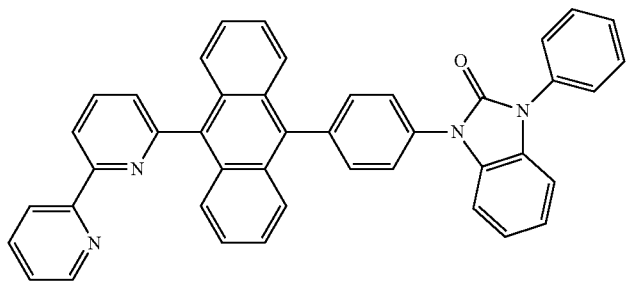
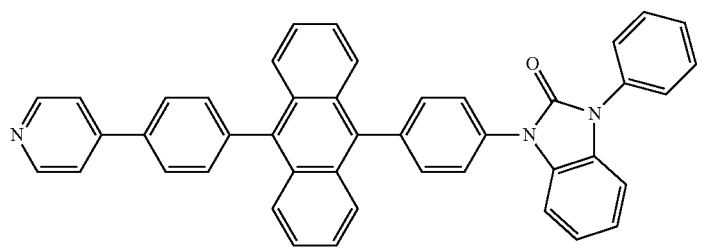
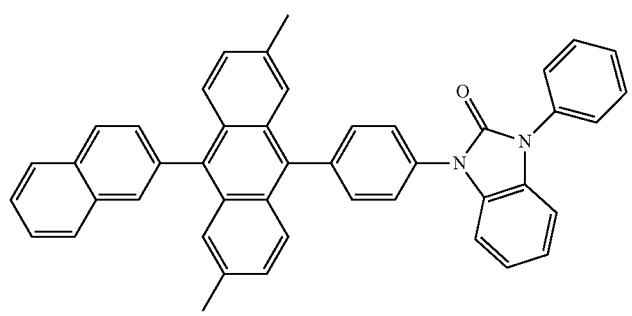
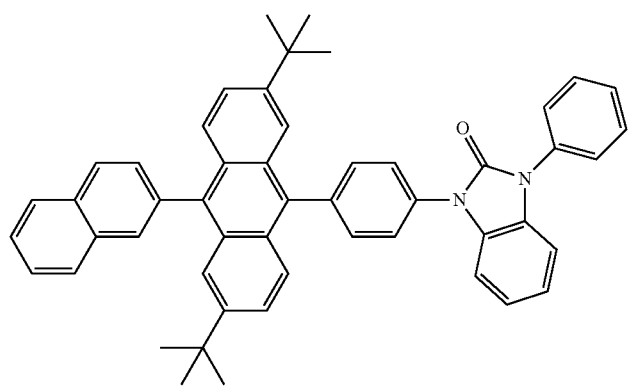
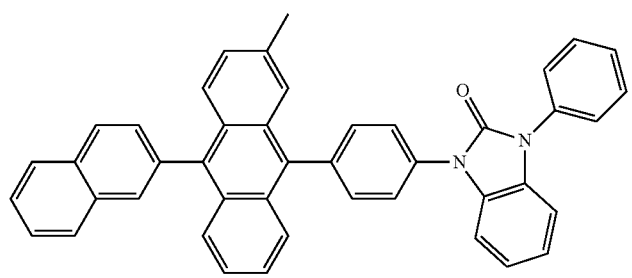

-continued
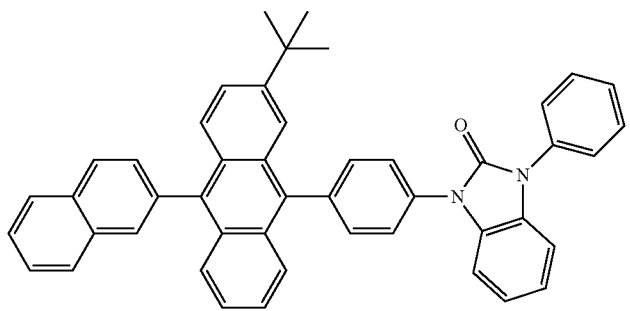
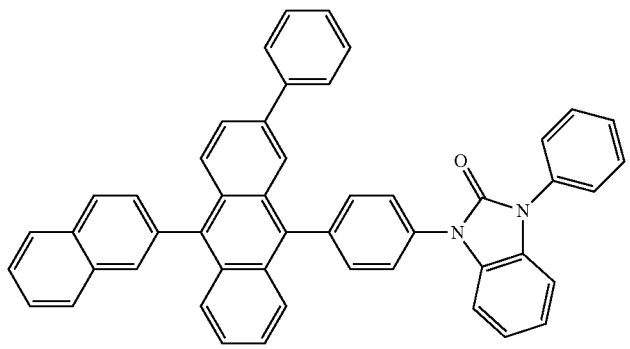
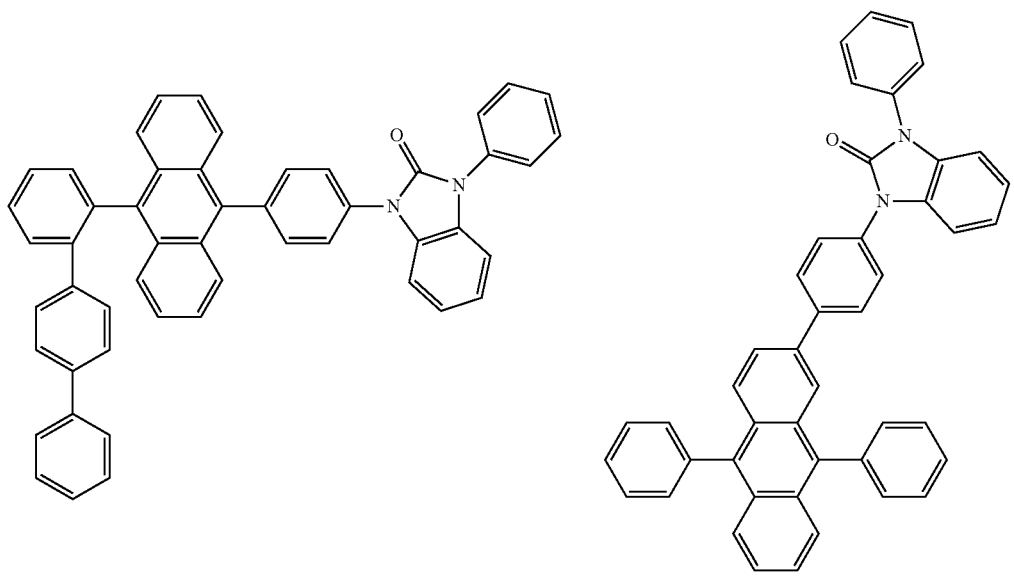

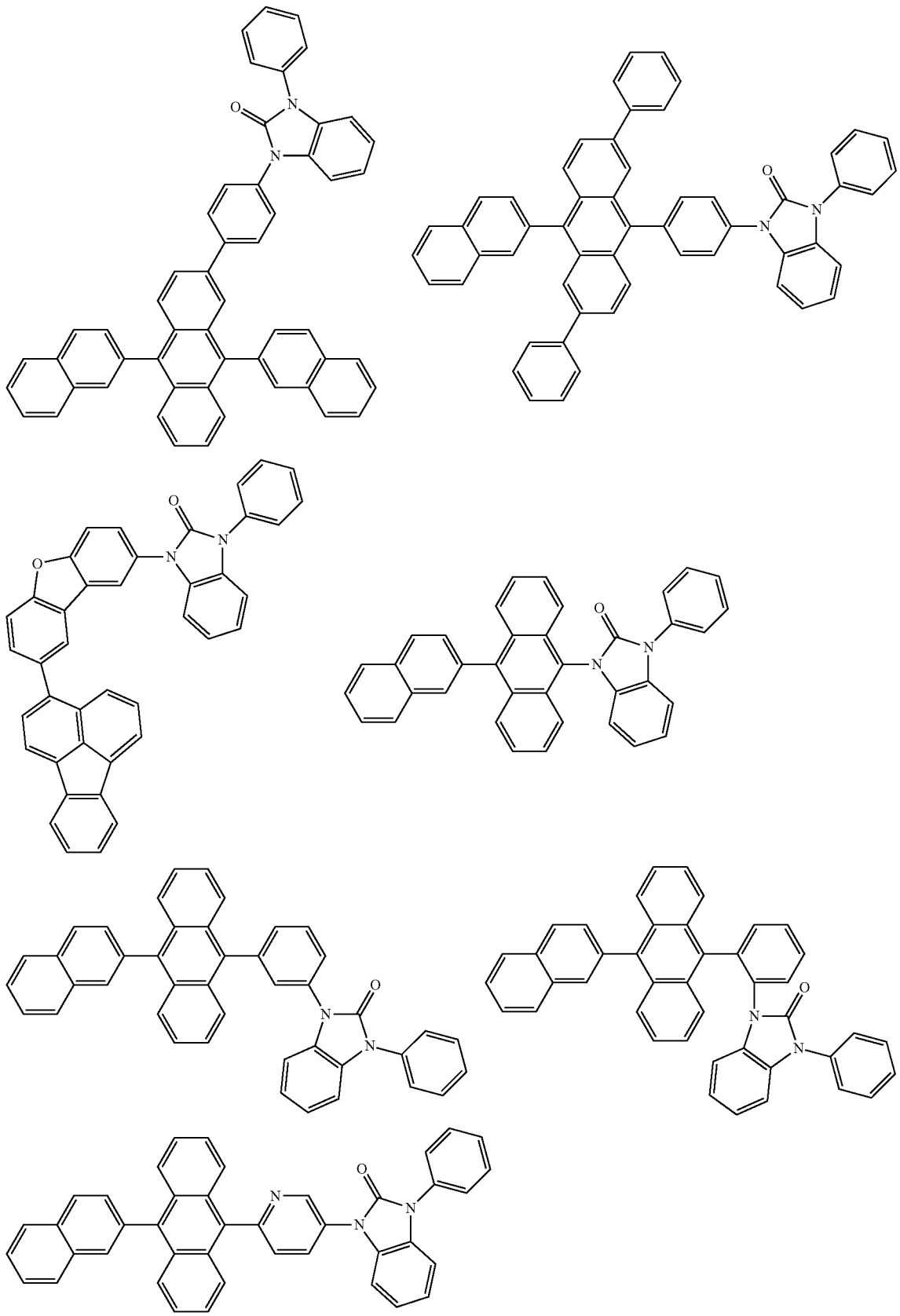

-continued
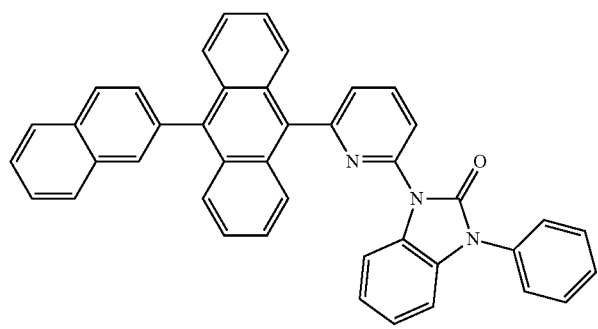
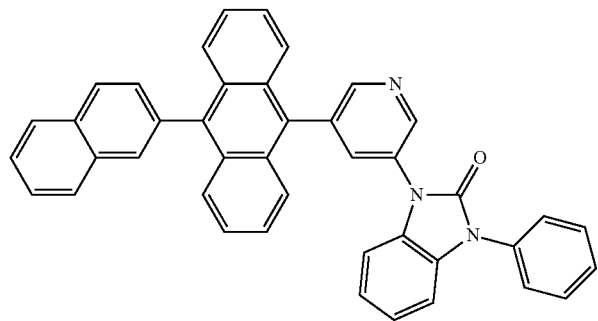
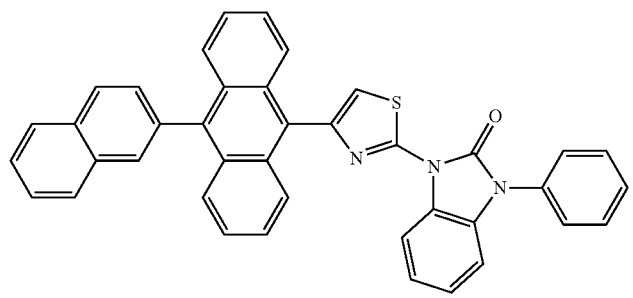
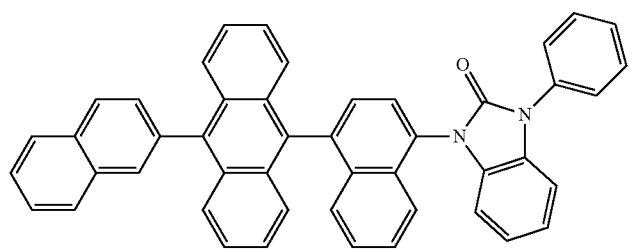
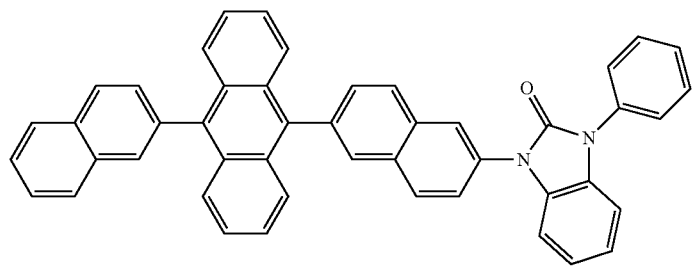
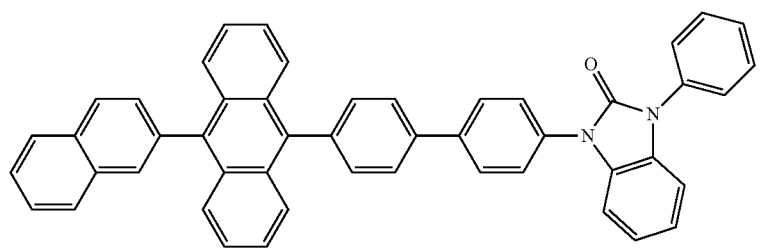

-continued
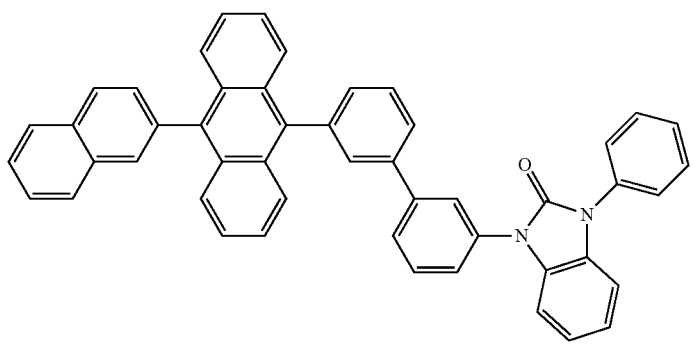
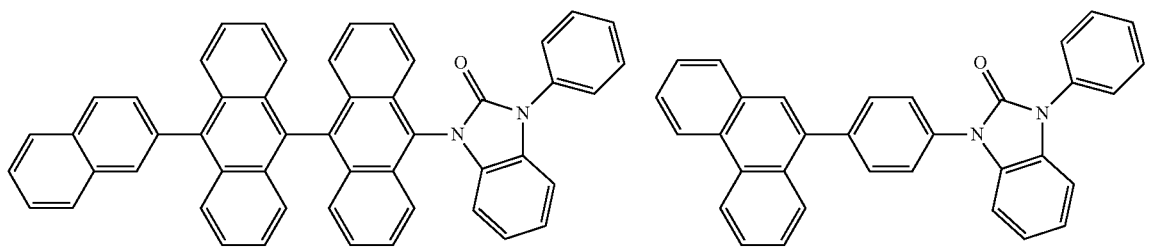
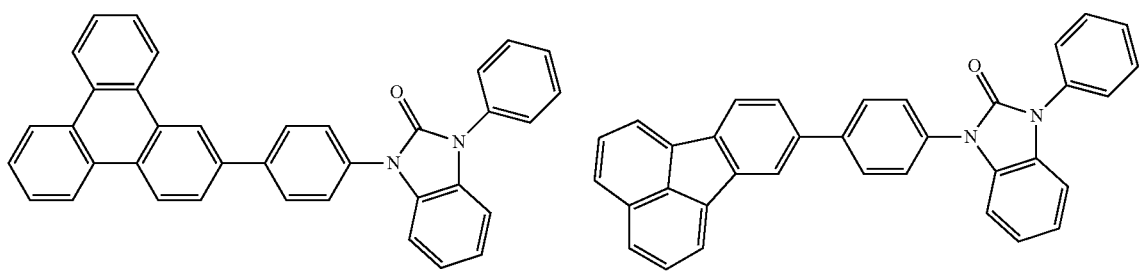
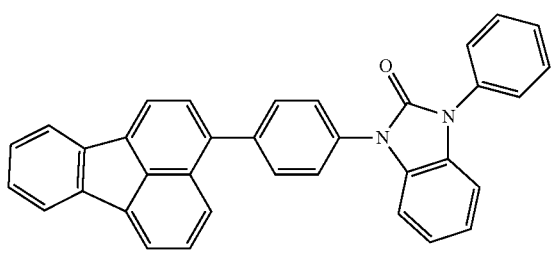
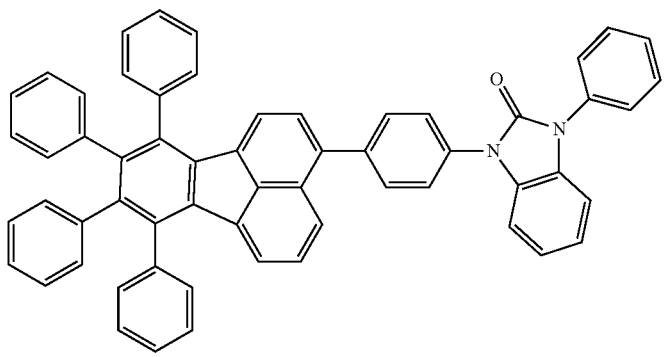

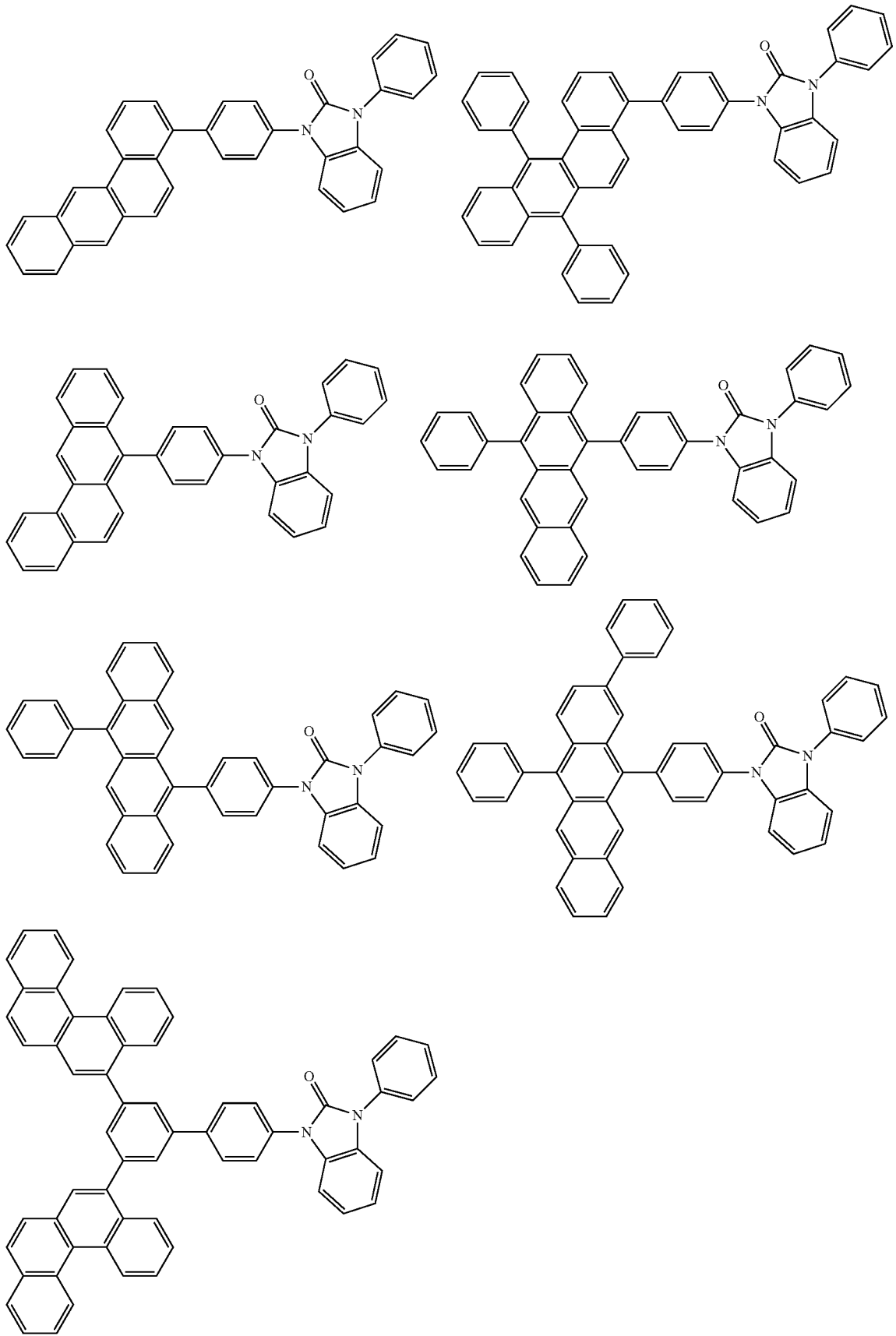

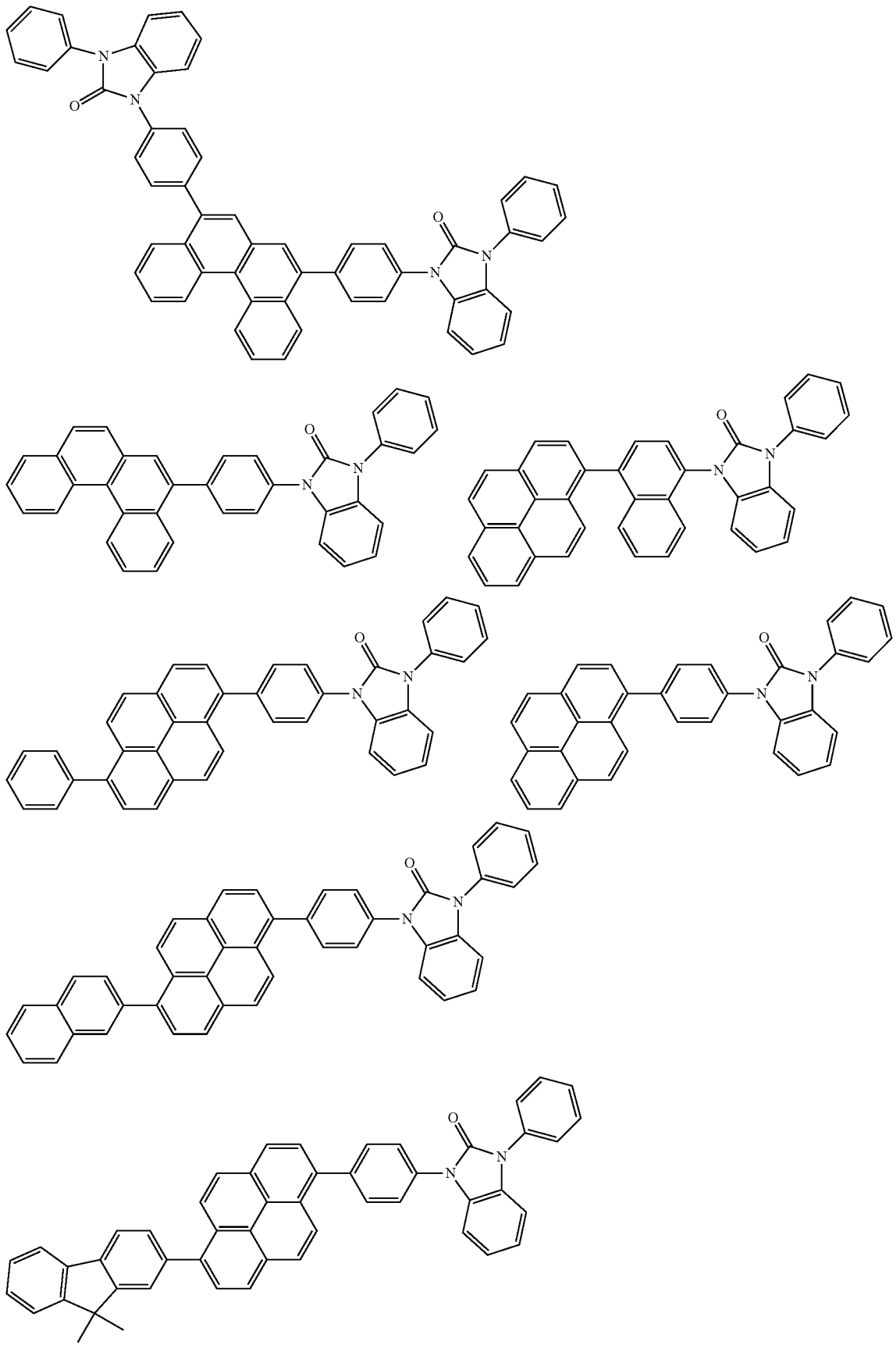

-continued
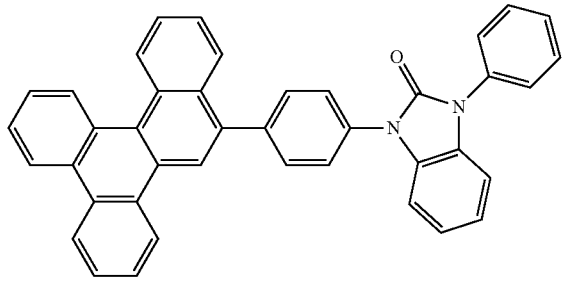
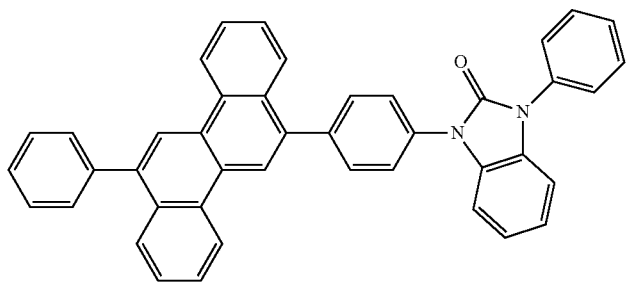
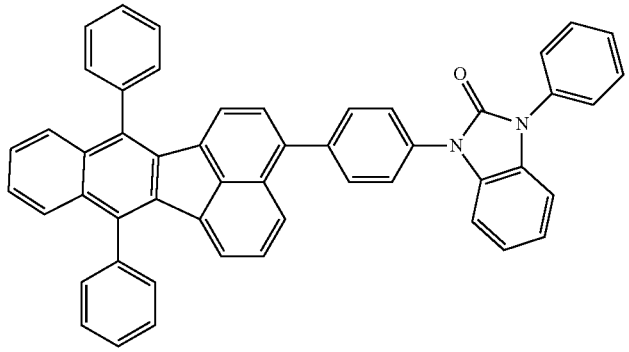
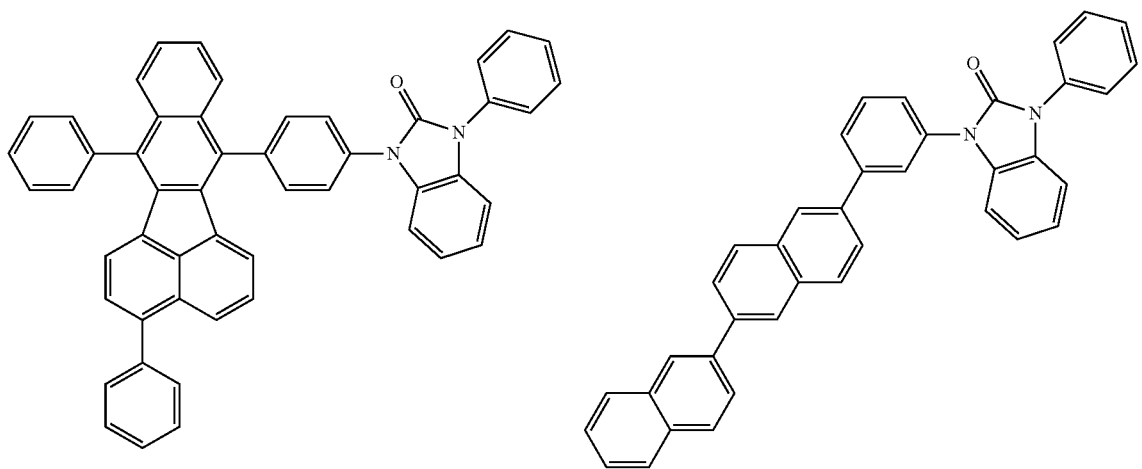

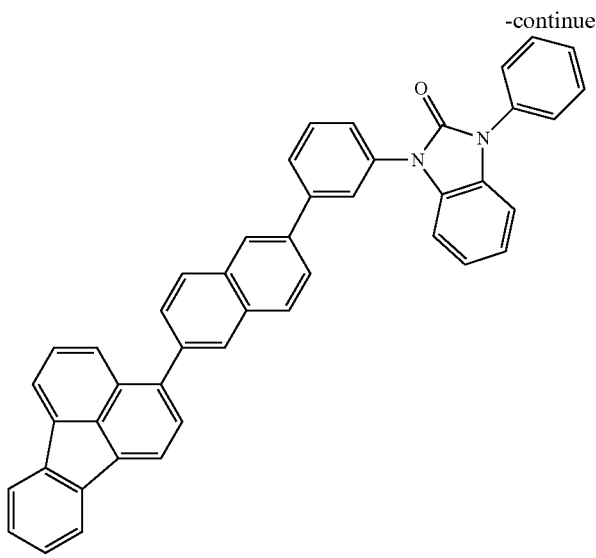
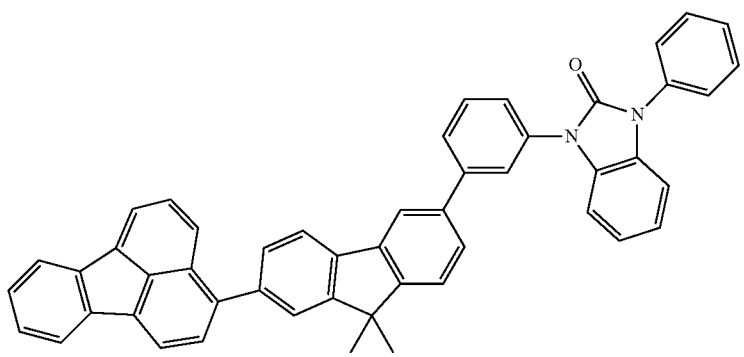
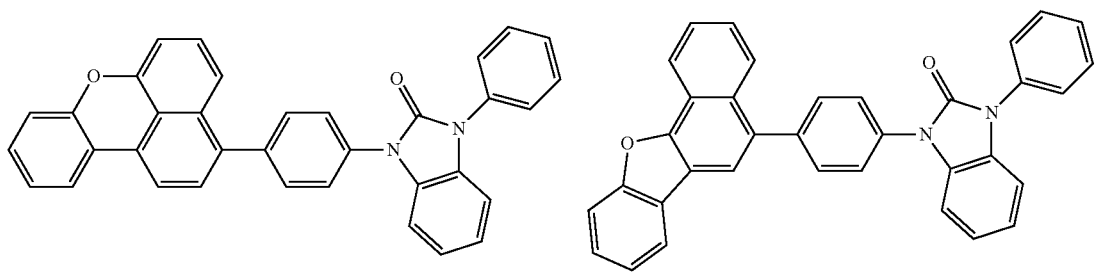
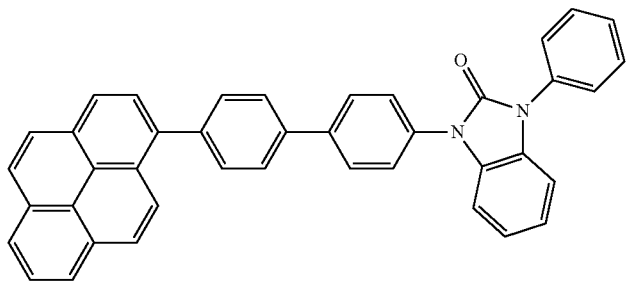

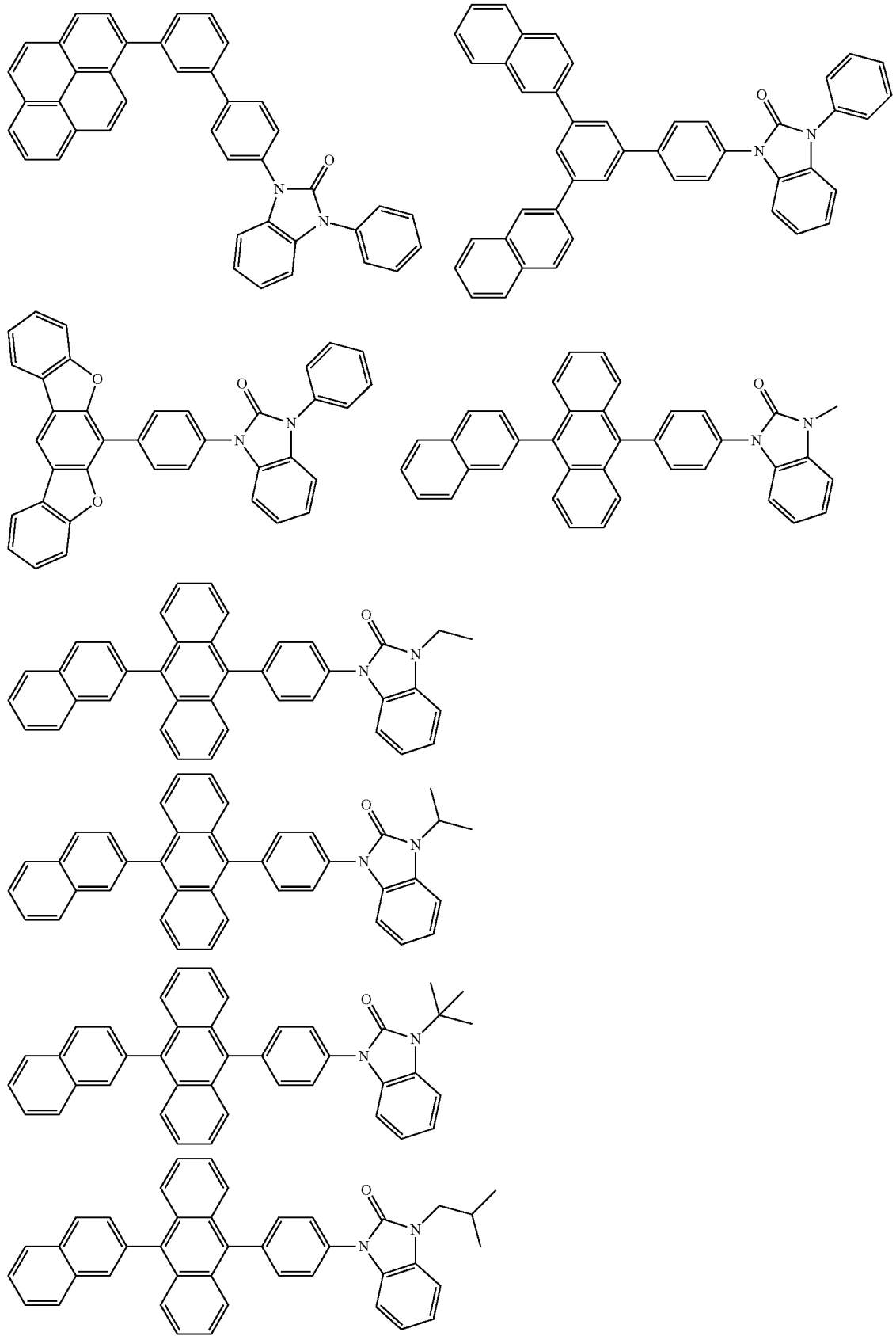

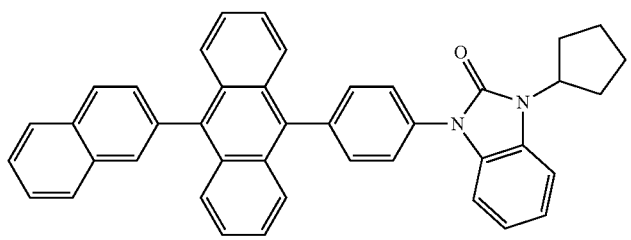
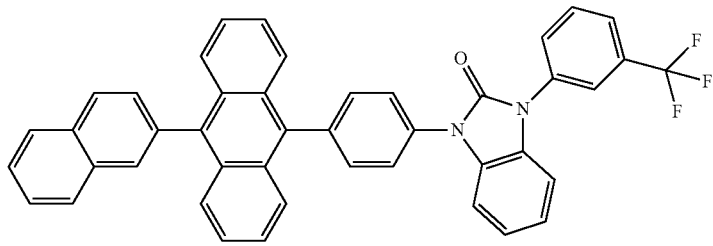
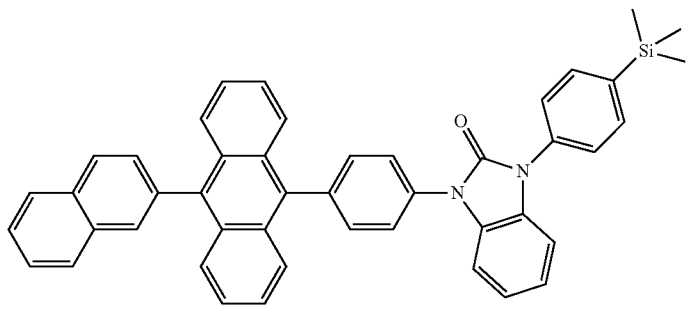
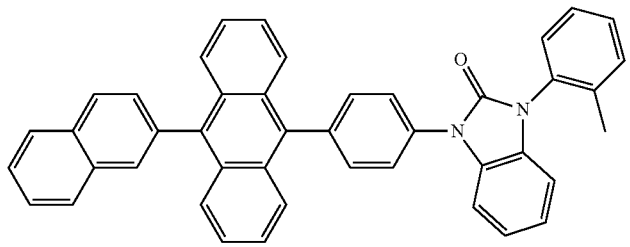
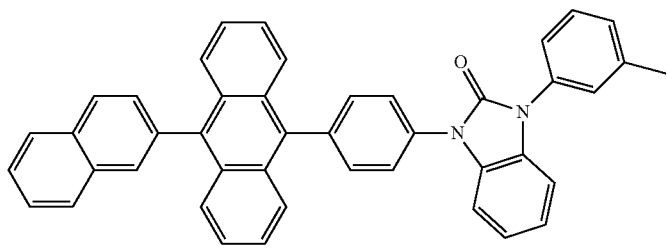
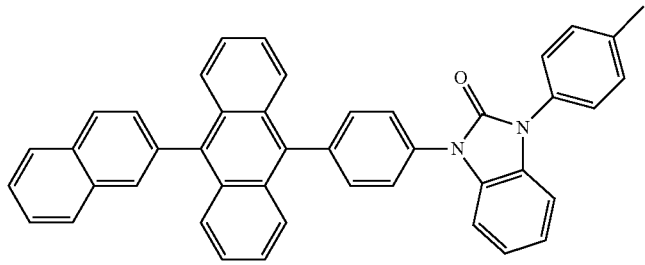

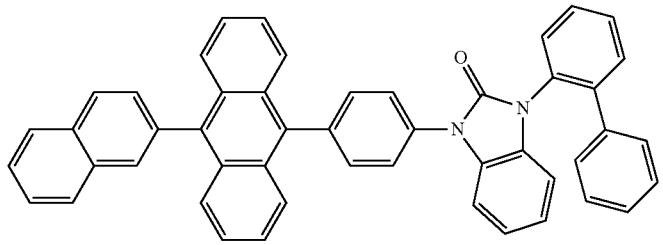
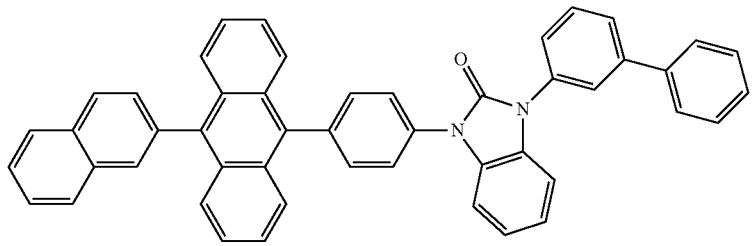
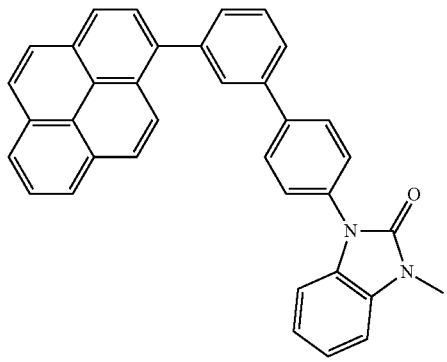
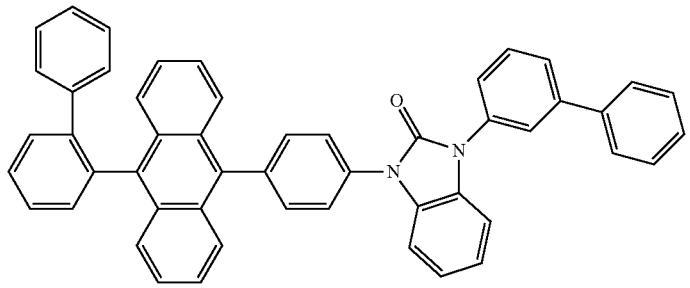
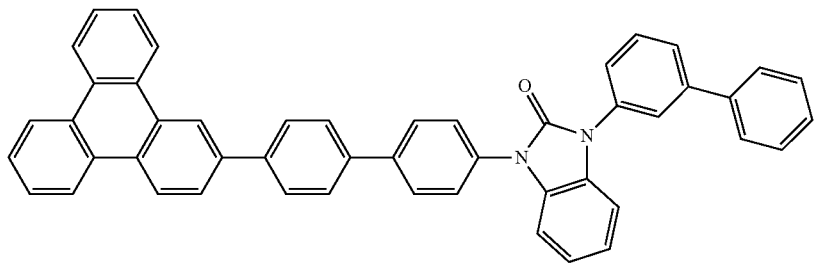
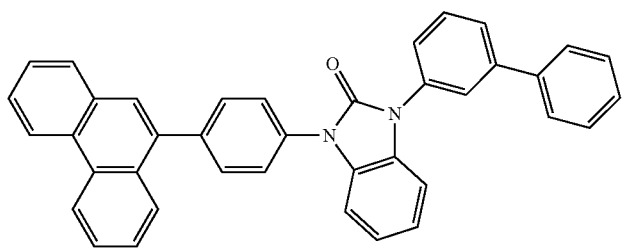

-continued
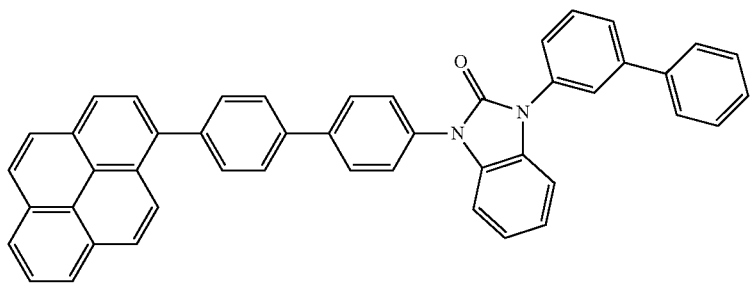
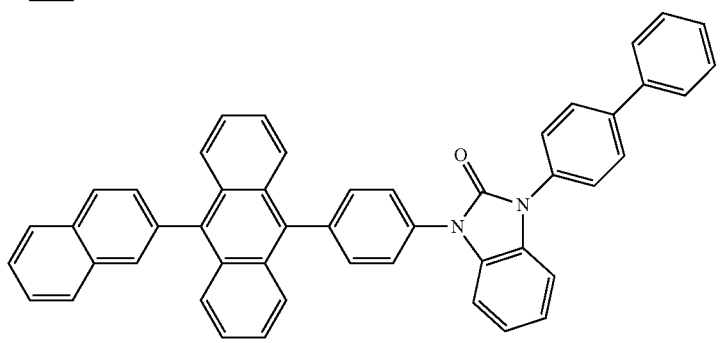
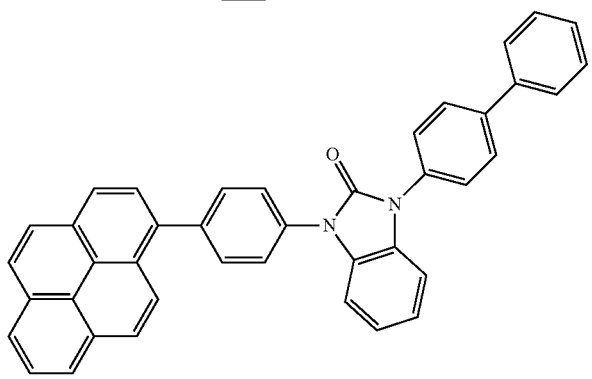
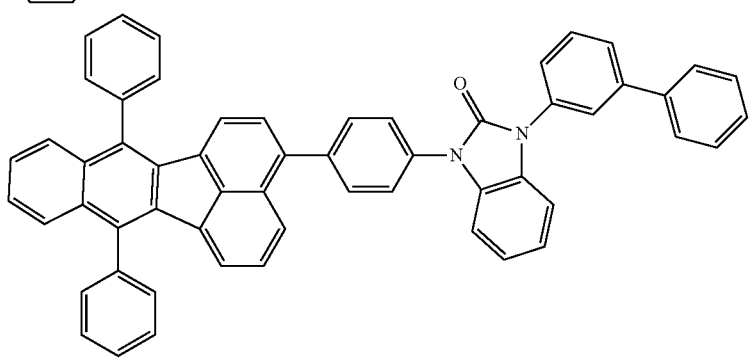
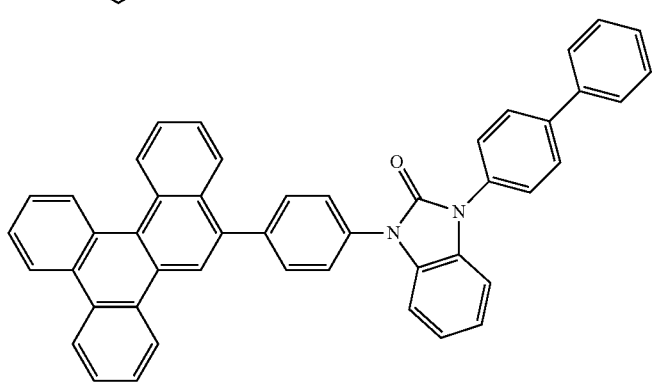

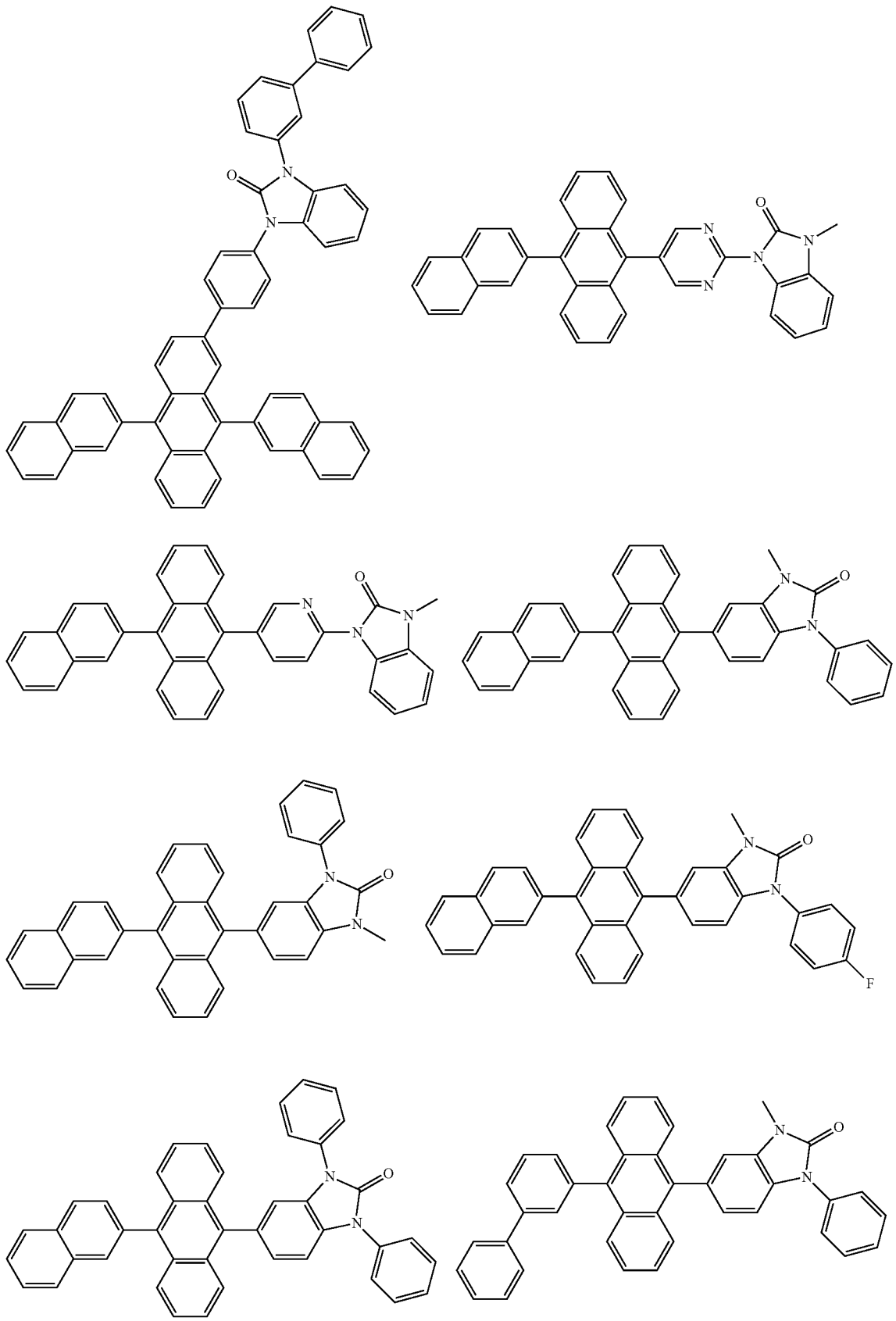

-continued
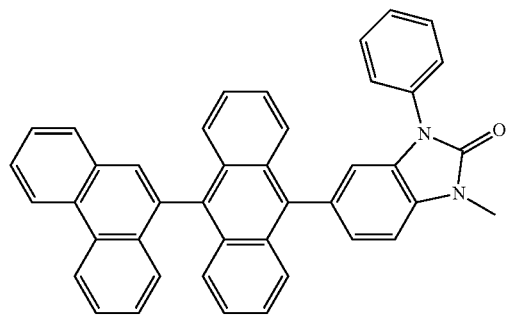
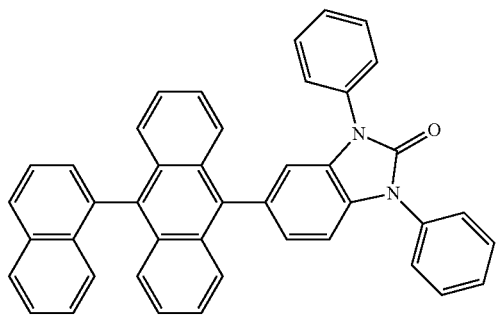
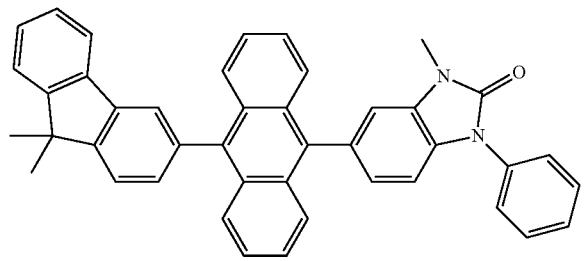
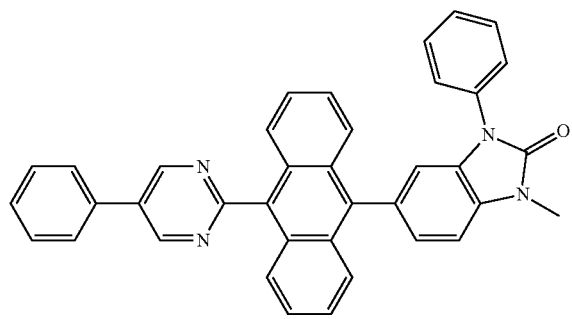
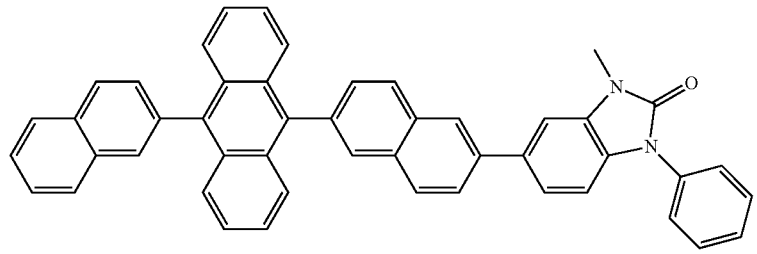
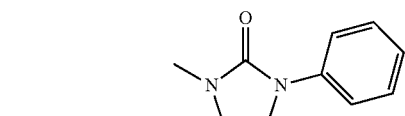
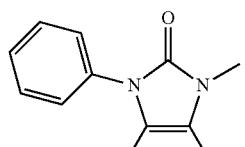
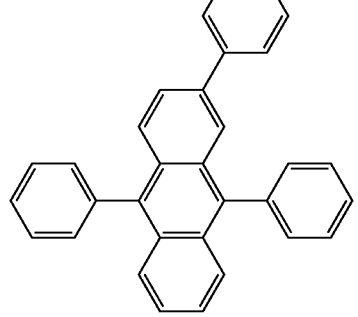
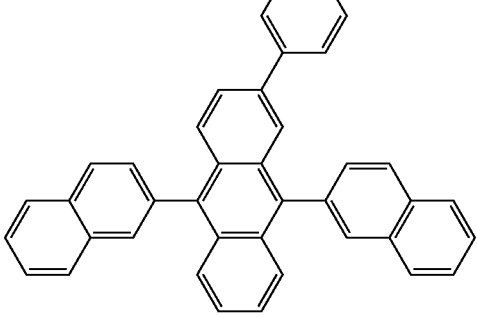

-continued
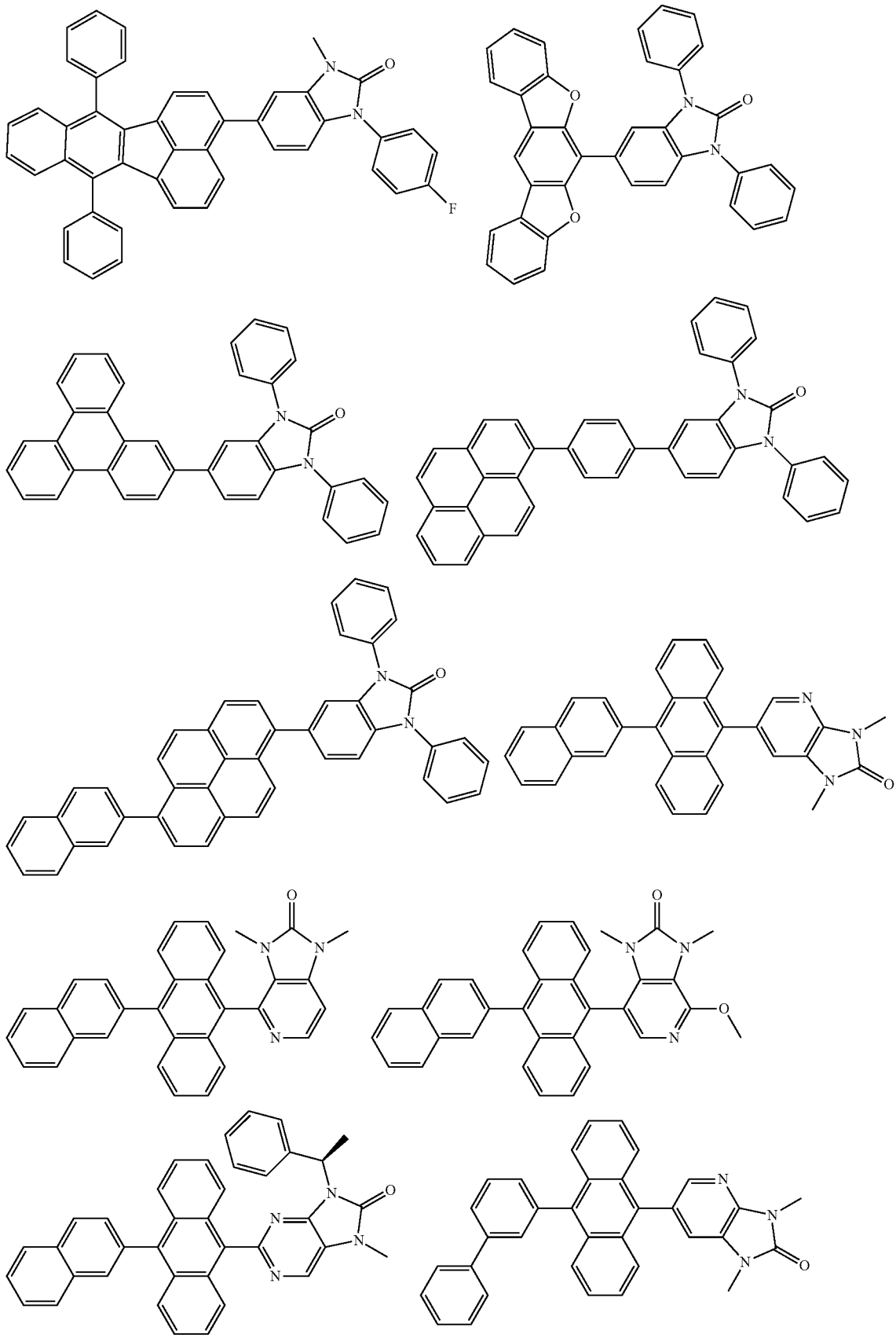

-continued
| 89 | 90 |
|---|---|
| 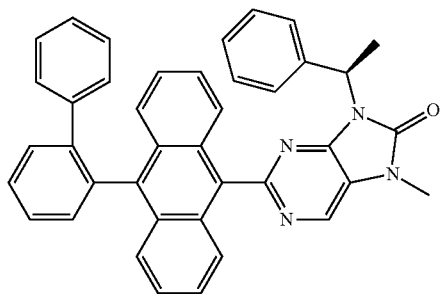 | 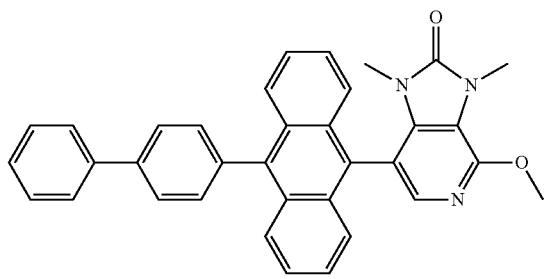 |
| 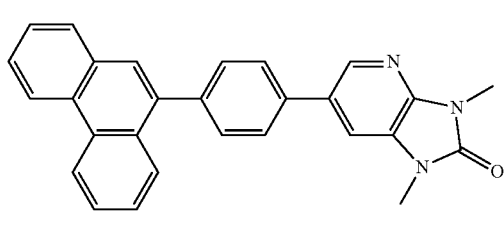 | 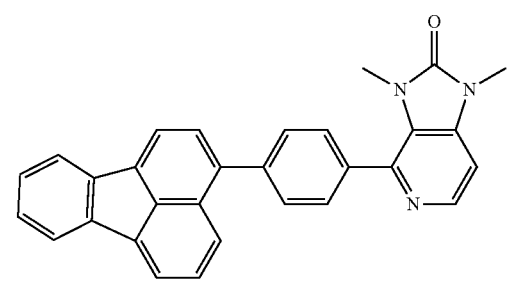 |
| 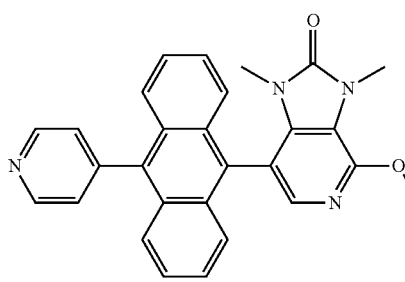 | 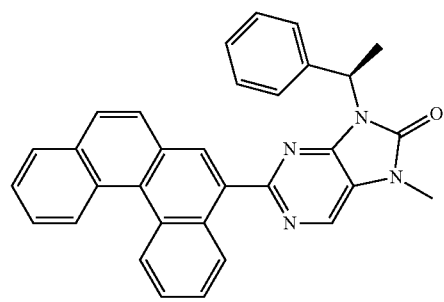 |
| 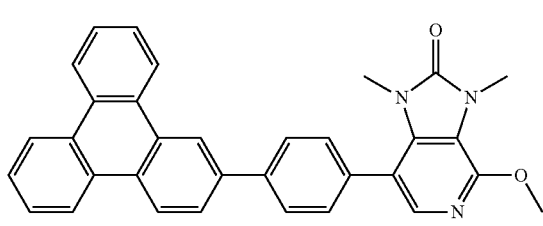 | 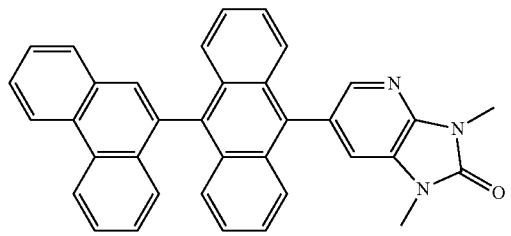 |
| 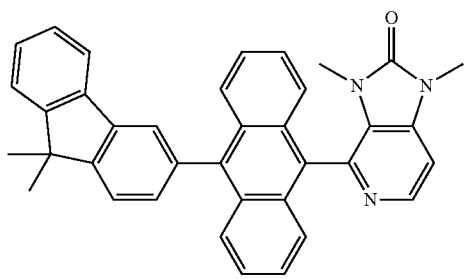 | 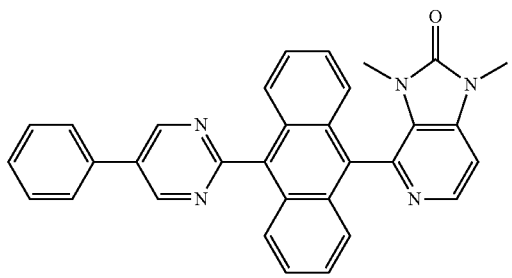 |

91 92
-continued
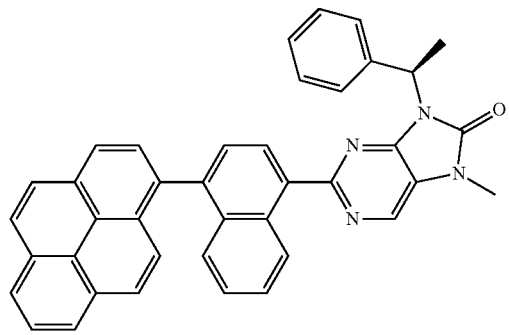 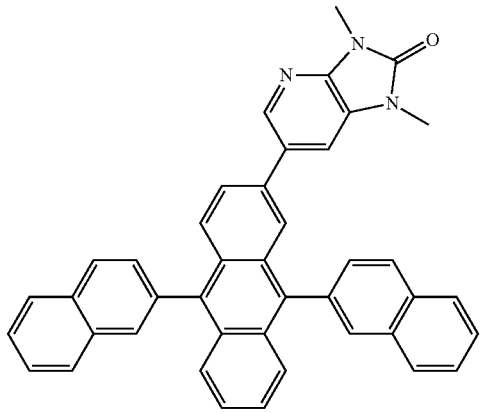
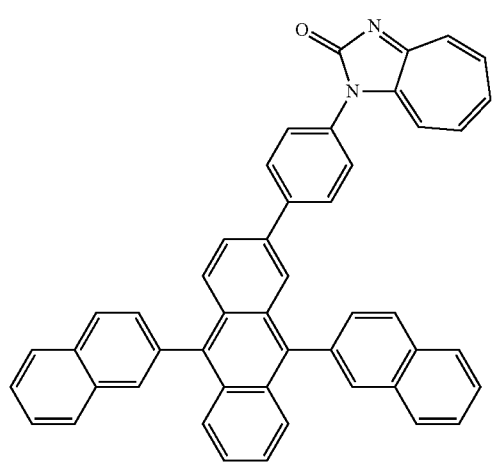 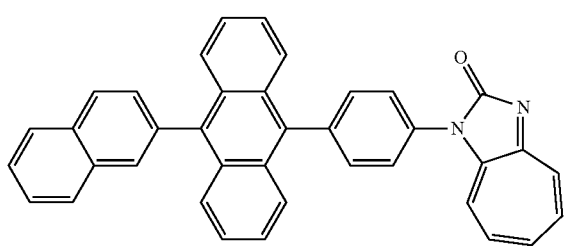
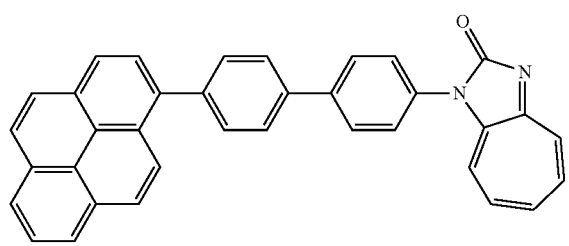 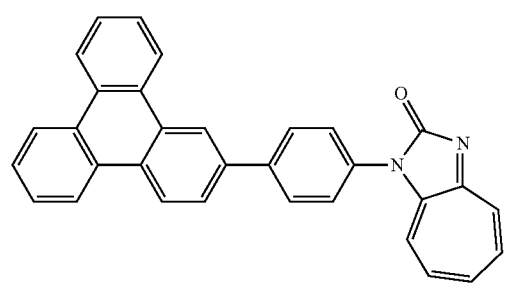
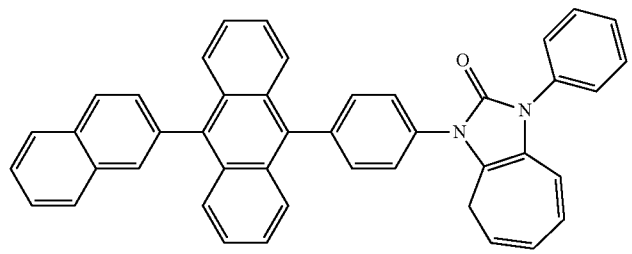
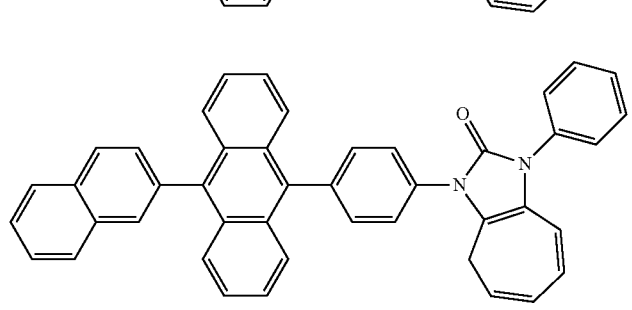 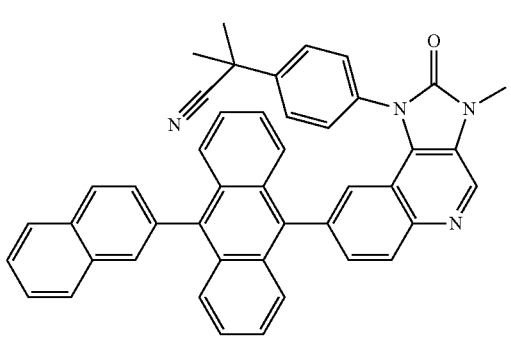

-continued
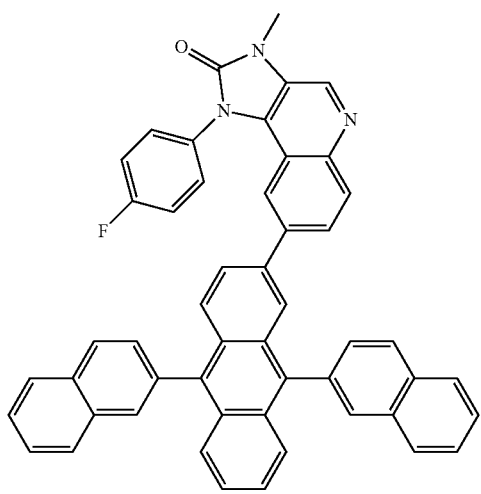
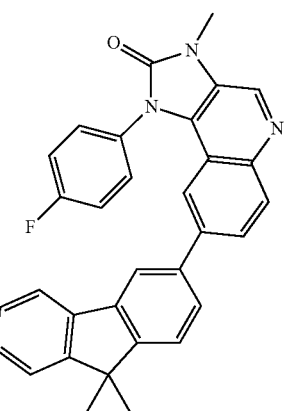
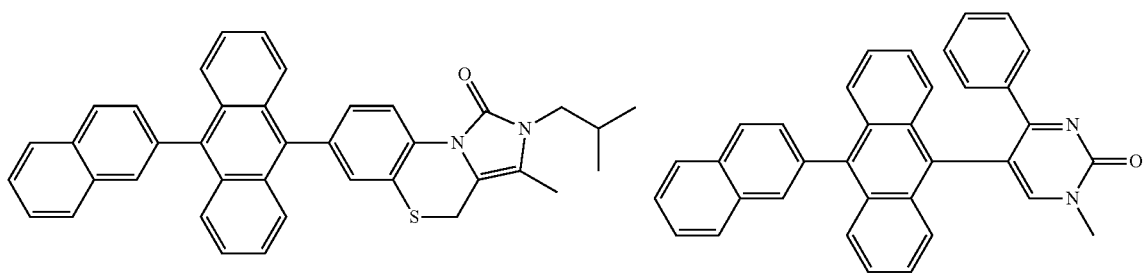
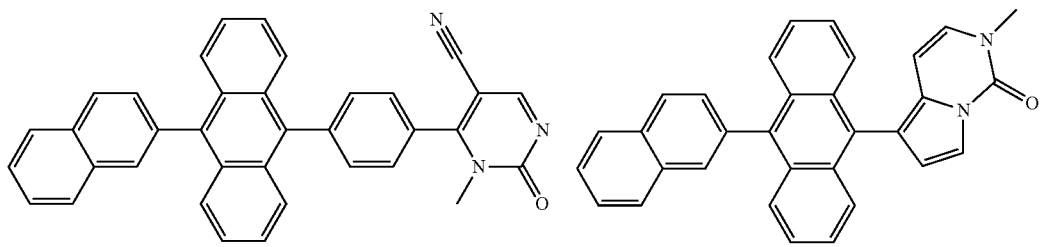
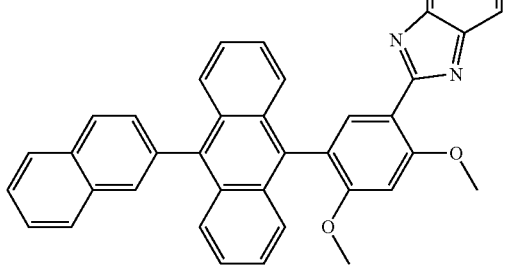

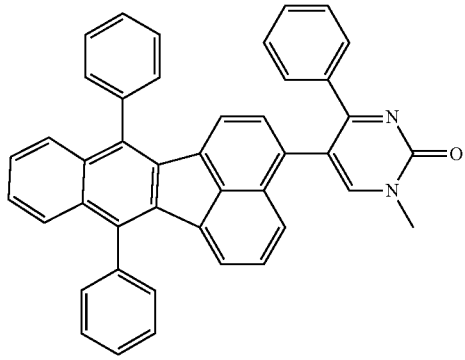
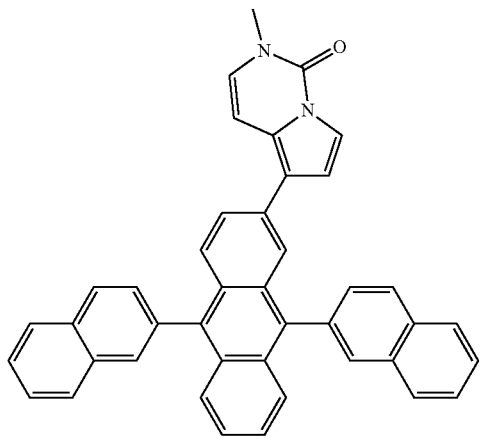
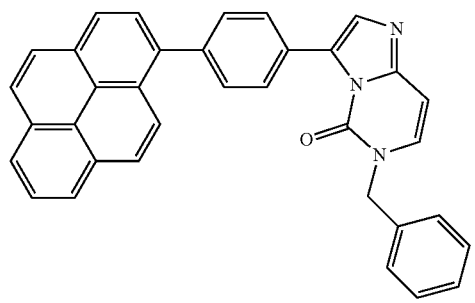
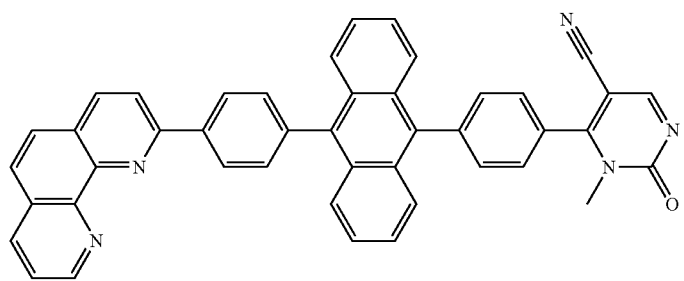
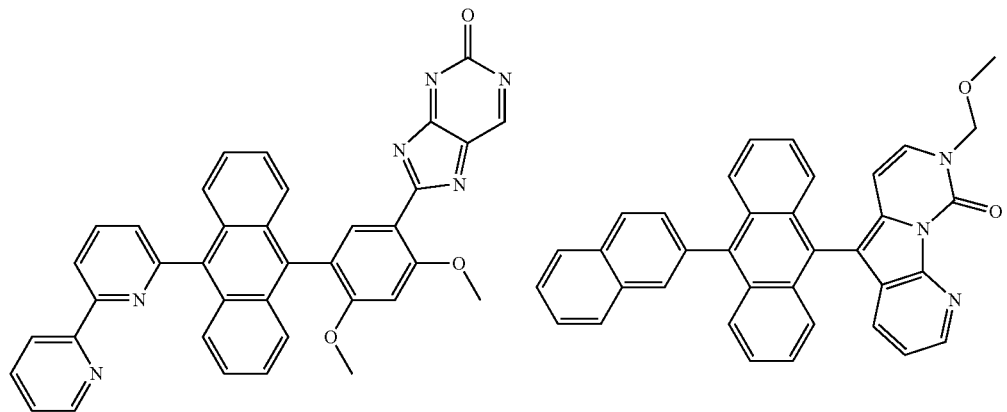

97 98
-continued
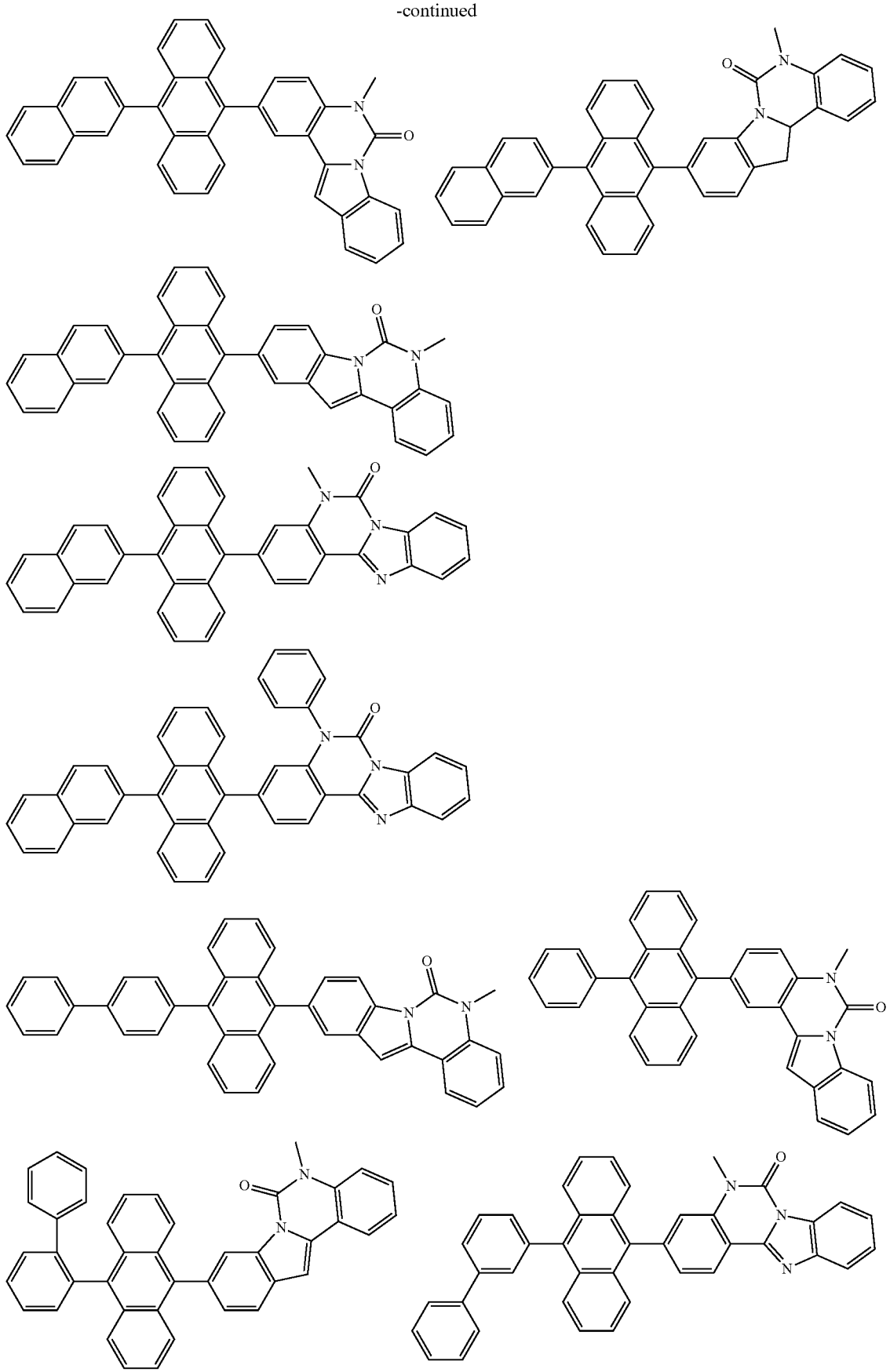

-continued
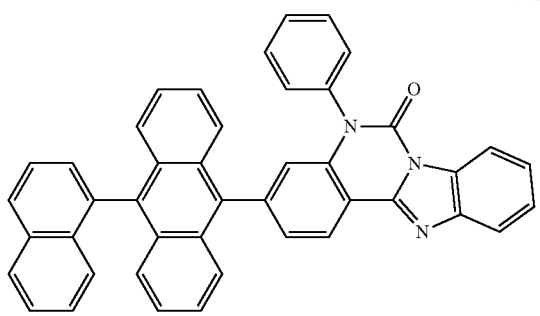
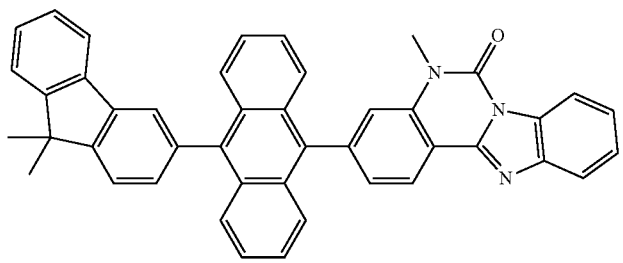
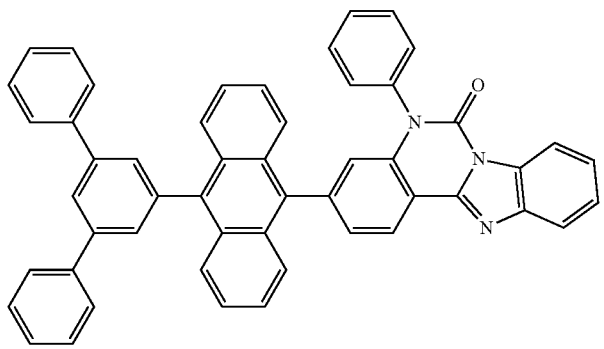
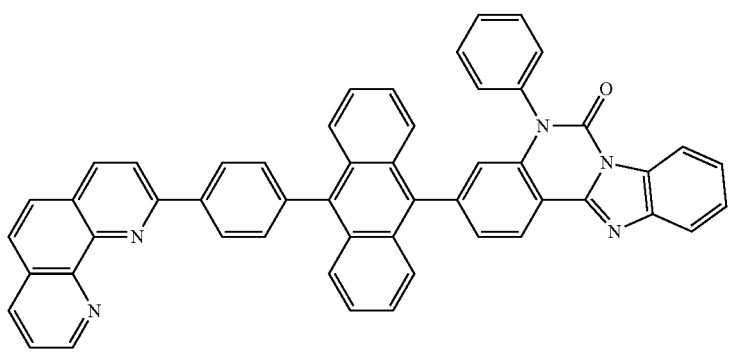
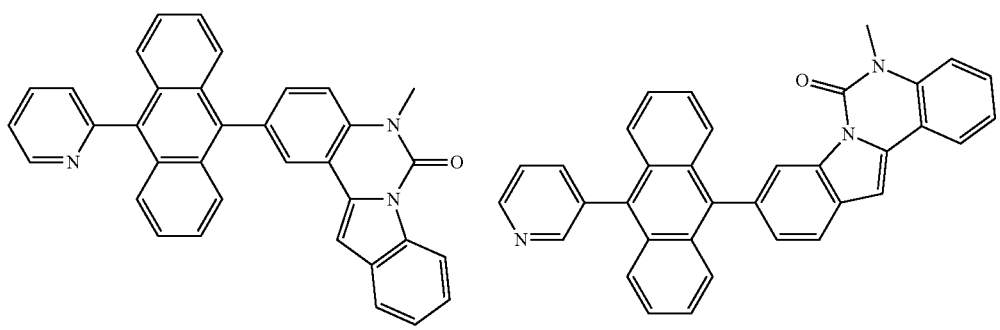

-continued
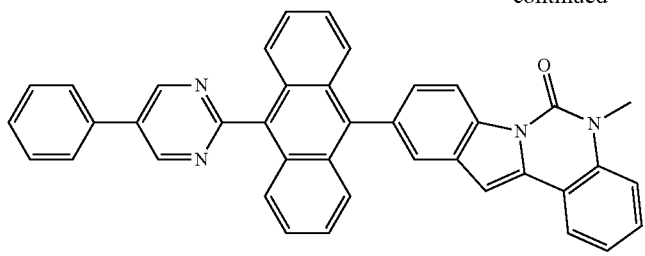
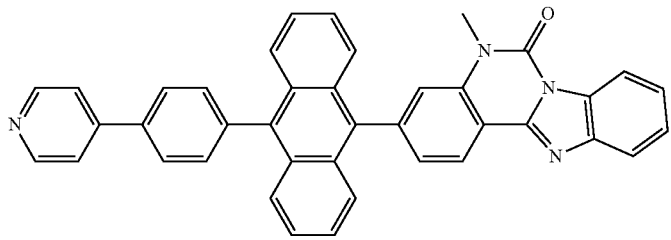
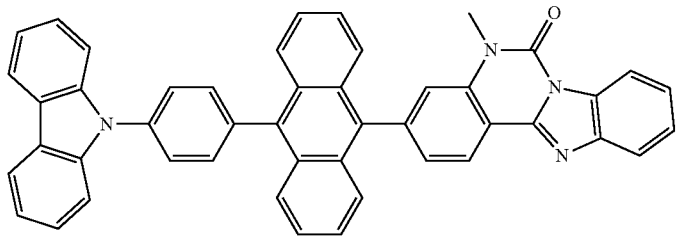
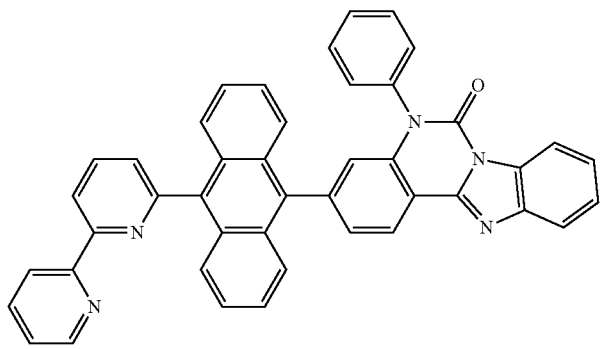
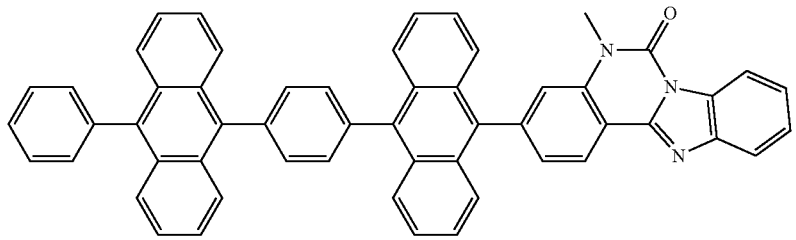
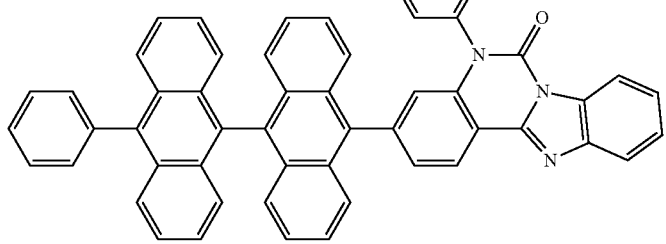

103
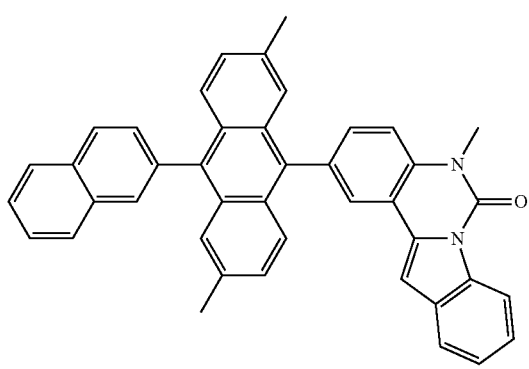
104
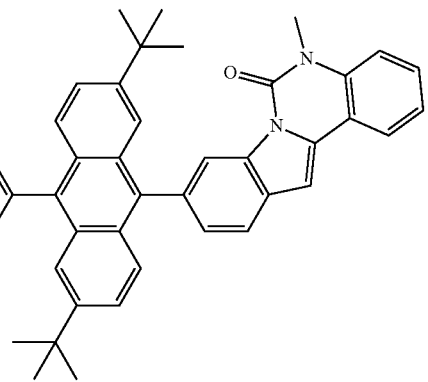
-continued
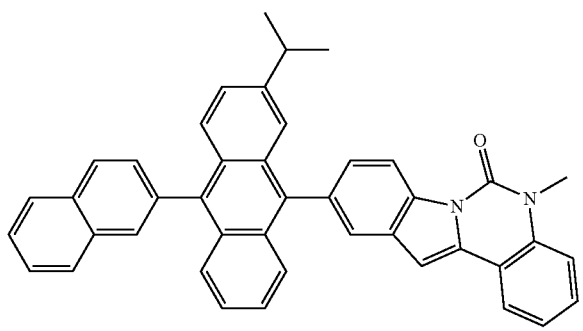
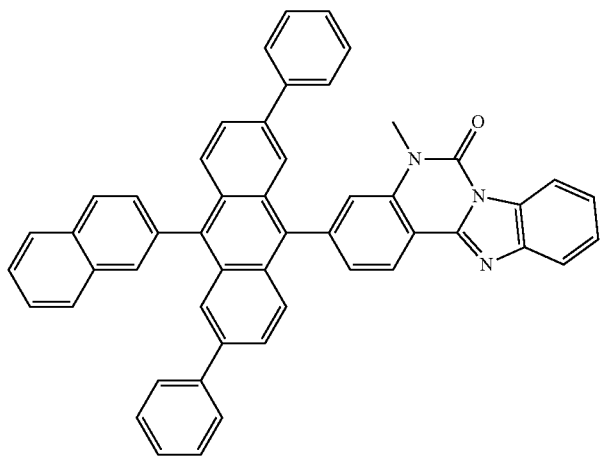
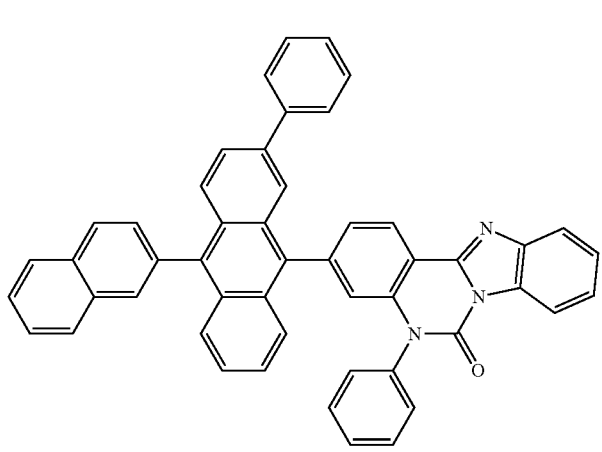
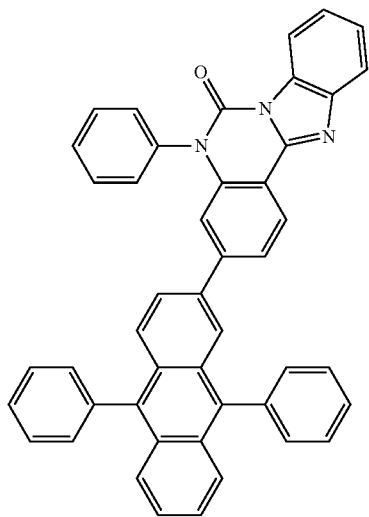

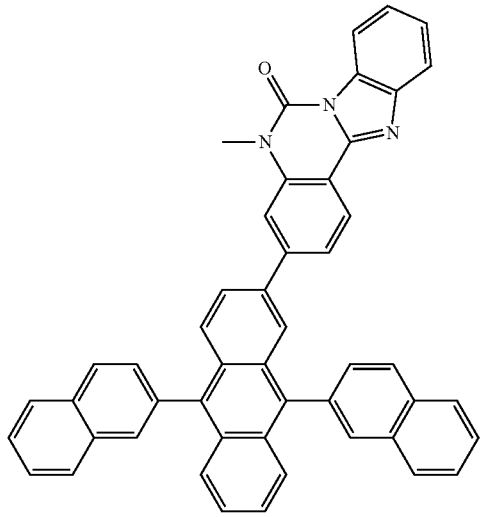
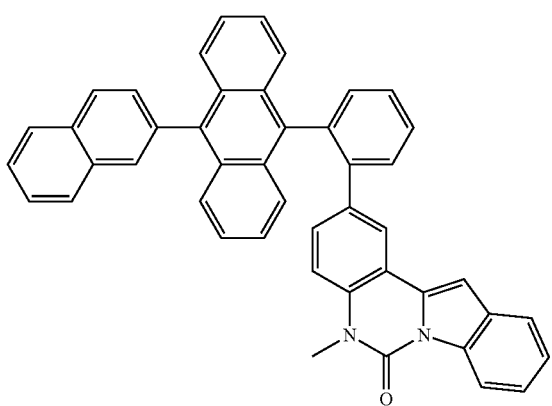
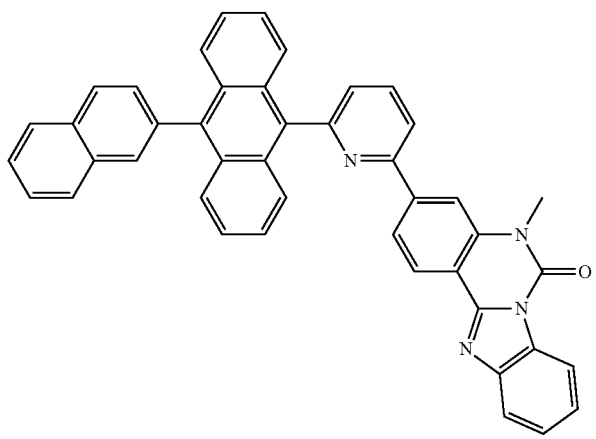
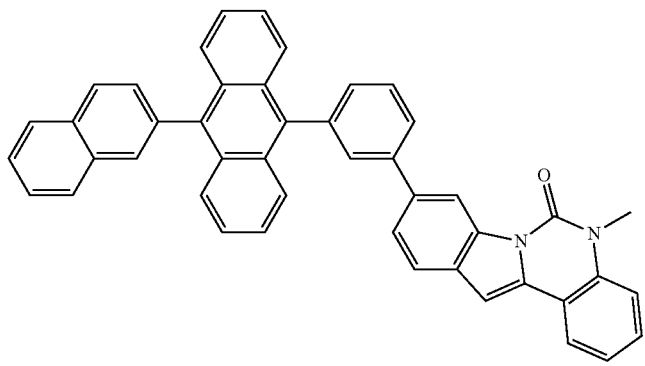
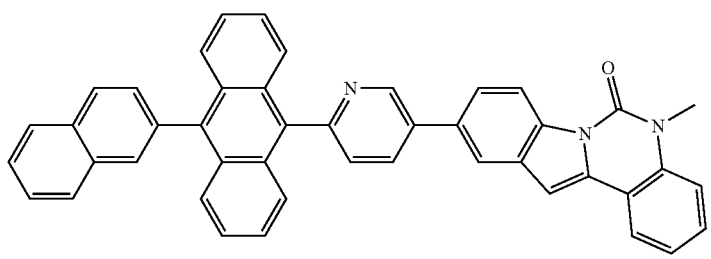

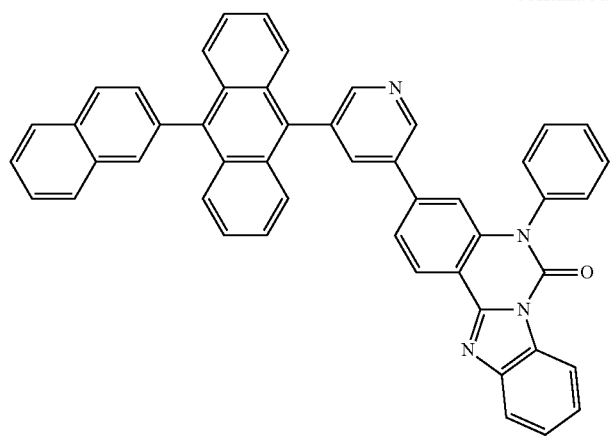
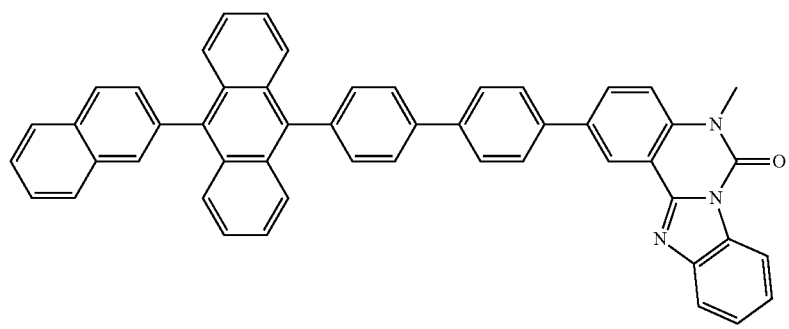
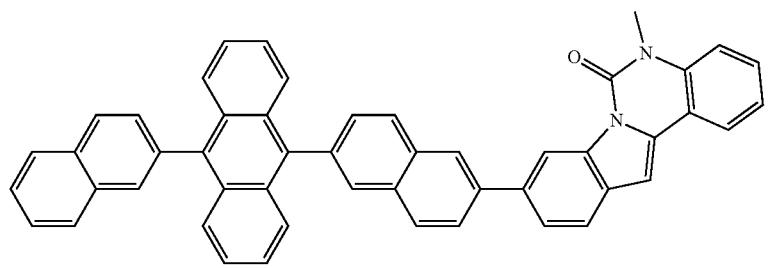
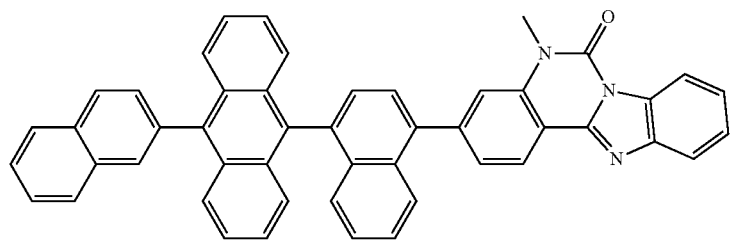
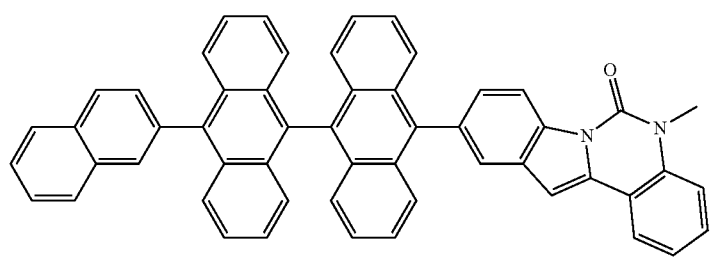

-continued
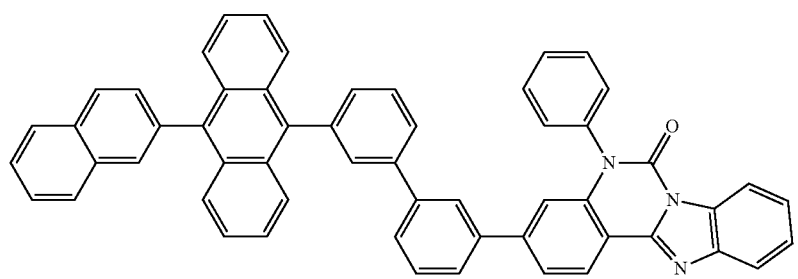
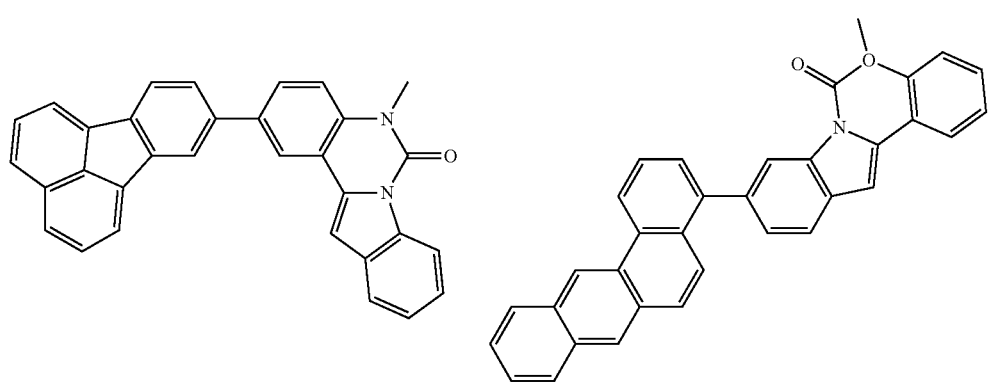
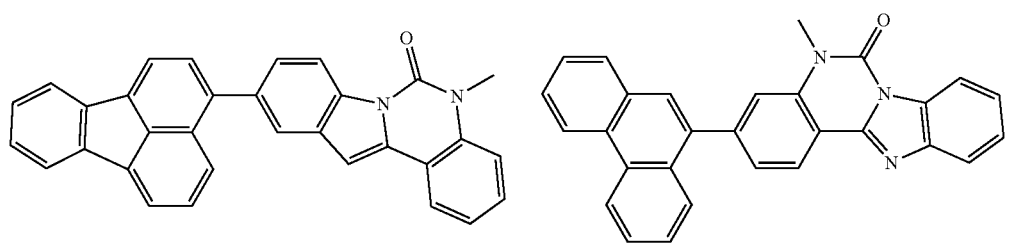
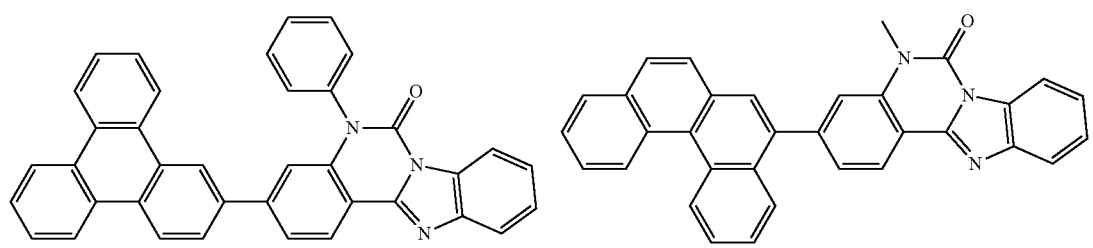
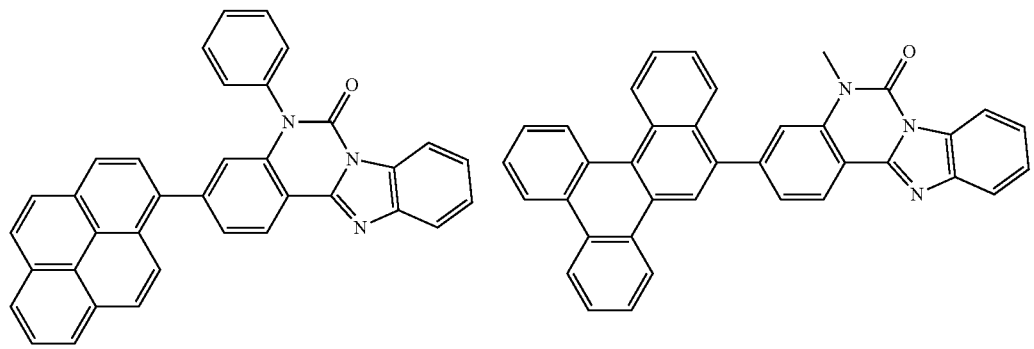

-continued
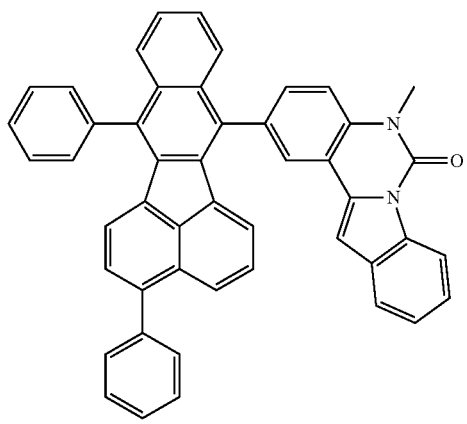
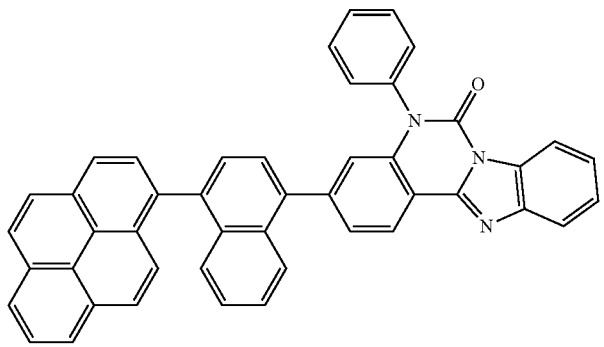
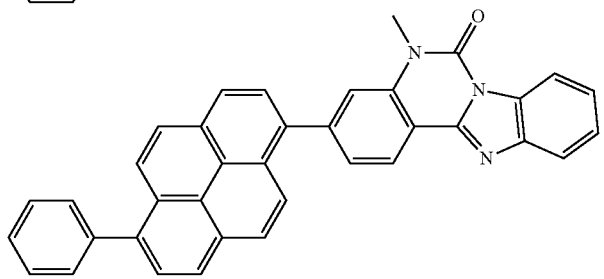
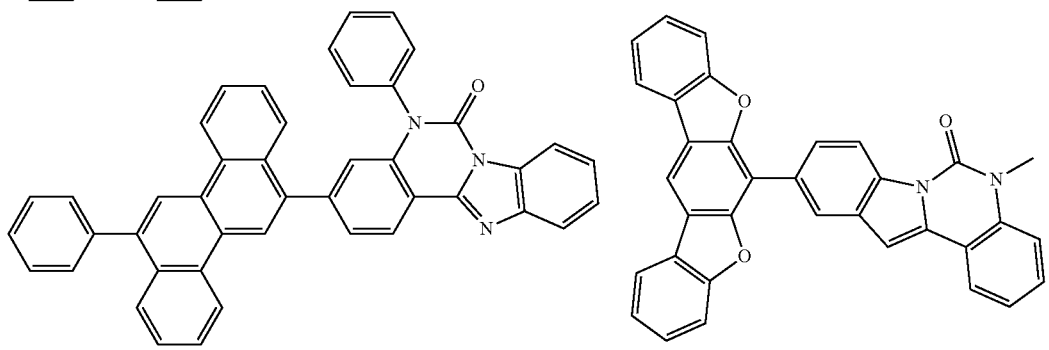
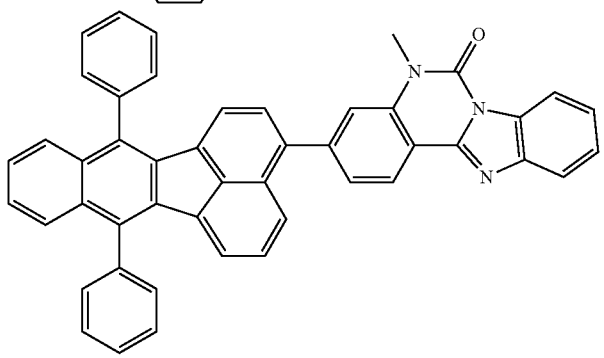

-continued
113
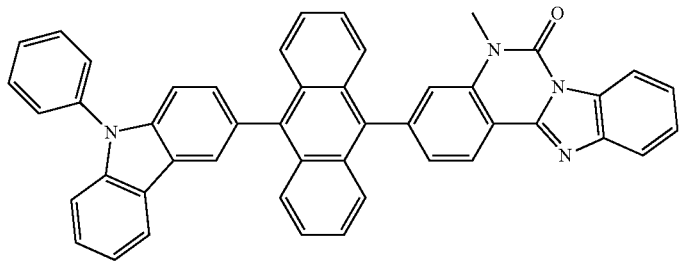
114
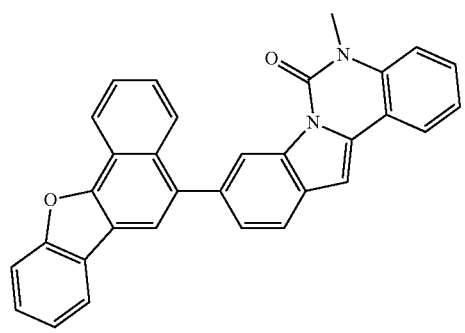
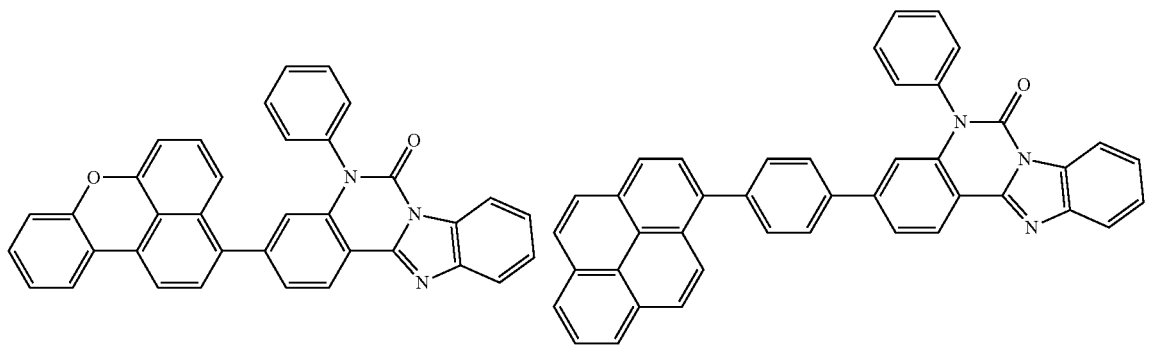
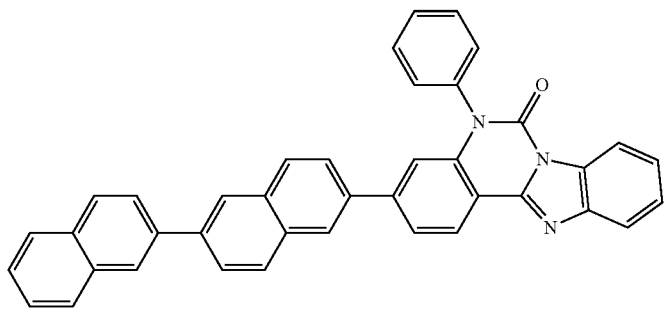
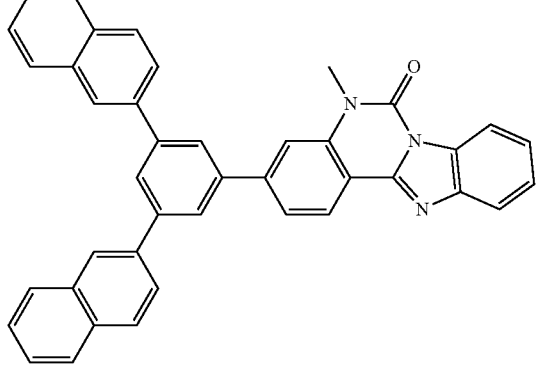
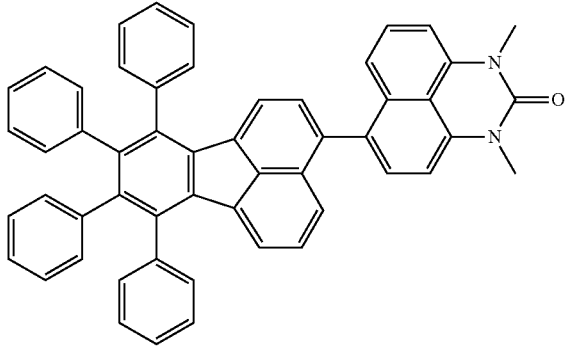
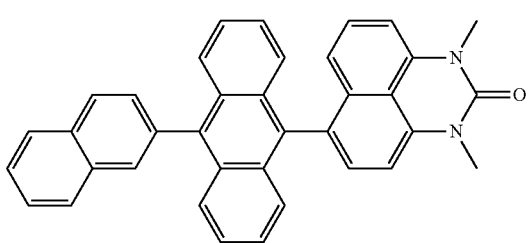

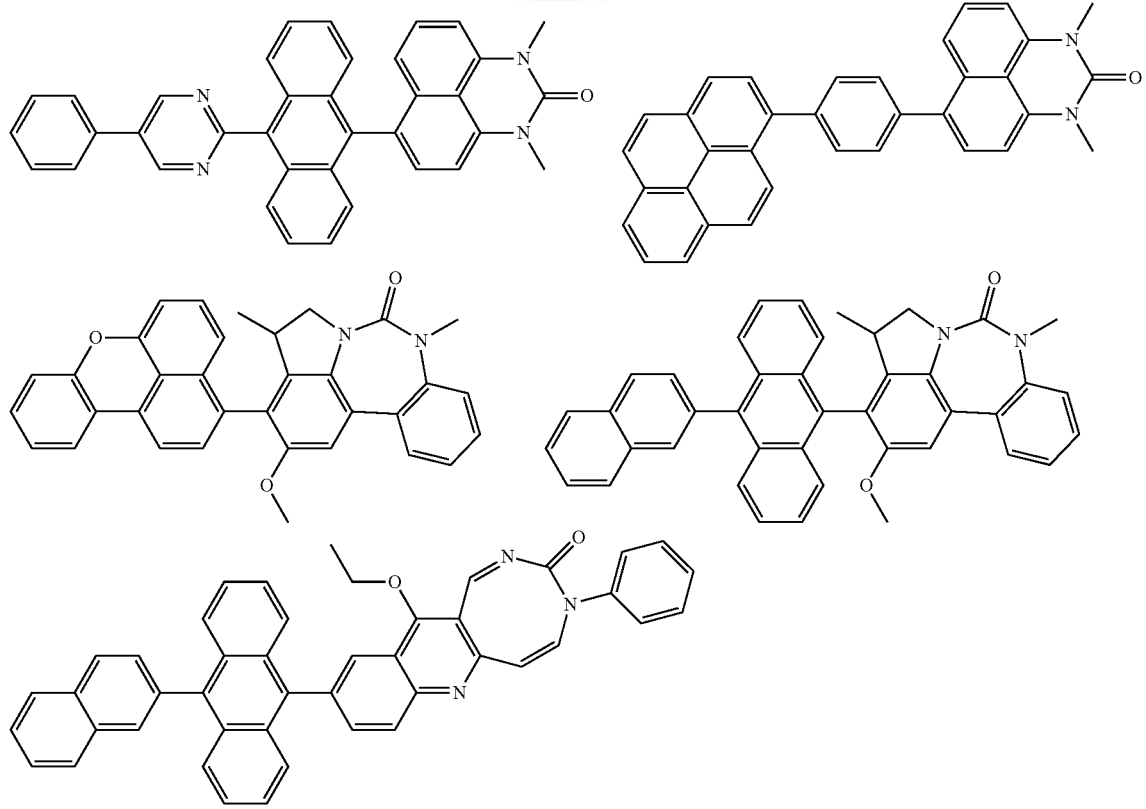

The nitrogen-containing heterocyclic derivative of the invention is useful as a material for organic EL devices.

The nitrogen-containing heterocyclic derivative of the invention is useful as an electron transporting material for organic EL devices.

The organic EL device of the invention is described below.

The organic EL device of the invention comprises an organic thin film layer comprising one or more layers between a cathode and an anode. The organic thin film layer comprises a light emitting layer and at least one layer of the organic thin film layer comprises the nitrogen-containing heterocyclic derivative singly or in mixture.

In another aspect, the organic thin film layer comprises at least one electron transporting layer between the light emitting layer and the cathode, and the electron transporting layer comprises the nitrogen-containing heterocyclic derivative singly or in mixture.

In a preferred embodiment, the electron transporting layer comprising the nitrogen-containing heterocyclic derivative of the invention further comprises a reducing dopant.

Examples of the reducing dopant include a donating metal, a donating metal compound, and a donating metal complex. The reducing dopant may be used alone or in combination of two or more.

The reducing dopant referred to herein is an electron-donating material. The electron-donating material is a material which generates radical anions by the interaction with a coexisting organic material in the electron transporting layer or an organic material in a layer adjacent to the electron transporting layer, or a material having an electron-donating radical.

The donating metal is a metal having a work function of 3.8 eV or less, preferably an alkali metal, an alkaline earth metal, or a rare earth metal, and more preferably Cs, Li, Na, Sr, K, Mg, Ca, Ba, Yb, Eu, or Ce.

The donating metal compound is a compound comprising the above donating metal, preferably a compound comprising an alkali metal, an alkaline earth metal, or a rare earth metal, and more preferably a halide, an oxide, a carbonate, or a borate of these metals, for example, a compound represented by MOx (M: donating metal, x: 0.5 to 1.5), MFx (x: 1 to 3), or M(CO$_3$)$_x$ (x: 0.5 to 1.5).

The donating metal complex is a complex comprising the above donating metal, preferably an organic metal complex of an alkali metal, an alkaline earth metal or a rare earth metal, and more preferably an organic metal complex represented by formula (I):

M$-$(Q)$_n$        (I)

wherein M is a donating metal, Q is a ligand, preferably a carboxylic acid derivative, a diketone derivative, or a quinoline derivative, and n is an integer of 1 to 4.

Examples of the donating metal complex include water-mill-shaped tungsten compounds described in JP 2005-72012A and phthalocyanine compounds having an alkali metal or an alkaline earth metal as the central metal, which are described in JP 11-345687A.

The reducing dopant is preferably at least one selected from the group consisting of an alkali metal, an alkaline earth metal, a rare earth metal, an alkali metal oxide, an alkali metal halide, an alkaline earth metal oxide, an alkaline earth metal halide, a rare earth metal oxide, a rare earth metal halide, an organic complex having an alkali metal, an organic complex having an alkaline earth metal, and an organic complex having a rare earth metal, and more preferably a 8-quinolinol complex of an alkali metal.

Examples of the alkali metal includes:
Li (lithium, work function: 2.93 eV),
Na (sodium, work function: 2.36 eV),
K (potassium, work function: 2.3 eV),
Rb (rubidium, work function: 2.16 eV), and
Cs (cesium, work function: 1.95 eV).

The values of work functions are based on Handbook of Chemistry (Pure Chemistry II, 1984, p. 493, edited by The Chemical Society of Japan). The same applies hereafter.

Preferred examples of the alkaline earth metals are:
Ca (calcium, work function: 2.9 eV),
Mg (magnesium, work function: 3.66 eV),
Ba (barium, work function: 2.52 eV), and
Sr (strontium, work function: 2.0 to 2.5 eV).

The work function of strontium is based of Physics of Semiconductor Device (N.Y., Wiley, 1969, p. 366).

Preferred examples of the rare earth metal are:
Yb (ytterbium, work function: 2.6 eV),
Eu (europium, work function: 2.5 eV),
Gd (gadolinium, work function: 3.1 eV), and
Er (erbium, work function: 2.5 eV).

Examples of the alkali metal oxide include $Li_2O$, $LiO$, and $NaO$. The alkaline earth metal oxide is preferably CaO, BaO, SrO, BeO, or MgO.

Examples of the alkali metal halide include a fluoride, for example, LiF, NaF, CsF, and KF and a chloride, for example, LiCl, KCl, and NaCl.

The alkaline earth metal halide is preferably a fluoride, such as $CaF_2$, $BaF_2$, $SrF_2$, $MgF_2$, and $BeF_2$ and a halide other than fluoride.

An organic EL device wherein the nitrogen-containing heterocyclic derivative of the invention is used in the electron transporting layer is particularly preferred because the driving voltage is reduced while increasing the efficiency. The nitrogen-containing heterocyclic derivative of the invention includes an urea structure in which the oxygen is negatively polarized by a mesomeric effect. With this negative polarization, the affinity with metals is increased to improve the electron injection from metals. Therefore, the amount of electrons in the electron transporting layer is increased to promote the electron injection into the light emitting layer. The promoted electron injection increases the chance of recombination with holes to increase the amount of current, this reducing the driving voltage.

The content of the nitrogen-containing heterocyclic derivative in the electron transporting layer is preferably 50% by mass or more and more preferably 60% by mass or more.

The device structure of the organic EL device will be described below.

(1) Structure of Organic EL Device

The representative structures of the organic EL device of the invention are shown below.

In the organic EL device of the invention, the electron transporting layer is disposed between the light emitting layer and the cathode. The electron transporting layer may be formed adjacent to a layer containing a reducing dopant, such as LiF, in some cases.

The electron blocking layer is disposed between the light emitting layer and the electron transporting layer.

The oxygen-containing fused ring derivative of the invention is preferably used as a material for organic EL devices and more preferably as a blocking material for organic EL devices.

(1) anode/light emitting layer/electron transporting layer/cathode;
(2) anode/light emitting layer/electron transporting layer 1/electron transporting layer 2/cathode;
(3) anode/hole injecting layer/light emitting layer/electron transporting layer/cathode;
(4) anode/hole injecting layer/light emitting layer/electron transporting layer 1/electron transporting layer 2/cathode;
(5) anode/hole injecting layer/light emitting layer/electron transporting layer 1/electron transporting layer 2/layer containing reducing dopant/cathode;
(6) anode/hole injecting layer/light emitting layer/electron transporting layer/layer containing reducing dopant/cathode;
(7) anode/hole injecting layer/hole transporting layer/light emitting layer/electron transporting layer/cathode;
(8) anode/hole injecting layer/hole transporting layer/light emitting layer/electron transporting layer/layer containing reducing dopant/cathode;
(9) anode/hole injecting layer/hole transporting layer/light emitting layer/electron blocking layer/electron transporting layer/layer containing reducing dopant/cathode;
(10) anode/insulating layer/hole injecting layer/hole transporting layer/light emitting layer/electron transporting layer/cathode;
(11) anode/insulating layer/hole injecting layer/hole transporting layer/light emitting layer/electron transporting layer/layer containing reducing dopant/cathode; and
(12) anode/insulating layer/hole injecting layer/hole transporting layer/light emitting layer/electron blocking layer/electron transporting layer/layer containing reducing dopant/cathode.

Of the above, the structure (8) is preferably used, although not limited thereto.

(2) Light-Transmissive Substrate

The organic EL device is formed on a light-transmissive substrate. The light-transmissive substrate serves as a support for the organic EL device. A flat and smooth substrate having a transmittance of 50% or more to 400 to 700 nm visible lights is preferably used.

Examples of the light-transmissive substrate include glass plates made from soda-lime glass, barium-strontium-containing glass, lead glass, aluminosilicate glass, borosilicate glass, barium borosilicate glass, quartz, etc. and polymer plates made from polycarbonate, acryl polymer, polyethylene terephthalate, polyether sulfide, polysulfone, etc.

(3) Anode

The anode injects holes into a hole transporting layer or a light emitting layer, and an anode having a work function of 4.5 eV or more is effective. Examples of the material for the anode include indium-tin oxide (ITO), tin oxide (NESA), indium-zinc oxide (IZO), gold, silver, platinum, and copper.

The anode can be formed by making the electrode material described above into a thin film by a method, such as a vapor deposition process and a sputtering process.

When the light emitted from the light emitting layer is obtained through the anode, the transmittance of the anode to the emitted light is preferably more than 10%. The sheet resistivity of the anode is preferably several hundreds $\Omega/\square$ or smaller. The thickness of the anode depends on the material of the anode and is generally 10 nm to 1 μm, preferably 10 to 200 nm (4) Light Emitting Layer The light emitting layer provides a region for recombining electrons and holes to cause the emission.

The light emitting layer is formed by a known method, such as a vapor deposition method, a spin coating method and LB method. The light emitting layer is particularly preferably a molecular deposit film. The molecular deposit film is a thin film formed by depositing a material compound in a gas phase or a film formed by solidifying a material in a solution or liquid phase. In general, the molecular deposit film can be distinguished from the thin film formed by LB method (molecular accumulation film) based on the differences in the aggregation structure and higher order structures and the differences in the function caused by these structural differences.

The light emitting layer can be formed also by dissolving a binder such as a resin and the material in a solvent to prepare a solution and making the solution into a thin film by a spin coating method, etc.

In addition to the light emitting material comprising the nitrogen-containing heterocyclic derivative of the invention, the light emitting layer may contain, if necessary, a known light emitting material, as long as the object of the invention is not adversely affected. Alternatively, a light emitting layer comprising the light emitting material which comprises the nitrogen-containing heterocyclic derivative of the invention and a light emitting layer comprising a known light emitting material may be laminated to each other.

Examples of the light emitting material and the doping material usable in the light emitting layer include, but not limited to, arylamine compounds, styrylamine compounds, anthracene derivatives, naphthalene derivatives, phenanthrene derivatives, pyrene derivatives, tetracene derivatives, coronene derivatives, chrysene derivatives, fluorescein derivatives, perylene derivatives, phthaloperylene derivatives, naphthaloperylene derivatives, perinone derivatives, phthaloperinone derivatives, naphthaloperinone derivatives, diphenylbutadiene derivatives, tetraphenylbutadiene derivatives, coumarin derivatives, oxadiazole derivatives, bisbenzoxazoline derivatives, bisstyryl derivatives, pyrazine derivatives, cyclopentadiene derivatives, quinoline metal complexes, aminoquinoline metal complexes, benzoquinoline metal complexes, imine compounds, diphenylethylene derivatives, vinylanthracene derivatives, diaminocarbazole derivatives, pyran derivatives, thiopyran derivatives, polymethine compounds, merocyanine compounds, imidazole-chelated oxinoid compounds, quinacridone compounds, rubrene derivatives, and fluorescent dyes.

The light emitting layer of the organic EL device of the invention preferably comprises an arylamine compound, a styrylamine compound, an anthracene compound, a naphthalene compound, a phenanthrene compound, and a pyrene compound.

(5) Hole Injecting/Transporting Layer

The hole injecting/transporting layer is a layer for facilitating the injection of holes into the light-emitting layer and transporting holes to the emission region and has a large hole mobility and an ionization potential generally as small as 5.5 eV or less. A material capable of transporting holes to the light-emitting layer even under a lower electric field strength, for example, a material having a hole mobility of at least $10^{-4}$ cm$^2$/Vs at an electric field strength of $10^4$ to $10^6$ V/cm is preferably used for forming the hole injecting/transporting layer.

The material for forming the hole injecting/transporting layer is not particularly limited as long as the material has the preferred properties mentioned above. For example, the material is selected from known hole transporting materials commonly used as photoconductive materials and known materials commonly used for the hole injecting/transporting layer of organic EL devices.

Examples the material include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, polysilane-based copolymers, aniline-based copolymers, and electroconductive high-molecular oligomers (particularly, thiophene oligomers).

In addition to the compounds mentioned above, porphyrin compounds, aromatic tertiary amine compounds, and styryl amine compounds, particularly the aromatic tertiary amine compounds, are preferably used as the material for the hole injecting/transporting layer.

(6) Electron Transporting Layer

The electron transporting layer facilitates the injection of electrons into the light emitting layer and transports the electrons to the light emitting zone, and has a large electron mobility and an electron affinity generally as large as 2.5 eV or more. The electron transporting layer is preferably formed from a material capable of transporting electrons to the light emitting layer at a lower strength of electric field, preferably having an electron mobility of, for example, at least $10^{-6}$ cm$^2$/V·s under an electric field of $10^4$ to $10^6$ V/cm.

When the nitrogen-containing heterocyclic derivative of the invention is used in the electron transporting layer, the electron transporting layer may be formed from the nitrogen-containing heterocyclic derivative alone or in combination with another material.

The material for forming the electron injecting/transporting layer in combination with the nitrogen-containing heterocyclic derivative is not particularly limited as long as having the preferred properties mentioned above and may be selected from those commonly used as the electron transporting material in the field of photoconductive materials and those known as the materials for the electron injecting/transporting layer of organic EL devices.

In a preferred embodiment of the organic EL device of the invention, the device contains a reducing dopant in the electron transporting region or in the interfacial region between the cathode and the organic layer. In the present invention, an organic EL device containing the compound of the invention and a reducing dopant is preferred. Various compounds having a certain degree of reducing power are usable as the reducing dopant. For example, at least one substance selected from the group consisting of an alkali metal, an alkaline earth metal, a rare earth metal, an alkali metal oxide, an alkali metal halide, an alkaline earth metal oxide, an alkaline earth metal halide, a rare earth metal oxide, a rare earth metal halide, an organic complex of alkali metal, an organic complex of alkaline earth metal, and an organic complex of rare earth metal may be advantageously used.

Preferred reducing dopants are those having a work function of 2.9 eV or less, such as at least one alkali metal selected from the group consisting of Na (work function: 2.36 eV), K (work function: 2.28 eV), Rb (work function: 2.16 eV) and Cs (work function: 1.95 eV) and at least one alkaline earth metal selected from the group consisting of Ca (work function: 2.9 eV), Sr (work function: 2.0 to 2.5 eV) and Ba (work function: 2.52 eV). More preferred are at least one alkali metal selected from the group consisting of K, Rb and Cs, still more preferred are Rb or Cs, and most preferred is Cs. These alkali metals have an extremely high reducing power and improve the luminance and the life of organic EL device when added to the electron injecting zone in a small amount. As the reducing dopant having a work function of 2.9 eV or less, a combination of two or more alkali metals is also preferable and a combination containing Cs such as Cs with Na, Cs with K, Cs with Rb, and Cs with Na and K is particularly preferred. Since the reducing power is efficiently exhibited by the inclusion of Cs in the combination, the luminance and the life of organic EL device are improved by using such a combination is the electron injecting zone.

In the present invention, an electron injecting layer including an insulating material or a semiconductor may be disposed between the cathode and the organic layer. By such an electron injecting layer, the leak of electric current is effectively prevented to improve the electron injecting ability. Preferred examples of the insulating material include at least one metal compound selected from the group consisting of an alkali metal chalcogenide, an alkaline earth metal chalcogenide, an alkali metal halide, and an alkaline earth metal halide. An electron injecting layer including the above alkali metal chalcogenide is preferred because the electron injecting property is further improved. Preferred alkali metal chalcogenides include $Li_2O$, $K_2O$, $Na_2S$, $Na_2Se$, and $Na_2O$; preferred alkaline earth metal chalcogenides include CaO, BaO, SrO, BeO, BaS, and CaSe; preferred alkali metal halides include LiF, NaF, KF, LiCl, KCl, and NaCl; and preferred alkaline earth metal halides include fluoride such as $CaF_2$, $BaF_2$, $SrF_2$, $MgF_2$, and $BeF_2$ and halides other than fluoride.

Examples of the semiconductor for the electron transporting layer include an oxide, a nitride and an oxynitride of at least one element selected from Ba, Ca, Sr, Yb, Al, Ga, In, Li, Na, Cd, Mg, Si, Ta, Sb, and Zn, which are used singly or in combination of two or more. It is preferred that the inorganic compound constituting the electron transporting layer forms a microcrystalline or amorphous insulating thin film. When constituted of the insulating thin film described above, the electron injecting layer is made more uniform to reduce the pixel defect such as dark spots. Examples of such a inorganic compound include the alkali metal chalcogenide, the alkaline earth metal chalcogenide, the alkali metal halide and the alkaline earth metal halide which are described above.

(7) Cathode

The cathode injects electrons into the electron injecting layer, the electron transporting layer or the light emitting layer, and therefore, is formed from an electrode material such as a metal, an alloy, an electroconductive compound, or a mixture thereof, which has a small work function (4 eV or less). Examples of the electrode material include sodium, sodium-potassium alloy, magnesium, lithium, magnesium-silver alloy, aluminum-aluminum oxide, aluminum-lithium alloy, indium, and rare earth metal.

The cathode is formed by making the electrode material into a thin film by a method such as a vapor deposition method and a sputtering method.

When the light emitted from the light emitting layer is allowed to pass through the cathode, the transmittance of the cathode to the emitted light is preferably larger than 10%.

The sheet resistance of the cathode is preferably several hundreds $\Omega/\square$ or less, and the thickness of the cathode is generally 10 nm to 1 μm, preferably 50 to 200 nm.

(8) Insulating Layer

Since an electric filed is applied to the ultrathin films of organic EL device, the pixel defect due to leakage and short circuit is likely to cause. To prevent this, an insulating thin-film layer is preferably disposed between a pair of electrodes.

Examples of the material for forming the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination, or the insulating layer may be a laminate of layers containing these materials.

(9) Electron Blocking Layer

A compound having a high triplet energy due to a wide gap and is highly effective for confining triplet excitons is used as a material for the electron blocking layer. The confinement of triplet excitons causes TTF (Triplet-Triplet Fusion) phenomenon in which a singlet exciton is formed by fusion collision of two triplet excitons. A compound having a heteroring as well as a hydrocarbon ring is used as a material for the electron transporting layer.

(10) Production of Organic EL Device

By the method using the materials mentioned above, the organic EL device is produced by forming an anode, an optional hole injecting/transporting layer, a light emitting layer, an electron transporting layer, an optional electron injecting layer, and a cathode. Alternatively, the organic EL device is produced by forming the layers in reverse order from the cathode to the anode.

The production of the organic EL device will be described below with reference to an organic EL device having a successive layered structure: anode/hole injecting layer/hole transporting layer/light emitting layer/electron transporting layer/cathode on a light-transmissive substrate.

First, an anode is formed on a suitable light-transmissive substrate by making an anode material into a thin film of 1 μm or thick, preferably 10 to 200 nm thick by a method such as a vapor deposition method or a sputtering method. Then, a hole injecting layer is formed on the anode. The hole injecting layer is formed by a method such as a vacuum vapor deposition method, a spin coating method, a casting method and LB method each mentioned above, and preferably by the vacuum vapor deposition method because a uniform film is easily obtained and pin holes hardly occur. The vapor deposition conditions for forming the hole injecting layer vary depending upon the compound (material for the hole injecting layer) to be used, the intended crystal structure of the hole injecting layer, and the recombination structure, and are preferably selected from a deposition source temperature of 50 to 450° C., a vacuum degree of $10^{-7}$ to $10^{-3}$ Torr, a deposition speed of 0.01 to 50 nm/s, a substrate temperature of −50 to 300° C., and a film thickness of 5 nm to 5 μm.

Next, a hole transporting layer is formed on the hole injecting layer. The a hole transporting layer is formed by making a desired hole transporting material into a thin film by a method such as a vacuum vapor deposition method, a sputtering method, a spin coating method, and a casting method, preferably by the vacuum vapor deposition method because a uniform film is easily obtained and pin holes hardly occur. The vapor deposition conditions for forming the hole transporting layer vary depending upon the compound to be used and are generally selected from the conditions described above with respect to the hole injecting layer.

Next, a light emitting layer is formed on the hole transporting layer. The light emitting layer is formed by making a desired organic light emitting material into a thin film by a method such as a vacuum vapor deposition method, a sputtering method, a spin coating method, and a casting method, preferably by the vacuum vapor deposition method because a uniform film is easily obtained and pin holes hardly occur. The vapor deposition conditions for forming the light emitting layer vary depending upon the compound to be used and are generally selected from the conditions described above with respect to the hole injecting layer.

Next, an electron transporting layer is formed on the light emitting layer. Like the formation of the hole injecting layer, the hole transporting layer, and the light emitting layer, the electron transporting layer is preferably formed by the vacuum vapor deposition method because a uniform film is required. The vapor deposition conditions thereof are selected from those described above with respect to the hole injecting layer, the hole transporting layer and the light emitting layer.

The nitrogen-containing heterocyclic derivative of the invention may be co-deposited with another material by the vacuum vapor deposition method. In the spin coating method, the derivative may be mixed with another material.

Finally, by laminating a cathode, the organic EL device is obtained.

The cathode is made of a metal and is formed by the vacuum vapor method or the sputtering method, with the vacuum vapor method being preferred because the underlying organic layers are prevented from being damaged during the film formation.

In the production of the organic EL device, the layers from the anode to the cathode are preferably formed successively and continuously by a single evacuation operation.

The method of forming each layer of the organic EL device of the invention is not particularly limited, and each layer can be formed by a known method, such as a vacuum vapor deposition method and a spin coating method. The organic thin film layer comprising the compound represented by formula (1) in the organic EL device of the invention may be formed by a known method, for example, by a vacuum vapor deposition method, a molecular beam evaporation method (MBE method), and a coating method using a solvent solution, such as a dipping method, a spin coating method, a casting method, a bar coating method and a roll coating method.

The film thickness of each organic layer in the organic EL device of the invention is not particularly limited. The defects, such as pinholes, are likely to be caused if the film thickness is excessively small. If the film thickness is excessively large, a high applied voltage is required to reduce the efficiency. Therefore, the film thickness is preferably selected from several nanometers to 1 μm.

The organic EL device of the invention may contain a compound represented by the following formula between the anode and the hole injecting layer or in the hole injecting layer.

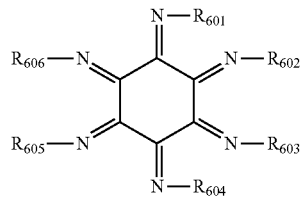

In the above formula, each of $R_{601}$ to $R_{606}$ represents a substituted or unsubstituted alkyl group, a substituted or unsubstituted aryl group, a substituted or unsubstituted aralkyl group, or a substituted or unsubstituted heteroring group, provided that $R_{601}$ to $R_{606}$ may be the same or different, and a pair of $R_{601}$ and $R_{602}$, $R_{603}$ and $R_{604}$, $R_{605}$ and $R_{606}$, $R_{601}$ and $R_{606}$, $R_{602}$ and $R_{603}$, or $R_{604}$ and $R_{605}$ may form a fused ring.

Further, the organic EL device of the invention may contain a compound represented by the following formula between the anode and the hole injecting layer or in the hole injecting layer.

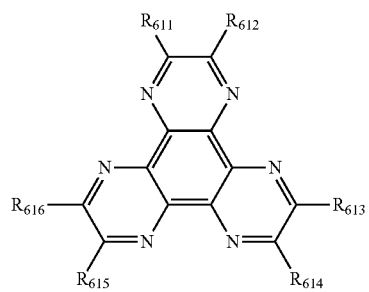

In the above formula, each of $R_{611}$ to $R_{616}$ represents a substituent, preferably an electron withdrawing group, such as a cyano group, a nitro group, a sulfonyl group, a carbonyl group, trifluoromethyl group, and a halogen.

EXAMPLES

The present invention will be described with reference to examples. However, it should be noted that the scope of the invention is not limited to the following examples.

Synthesis Example 1

(a) Synthesis of Compound 1

Compound 1 was synthesized according to the following scheme.

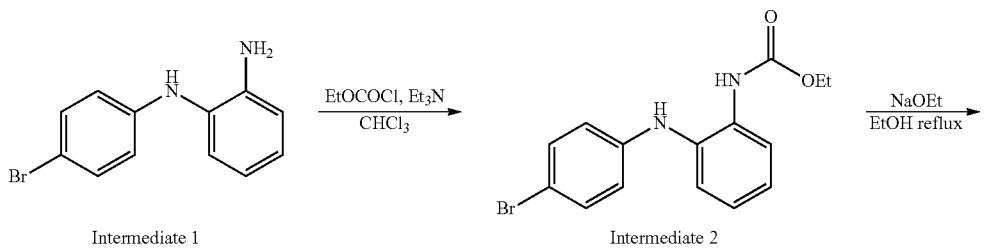

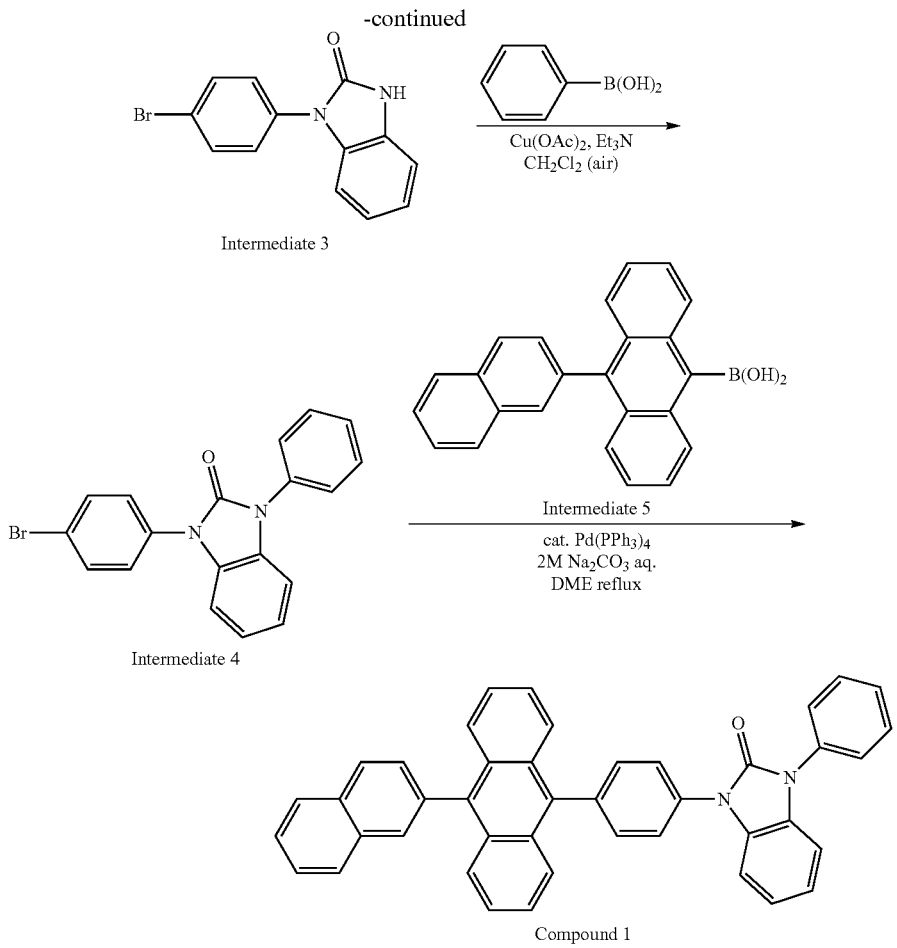

Compound 1

(a-1) Synthesis of Intermediate 2

In an argon atmosphere, a mixture of (4-bromophenyl)-(2-nitrophenyl)amine (Intermediate 1) (16.3 g, 62 mmol), chloroform (100 mL), and triethylamine (17.3 mL, 124 mmol) was cooled to 0° C., and then, stirred at room temperature for 2 h after adding ethyl chloroformate (11.8 mL, 124 mmol) dropwise. The reaction solution was diluted with dichloromethane. The organic layer was washed with a saturated saline solution, dried over magnesium sulfate, and concentrated. The obtained solid was washed with hexane and dried under reduced pressure to obtain Intermediate 2 as a white solid (18.5 g, yield: 91%).

(a-2) Synthesis of Intermediate 3

In an argon atmosphere, Intermediate 2 (18.5 g, 55 mmol) was added to sodium ethoxide (36.6 g, 537 mmol) and absolute ethanol (2.6 L) at room temperature. The resultant mixture was refluxed for 3.5 h under heating. After cooling, evaporating off the solvent under reduced pressure, and adding water, the resultant aqueous solution was neutralized by a 2N hydrochloric acid. The generated solid was collected by filtration, washed with water, and dissolved in ethyl acetate and dichloromethane, and the solution was dried over sodium sulfate. After evaporating off the solvent under reduced pressure, the obtained solid was washed with hexane and dried under reduced pressure to obtain Intermediate 3 as a pale brown solid (14.3 g, yield: 90%).

(a-3) Synthesis of Intermediate 4

In the atmosphere, a mixture of Intermediate 3 (3.0 g, 10 mmol), triethylamine (4.3 mL, 31 mmol), copper (II) acetate (5.7 g, 31 mmol), and dichloromethane (90 mL) was stirred for 12 h while gradually adding phenylboronic acid (6.3 g, 52 mmol). After evaporating off the solvent under reduced pressure and adding ethyl acetate and a 10% aqueous solution of potassium carbonate, the mixture was stirred for 1 h at room temperature. After filtering the reaction solution through celite, the organic layer was successively washed with water and a saturated saline solution and dried over sodium sulfate, and then the solvent was evaporated off under reduced pressure. The residue was purified by silica gel column chromatography (ethyl acetate/toluene). The obtained solid was washed with hexane and dried under reduced pressure to obtain 3.8 g (yield: 100%) of a white solid, which was identified as Intermediate 4 by FD-MS (Field Desorption Mass Spectrometry).

(a-4) Synthesis of Compound 1

Into a solution of Intermediate 4 (2.1 g, 5.8 mmol) in 1,2-dimethoxyethane (30 mL), 10-naphthalene-2-ylanthracene-9-boronic acid (Intermediate 5) (2.2 g, 6.4 mmol), tetrakis(triphenylphosphine)palladium(0) (0.3 g, 2.9 mmol), and a 2 M aqueous solution of sodium carbonate (15 mL) were added, and the mixture was refluxed for 5.5 h under heating. After the reaction, the solid generated by adding water was collected by filtration, washed with water, and dried under reduced pressure. The obtained crude product was purified by silica gel column chromatography (ethyl acetate/toluene/hexane), washed with hexane, and dried under reduced pressure to obtain 3.2 g (yield: 94%) of a pale yellow solid, which was identified as Compound 1 by FD-MS.

Synthesis Example 2

(b) Synthesis of Compound 2

Compound 2 was synthesized according to the following scheme.

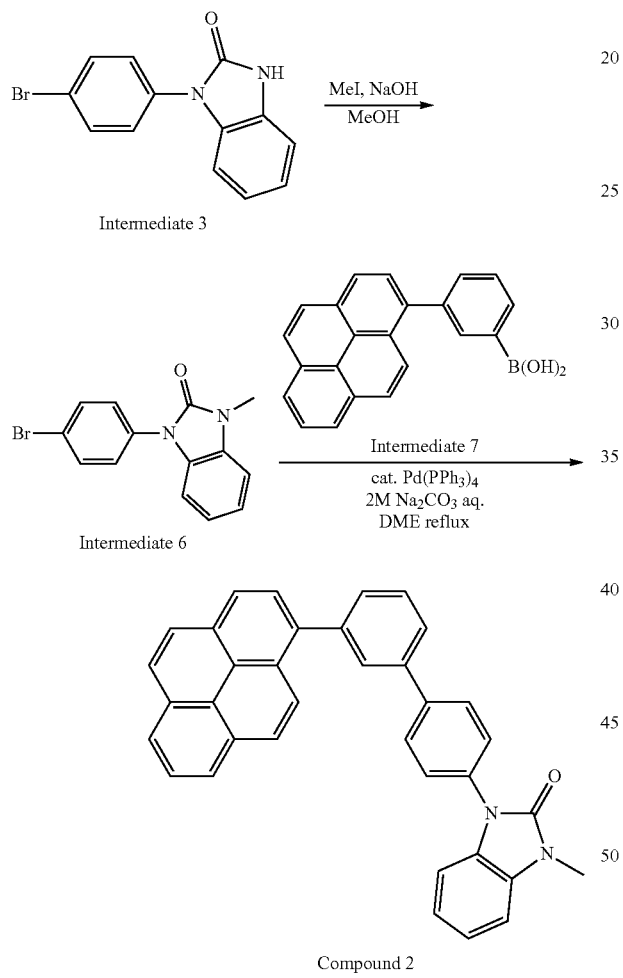

(b-1) Synthesis of Intermediate 6

A mixture of Intermediate 3 (5.0 g, 17 mmol), sodium hydroxide (2.1 g, 52 mmol), iodomethane (8.6 mL, 138 mmol), and absolute methanol (100 mL) was stirred at room temperature for 16 h. The solid generated by adding water was collected by filtration, washed with water, and dried under reduced pressure to obtain 5.1 g (yield: 98%) of a white solid, which was identified as Intermediate 6 by FD-MS.

(b-2) Synthesis of Compound 2

The procedure of Synthesis Example 1 (a-4) was repeated by using Intermediate 6 in place of Intermediate 4 and using Intermediate 7 in place of Intermediate 5. The obtained compound was identified as Compound 2 by FD-MS.

Synthesis Example 3

(c) Synthesis of Compound 3

Compound 3 was synthesized according to the following scheme.

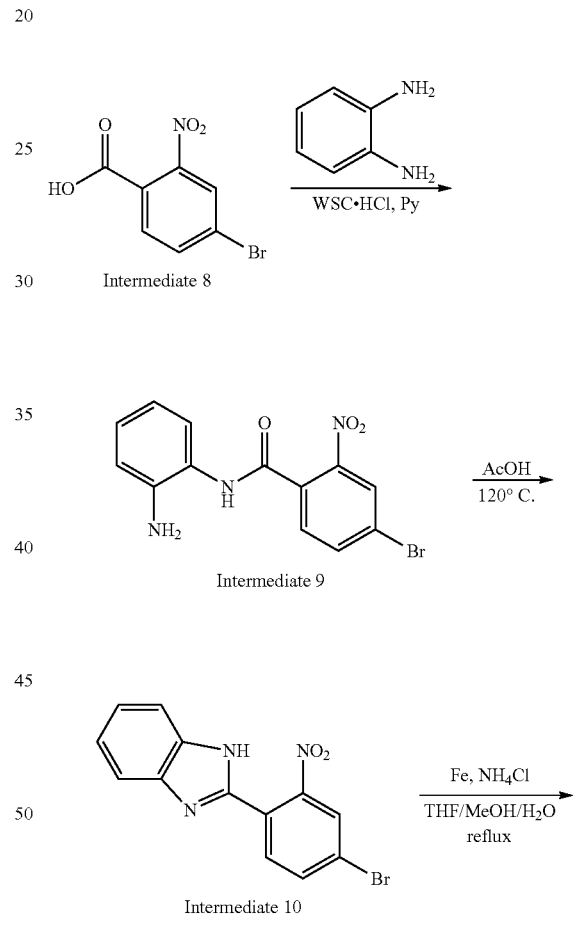

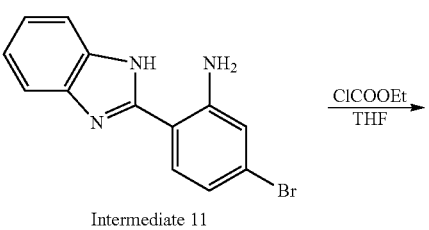

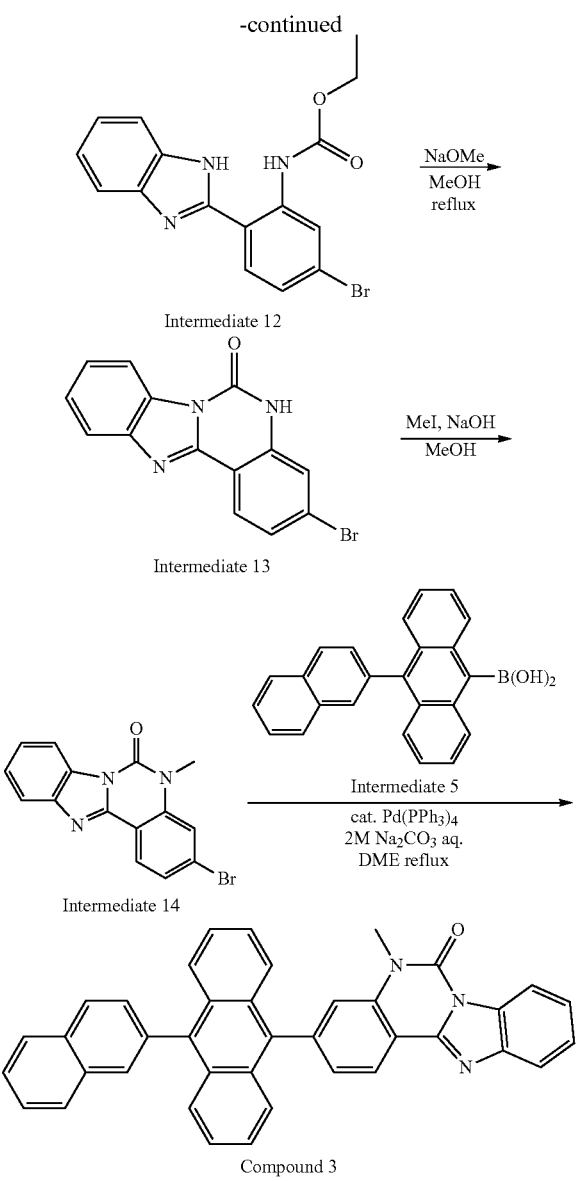

(c-1) Synthesis of Intermediate 9

In an argon atmosphere, 1-(3-dimethylaminopropyl)-3-ethylcarbodiimide hydrochloride (23.5 g, 122 mmol) was added at room temperature to a mixture of 4-bromo-2-nitrobenzoic acid (Intermediate 8) (25.0 g, 102 mmol), 1,2-phenylenediamine (11.0 g, 102 mmol), and pyridine (200 mL), and the resultant mixture was stirred for 4.5 h. The solid generated by adding water was collected by filtration, washed with water, and dried under reduced pressure to obtain Intermediate 9 (27.8 g, yield: 81%) as a yellow solid.

(c-2) Synthesis of Intermediate 10

In an argon atmosphere, acetic acid (260 ml) was added to Intermediate 9 (26.0 g, 77 mmol), and the mixture was refluxed for 14 h under heating. After cooling, the mixture was neutralized by a 20% aqueous solution of sodium hydroxide. The generated solid was collected by filtration, successively washed with a saturated sodium hydrogencarbonate aqueous solution and water, and dried under reduced pressure to obtain Intermediate 10 (21.3 g, yield: 87%) as a yellow solid.

(c-3) Synthesis of Intermediate 11

Into Intermediate 10 (15.4 g, 48 mmol) and tetrahydrofuran (60 mL), iron (18.9 g, 339 mmol), ammonium chloride (13.0 g, 242 mmol), methanol (30 mL), and water (30 mL) were added, and the mixture was refluxed for 8.5 h under heating. After cooling, the reaction liquid was filtered through celite and the filtrate was extracted with ethyl acetate. The organic layer was successively washed with water and a saturated saline solution and dried over sodium sulfate, and then, the solvent was evaporated off under reduced pressure. The residue was purified by silica gel column chromatography (ethyl acetate/hexane) and the obtained solid was washed with hexane and dried under reduced pressure to obtain Intermediate 11 (12.5 g, yield: 89%) as a white solid.

(c-4) Synthesis of Intermediate 12

In an argon atmosphere, a mixture of Intermediate 11 (7.4 g, 26 mmol), ethyl chloroformate (2.9 mL, 31 mmol), and dry tetrahydrofuran (50 mL) was refluxed for 24 h under heating. After cooling, the solid generated by adding water was collected by filtration, successively washed with water and acetone, and dried under reduced pressure to obtain Intermediate 12 (9.0 g, yield: 98%) as a white solid.

(c-5) Synthesis of Intermediate 13

In an argon atmosphere, a 5M methanol solution of sodium methoxide (1.6 mL, 8.0 mmol) was added to Intermediate 12 (1.9 g, 5.4 mmol) and absolute methanol (26 mL), and the resultant mixture was refluxed for 5 h under heating. After cooling, the solid generated by adding water was collected by filtration, successively washed with water, methanol, acetone, and dichloromethane, and dried under reduced pressure to obtain Intermediate 13 (1.4 g, yield: 86%) as a white solid.

(c-6) Synthesis of Intermediate 14

The procedure of Synthesis Example 2 (b-1) was repeated except for using Intermediate 13 in place of Intermediate 3. The obtained compound was identified as Intermediate 14 by FD-MS (yield: 95%).

(c-7) Synthesis of Compound 3

The procedure of Synthesis Example 1 (a-4) was repeated except for using Intermediate 14 in place of Intermediate 4. The obtained compound was identified as Compound 3 by FD-MS (yield: 87%).

Synthesis Example 4

(d) Synthesis of Compound 4

Compound 4 was synthesized according to the following scheme.

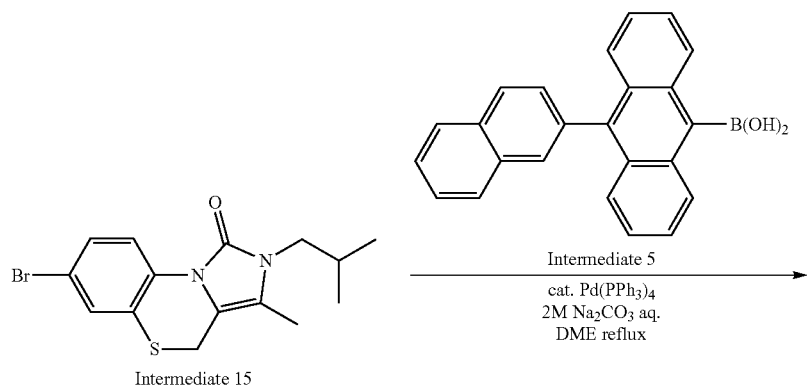

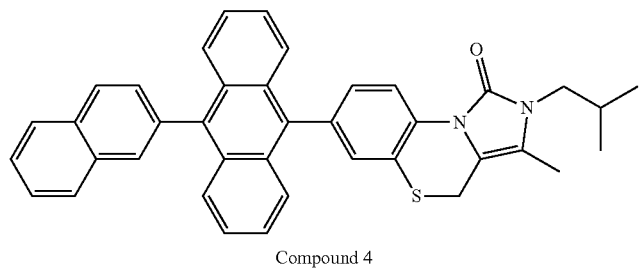

Compound 4

The procedure of Synthesis Example 1 (a-4) was repeated except for using Intermediate 15 in place of Intermediate 4. The obtained compound was identified as Compound 4 by FD-MS.

Synthesis Example 5

(e) Synthesis of Compound 5

Compound 5 was synthesized according to the following scheme.

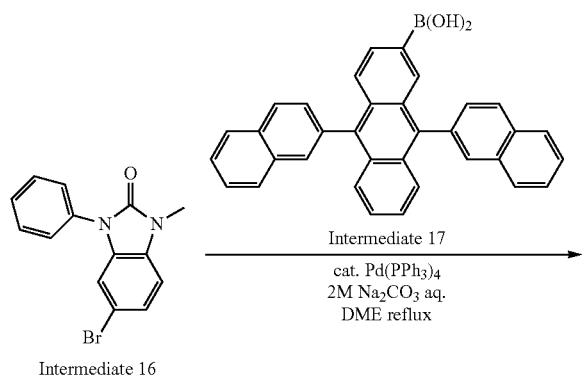

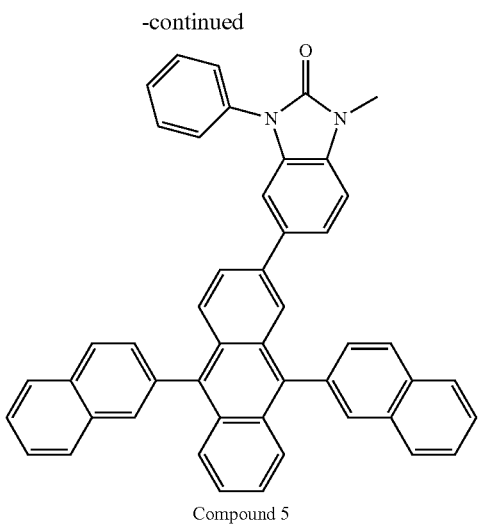

Compound 5

The procedure of Synthesis Example 1 (a-4) was repeated except for using Intermediate 16 in place of Intermediate 4 and using Intermediate 17 in place of Intermediate 5. The obtained compound was identified as Compound 5 by FD-MS.

Synthesis Example 6

(f) Synthesis of Compound 6

Compound 6 was synthesized according to the following scheme.

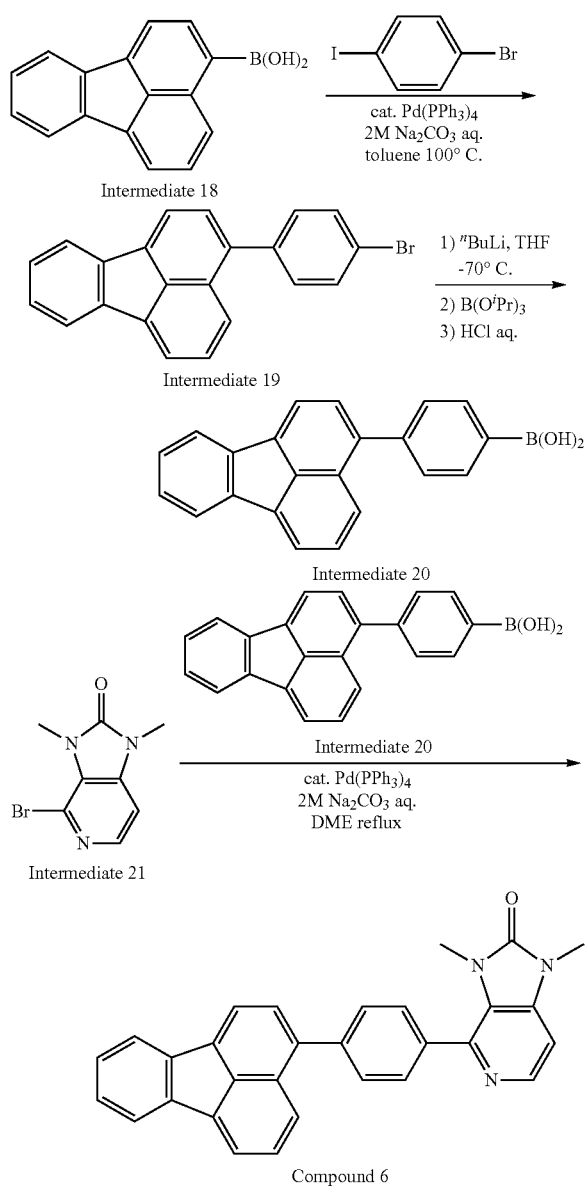

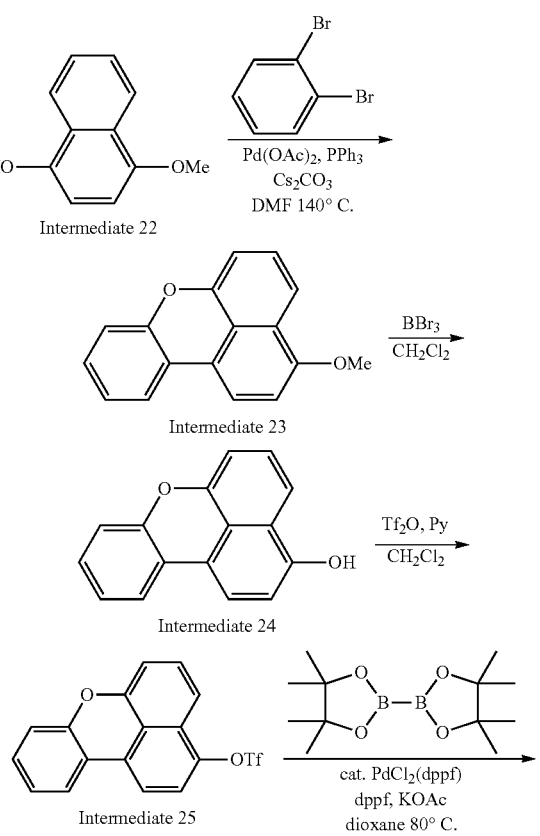

the resultant solution was cooled to −70° C. The solution was stirred at −70° C. for 2 h after adding a 1.65 M hexane solution of n-butyl lithium (17.2 mL, 28 mmol) dropwise, then stirred at −70° C. for 1 h after adding triisopropyl borate (17.7 mL, 77 mmol) dropwise, and further stirred for 5 h while raising the temperature to room temperature. The obtained reaction solution was acidified by adding a 2 M hydrochloric acid and extracted with ethyl acetate. After removing the aqueous layer, the organic layer was washed with a saturated saline solution, dried over anhydrous sodium sulfate, and filtered. The solvent was evaporated off under reduced pressure and the residue was washed with a hexane-ethyl acetate mixture to obtain Intermediate 20 (7.9 g, yield: 95%).

(f-3) Synthesis of Compound 6

The procedure of Synthesis Example 1 (a-4) was repeated except for using Intermediate 21 in place of Intermediate 4 and using Intermediate 20 in place of Intermediate 5. The obtained compound was identified as Compound 6 by FD-MS.

Synthesis Example 7

(g) Synthesis of Compound 7

Compound 7 was synthesized according to the following scheme.

(f-1) Synthesis of Intermediate 19

The procedure of Synthesis Example 1 (a-4) was repeated except for using 4-bromoiodobenzene in place of Intermediate 4, using Intermediate 18 in place of Intermediate 5, using toluene in place of 1,2-dimethoxyethane, and changing the reaction temperature to 100° C. After the reaction, the reaction solution was cooled to room temperature and extracted with toluene. After removing the aqueous layer, the organic layer was washed with a saturated saline solution, dried over anhydrous sodium sulfate, and filtered. Then, the solvent was evaporated off under reduced pressure and the residue was purified by silica gel chromatography to obtain Intermediate 19 (9.2 g, yield: 70%).

(f-2) Synthesis of Intermediate 20

In an argon atmosphere, Intermediate 19 (9.2 g, 26 mmol) and tetrahydrofuran (129 mL) were charged into a flask, and

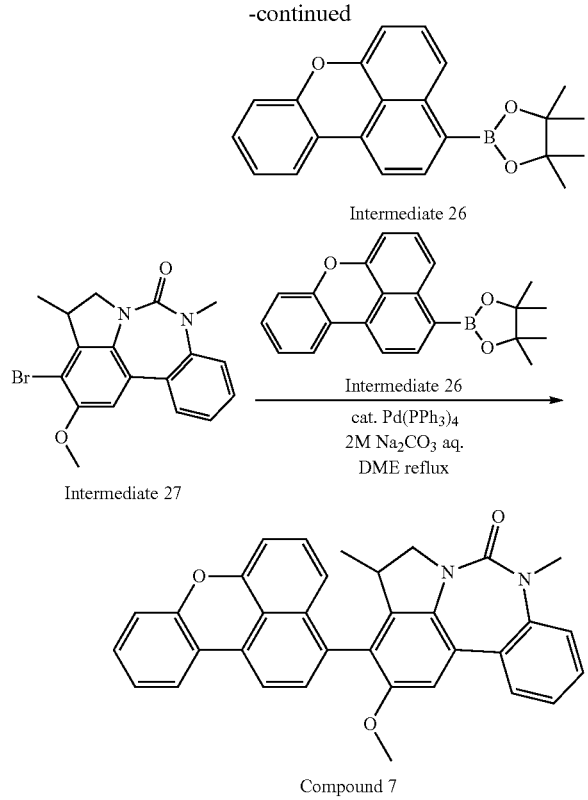

(g-1) Synthesis of Intermediate 23

Into a solution of 4-methoxy-1-naphthol (Intermediate 22) (7.0 g, 40 mmol) and 1,2-dibromobenzene (11.3 g, 48 mmol) in dimethylformamide (200 mL), cesium carbonate (52.1 g, 160 mmol), triphenylphosphine (2.1 g, 8.0 mmol), and palladium(II) acetate (0.45 g, 2.0 mmol) were successively added. The resultant mixture was stirred at 140° C. for 15 h. After cooling to room temperature, the mixture was added with water and ethyl acetate and separated into the aqueous layer and the organic layer. The aqueous layer was further extracted with ethyl acetate, and the extract was washed with water and a saturated saline solution. The combined organic layer was dried over anhydrous sodium sulfate, filtered, and then concentrated. After adding water and methanol to the obtained residue, the mixture was extracted with diethyl ether and ethyl acetate, and the extract was washed with water and then a saturated saline solution. The combined organic layer was dried over anhydrous sodium sulfate, filtered, and then concentrated. The obtained residue was purified by silica gel chromatography, dispersed in a hexane-ethyl acetate for washing, and then dried to obtain Intermediate 23 (3.2 g, yield: 33%) as a yellow solid.

(g-2) Synthesis of Intermediate 24

In an argon atmosphere, a solution of Intermediate 23 (3.3 g, 13 mmol) in dichloromethane (100 mL) was cooled to −68° C. in a dry ice-methanol bath and a 1 M dichloromethane solution of boron tribromide (14 mL, 14 mmol) was added to the solution dropwise over 20 min. The resultant mixture was stirred for 4 h while gradually raising the temperature to room temperature, cooled with ice, added with water drops by drops to carefully deactivate boron tribromide, and further added with 100 mL of water. The generated precipitation was collected by filtration, washed with water and dichloromethane, and dried to obtain Intermediate 24 (2.4 g) as a solid. The filtrate was separated into the aqueous layer and the organic layer and the aqueous layer was extracted with dichloromethane. The collected organic layer was dried over anhydrous sodium sulfate, filtered, and concentrated. The obtained reside was dispersed in a small amount of dichloromethane for washing and dried to obtain an additional Intermediate 24 (0.5 g) as a solid, thereby obtaining Intermediate 24 (2.9 g, yield: 94%) in total.

(g-3) Synthesis of Intermediate 25

In an argon atmosphere, a dispersion of Intermediate 24 (2.9 g, 12 mmol) in dichloromethane (100 mL) was cooled with ice and added with pyridine (4.0 mL, 49 mmol). The resultant solution was added with trifluoromethanesulfonic acid anhydride (3.0 mL, 18 mmol) over 10 min, stirred for 5 min under cooling with ice, and further stirred for 3 h while gradually raising the temperature to room temperature. The obtained solution was added with a 1 M hydrochloric acid (50 mL) under cooling with ice and the mixture was extracted with dichloromethane. The extract was washed with a saturated aqueous solution of sodium hydrogencarbonate, dried over anhydrous sodium sulfate, filtered, and concentrated. The obtained residue was dispersed in a hexane-ethyl acetate mixture for washing and dried to obtain Intermediate 25 as a solid. The mother liquor for washing was concentrated and purified by silica gel chromatography. The obtained residue was dispersed in hexane for washing and dried to obtain an additional Intermediate 25 as a solid, thereby obtaining Intermediate 25 (3.0 g, yield: 67%) in total as a brownish white solid.

(g-4) Synthesis of Intermediate 26

A solution of Intermediate 25 (3.0 g, 8.2 mmol), bis (pinacolato)diboron (2.3 g, 9.0 mmol), a dichloromethane adduct of [1,1'-bis(diphenylphosphino)ferrocene]palladium (II) dichloride (0.34 g, 0.41 mmol), 1,1'-bis(diphenylphosphino)ferrocene (0.23 g, 0.41 mmol), and potassium acetate (2.42 g, 25 mmol) in 1,4-dioxane (50 mL) was stirred at 80° C. for 17 h. After adding bis(pinacolato)diboron (1.15 g, 4.5 mmol), a dichloromethane adduct of [1,1'-bis(diphenylphosphino)ferrocene]palladium(II) dichloride (0.34 g, 0.41 mmol), and 1,1'-bis(diphenylphosphino)ferrocene (0.23 g, 0.41 mmol), the solution was further stirred at 80° C. for 7.5 h. The reaction solution was cooled to room temperature, added with water and ethyl acetate, and filtered. The resultant mixed solution was separated into the aqueous layer and the organic layer, and the aqueous layer was extracted with ethyl acetate. The combined organic layer was washed with a saturated saline solution, dried over anhydrous sodium sulfate, filtered, and concentrated. The obtained residue was purified by silica gel chromatography to obtain Intermediate 26 (1.5 g, yield: 52%) as a yellow solid.

(g-5) Synthesis of Compound 7

The procedure of Synthesis Example 1 (a-4) was repeated except for using Intermediate 27 in place of Intermediate 4 and using Intermediate 26 in place of Intermediate 5. The obtained compound was identified as Compound 7 by FD-MS.

Synthesis Example 8

(h) Synthesis of Compound 8

Compound 8 was synthesized according to the following scheme.

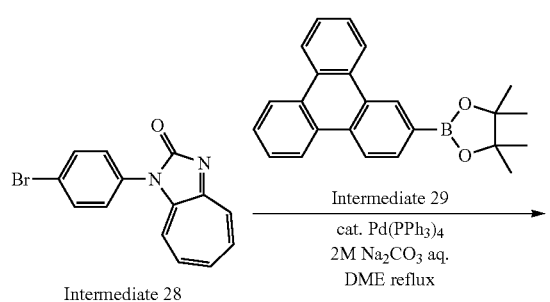

Intermediate 28

Intermediate 29
cat. Pd(PPh$_3$)$_4$
2M Na$_2$CO$_3$ aq.
DME reflux

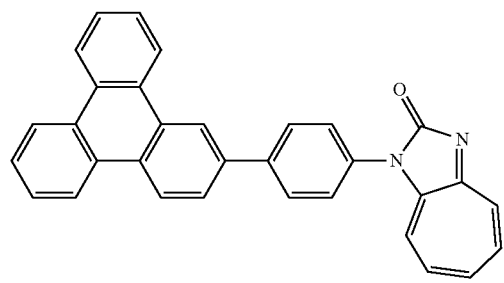

Compound 8

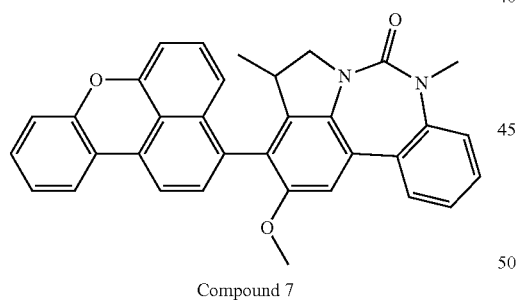

Compound 7

The procedure of Synthesis Example 1 (a-4) was repeated except for using Intermediate 28 in place of Intermediate 4 and using Intermediate 29 in place of Intermediate 5. The obtained compound was identified as Compound 8 by FD-MS.

Synthesis Example 9

(i) Synthesis of Compound 9

Compound 9 was synthesized according to the following scheme.

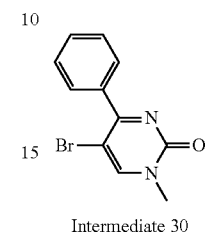

Intermediate 30

Intermediate 31
cat. Pd(PPh$_3$)$_4$
2M Na$_2$CO$_3$ aq.
DME reflux

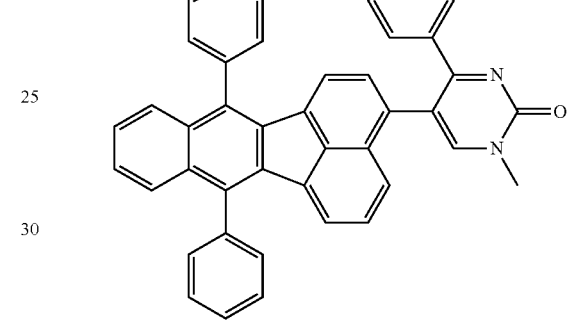

Compound 9

The procedure of Synthesis Example 1 (a-4) was repeated except for using Intermediate 30 in place of Intermediate 4 and using Intermediate 31 in place of Intermediate 5. The obtained compound was identified as Compound 9 by FD-MS.

Synthesis Example 10

(j) Synthesis of Compound 10

Compound 10 was synthesized according to the following scheme.

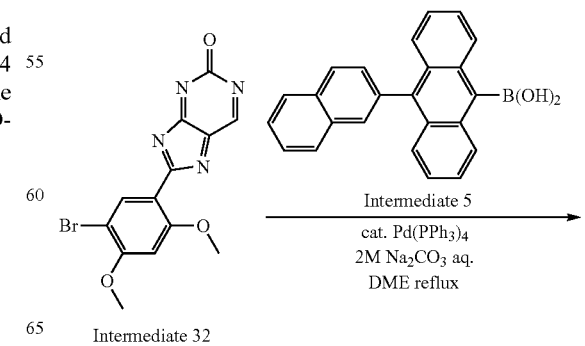

Intermediate 32

Intermediate 5
cat. Pd(PPh$_3$)$_4$
2M Na$_2$CO$_3$ aq.
DME reflux

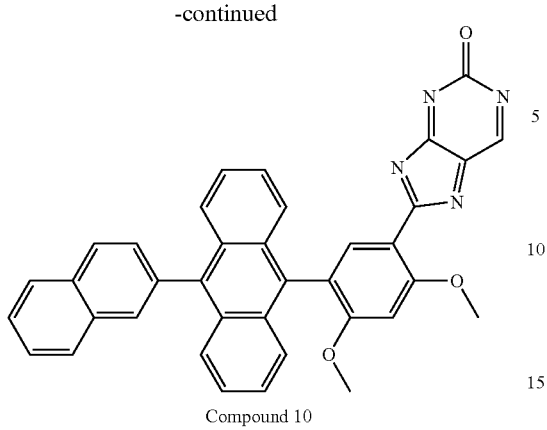
Compound 10
The procedure of Synthesis Example 1 (a-4) was repeated except for using Intermediate 32 in place of Intermediate 4. The obtained compound was identified as Compound 10 by FD-MS.
Synthesis Example 11
(k) Synthesis of Compound 11
Compound 11 was synthesized according to the following scheme.
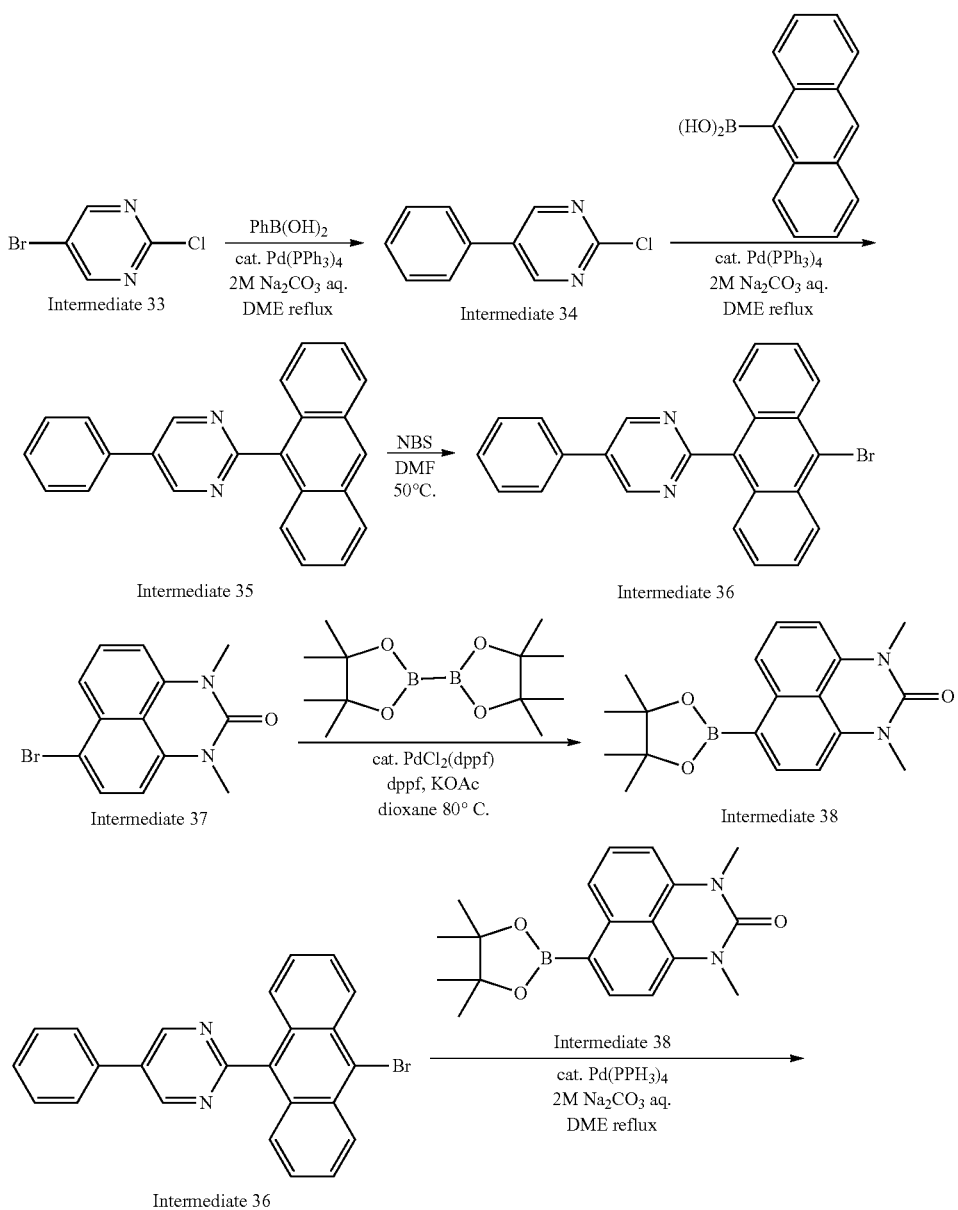

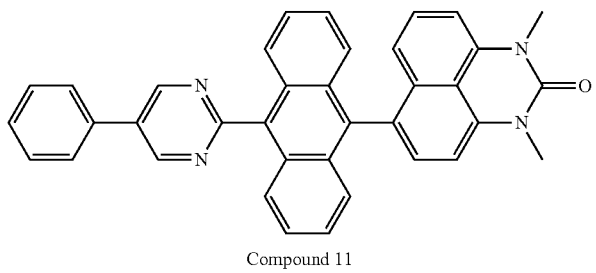

Compound 11

(k-1) Synthesis of Intermediate 34

The procedure of Synthesis Example 1 (a-4) was repeated except for using 5-bromo-2-chloropyrimidine (Intermediate 33) (18.1 g, 94 mmol) in place of Intermediate 4 and using dihydroxyphenylborane (11.6 g, 95 mmol) in place of Intermediate 5, thereby obtaining Intermediate 34 (14 g, yield: 77%).

(k-2) Synthesis of Intermediate 35

The procedure of Synthesis Example 1 (a-4) was repeated except for using Intermediate 34 in place of Intermediate 4 and using 9-anthraceneboronic acid in place of Intermediate 5, thereby obtaining Intermediate 35.

(k-3) Synthesis of Intermediate 36

In an argon atmosphere, Intermediate 35 (4.8 g, 14 mmol) was dissolved in dry dimethylformamide (95 mL) at 40° C. After adding N-bromosuccinimide (2.7 g, 15 mmol), the solution was stirred at 50° C. for 2.5 h. After the reaction, the solid generated by adding water was collected by filtration, washed with water, and dried under reduced pressure. The obtained crude product was purified by silica gel column chromatography (ethyl acetate/hexane). The resultant solid was washed with hexane and methanol and dried under reduced pressure to obtain 4.6 g (yield: 78%) of a yellow solid, which was identified as Intermediate 36 by FD-MS.

(k-4) Synthesis of Intermediate 38

The procedure of Synthesis Example 7 (g-4) was repeated except for using Intermediate 37 in place of Intermediate 25, thereby obtaining Intermediate 38.

(k-5) Synthesis of Compound 11

The procedure of Synthesis Example 1 (a-4) was repeated except for using Intermediate 36 in place of Intermediate 4 and using Intermediate 38 in place of Intermediate 5. The obtained compound was identified as Compound 11 by FD-MS.

Synthesis Example 12

(l) Synthesis of Compound 12

Compound 12 was synthesized according to the following scheme.

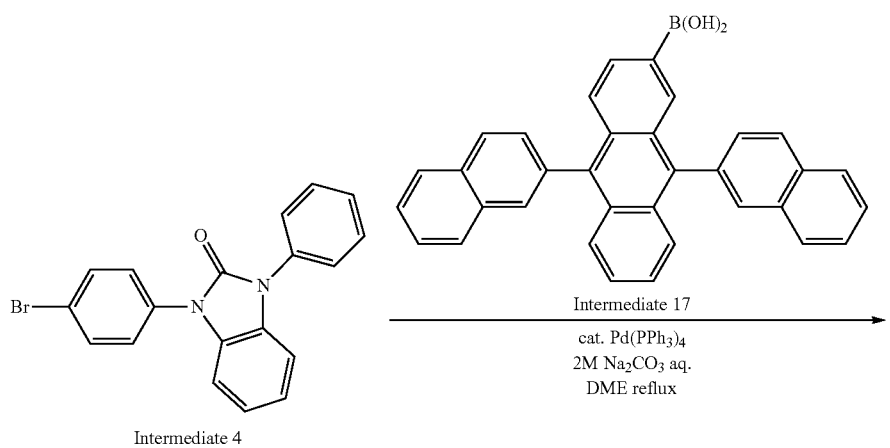

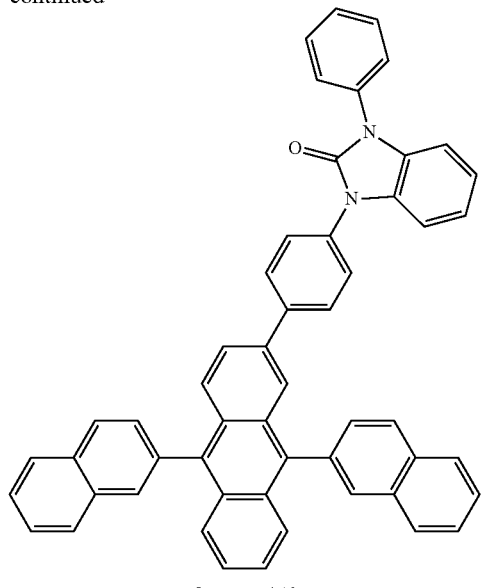

Compound 12

The procedure of Synthesis Example 1 (a-4) was repeated except for using Intermediate 17 in place of Intermediate 5 to obtain a compound (yield: 79%), which was identified as Compound 12 by FD-MS.

Synthesis Example 13

(m) Synthesis of Compound 13

Compound 13 was synthesized according to the following scheme.

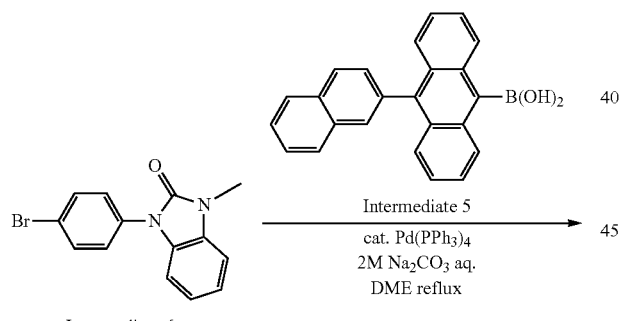

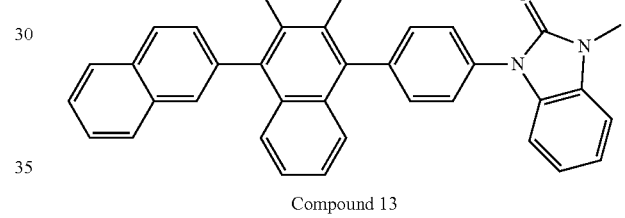

Compound 13

The procedure of Synthesis Example 1 (a-4) was repeated except for using Intermediate 6 in place of Intermediate 4 to obtain a compound (yield: 95%), which was identified as Compound 13 by FD-MS.

Synthesis Example 14

(n) Synthesis of Compound 14

Compound 14 was synthesized according to the following scheme.

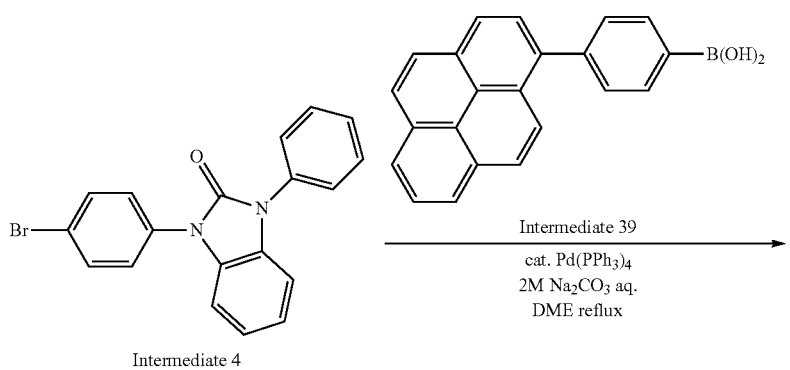

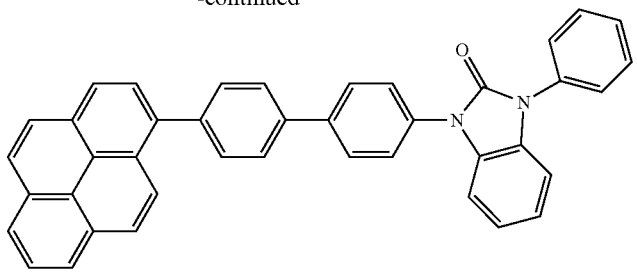

Compound 14

The procedure of Synthesis Example 1 (a-4) was repeated except for using Intermediate 39 in place of Intermediate 5 to obtain a compound (yield: 67%), which was identified as Compound 14 by FD-MS.

Synthesis Example 15

(o) Synthesis of Compound 15

Compound 15 was synthesized according to the following scheme.

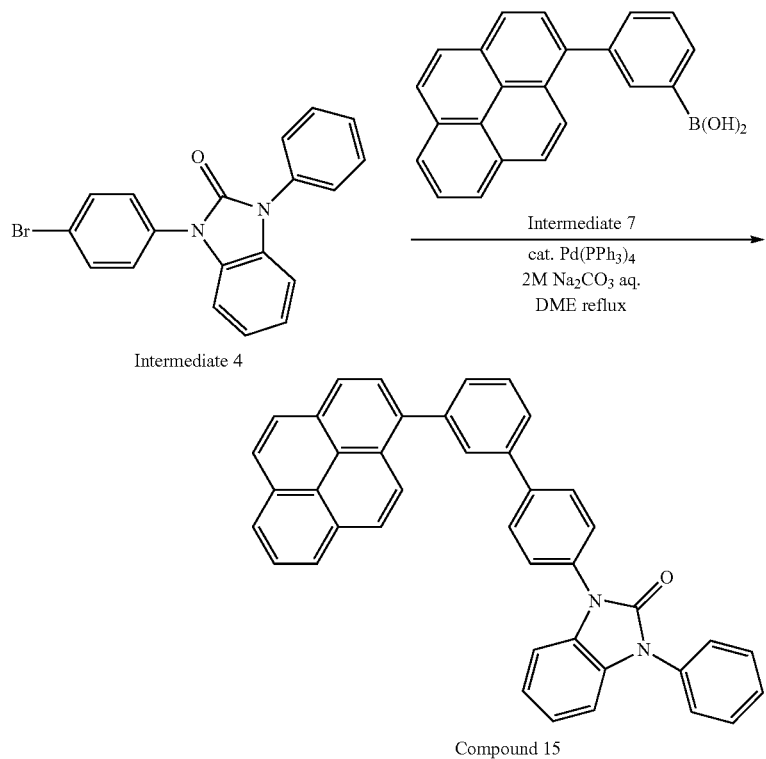

Compound 15

The procedure of Synthesis Example 1 (a-4) was repeated except for using Intermediate 7 in place of Intermediate 5 to obtain a compound (yield: 73%), which was identified as Compound 15 by FD-MS.

Synthesis Example 16

(p) Synthesis of Compound 16

Compound 16 was synthesized according to the following scheme.

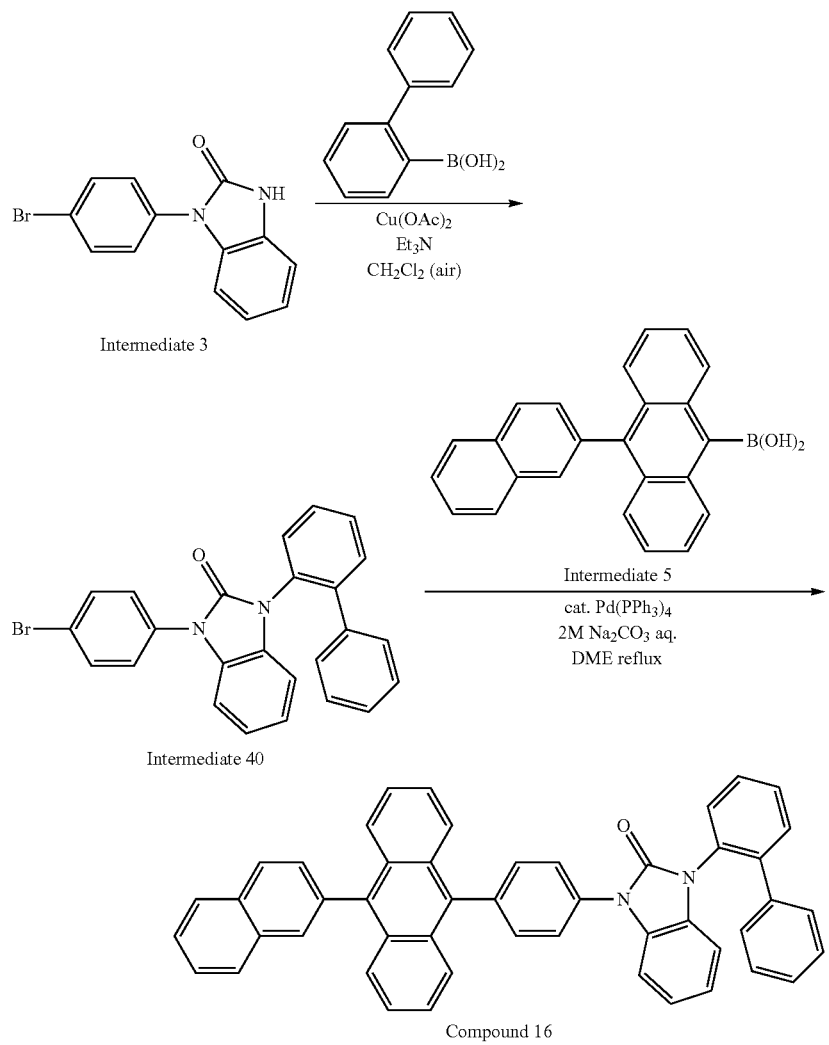

Intermediate 3

Intermediate 40

Compound 16

(p-1) Synthesis of Intermediate 40

The procedure of Synthesis Example 1 (a-3) was repeated except for using 2-biphenylboronic acid in place of phenylboronic acid to obtain Intermediate 40 (yield: 20%).

(p-2) Synthesis of Compound 16

The procedure of Synthesis Example 1 (a-4) was repeated except for using Intermediate 40 in place of Intermediate 4 to obtain a compound (yield: 88%), which was identified as Compound 16 by FD-MS.

Synthesis Example 17

(q) Synthesis of Compound 17

Compound 17 was synthesized according to the following scheme.

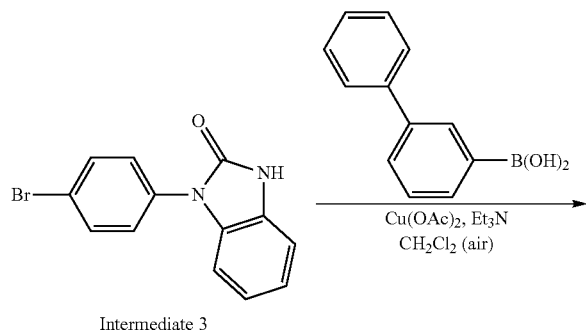

Intermediate 3

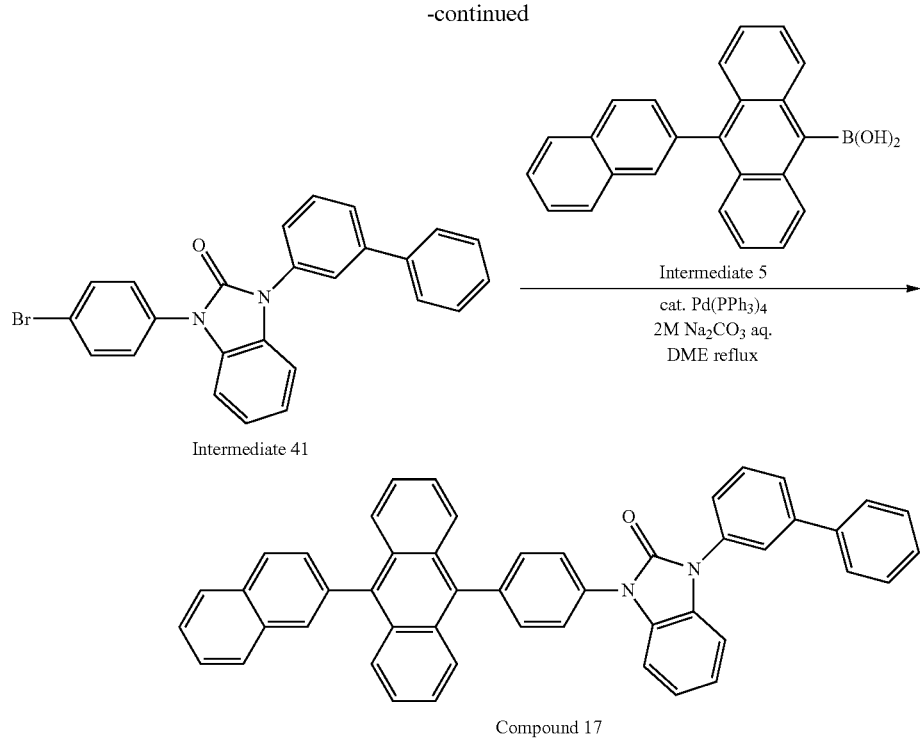

(q-1) Synthesis of Intermediate 41

The procedure of Synthesis Example 1 (q-3) was repeated except for using 3-biphenylboronic acid in place of phenylboronic acid to obtain Intermediate 41 (yield: 73%).

(q-2) Synthesis of Compound 17

The procedure of Synthesis Example 1 (a-4) was repeated except for using Intermediate 41 in place of Intermediate 4 to obtain a compound (yield: 91%), which was identified as Compound 17 by FD-MS.

Synthesis Example 18

(r) Synthesis of Compound 18

Compound 18 was synthesized according to the following scheme.

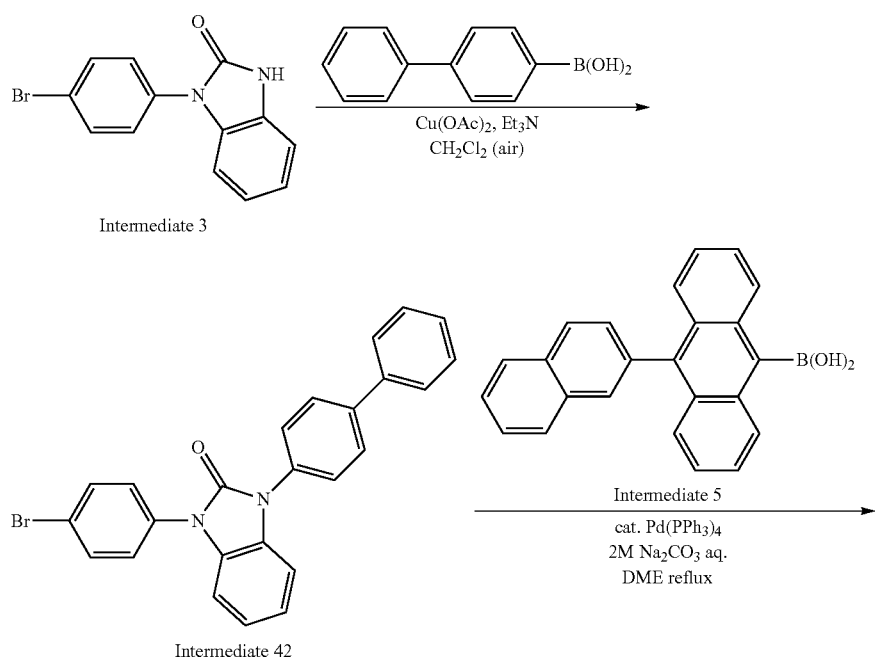

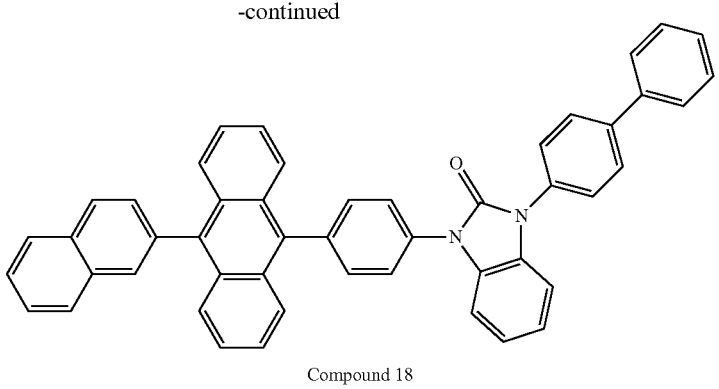

Compound 18

(r-1) Synthesis of Intermediate 42

The procedure of Synthesis Example 1 (a-3) was repeated except for using 4-biphenylboronic acid in place of phenylboronic acid to obtain Intermediate 42 (yield: 60%).

(r-2) Synthesis of Compound 18

The procedure of Synthesis Example 1 (a-4) was repeated except for using Intermediate 42 in place of Intermediate 4 to obtain a compound (yield: 91%), which was identified as Compound 18 by FD-MS.

Synthesis Example 19

(s) Synthesis of Compound 19

Compound 19 was synthesized according to the following scheme.

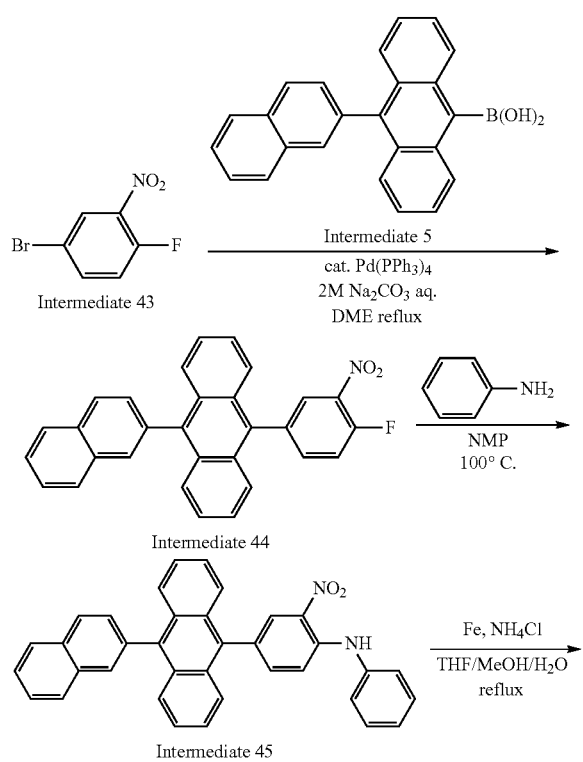

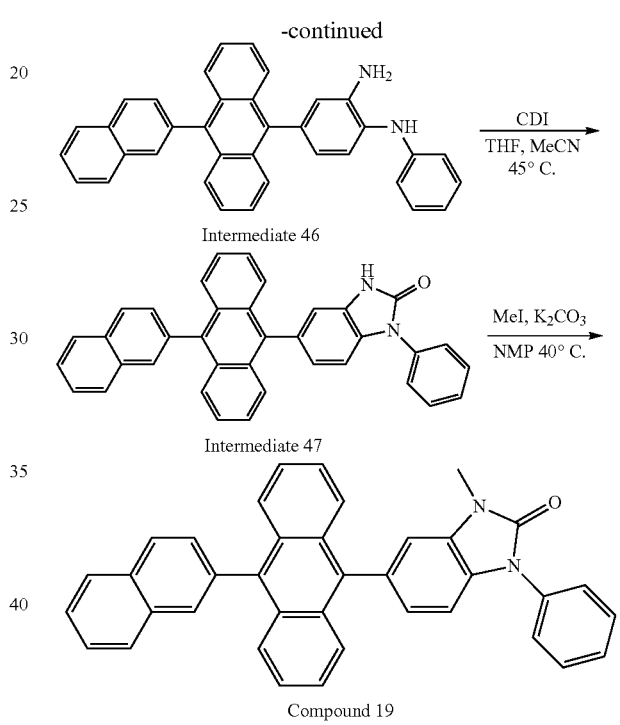

(s-1) Synthesis of Intermediate 44

The procedure of Synthesis Example 1 (a-4) was repeated except for using Intermediate 43 in place of Intermediate 4 to obtain Intermediate 44 (yield: 62%).

(s-2) Synthesis of Intermediate 46

In an argon atmosphere, 1-methyl-2-pyrrolidone (250 mL) was added to Intermediate 44 (29.0 g, 56 mmol) and aniline (17.3 g, 186 mmol). The resultant mixture was stirred at 100° C. for 16 h and then cooled to room temperature. The solid generated by adding water was collected by filtration, washed with water and methanol, and dried under reduced pressure to obtain Intermediate 45 (29.1 g). Then, the procedure of Synthesis Example 3 (c-3) was repeated except for using Intermediate 45 in place of Intermediate 10 to obtain Intermediate 46 (yield: 81%).

(s-3) Synthesis of Intermediate 47

In an argon atmosphere, into a mixture of Intermediate 46 (22.0 g, 35 mmol) and dry THF (200 mL), a solution of 1,1'-carbonyldiimidazole (10.4 g, 69 mmol) in dry acetonitrile (150 mL) was added dropwise at 45° C. over 1.5 h. Successively after the addition, the mixture was stirred at 45° C. for 18 h and then cooled to room temperature. The precipitated solid was collected by filtration, washed with methanol, and dried under reduced pressure to obtain a compound (17.5 g, yield: 76%), which was identified as Intermediate 47 by FD-MS.

(s-4) Synthesis of Compound 19

In an argon atmosphere, a mixture of Intermediate 47 (17.5 g, 34 mmol), potassium carbonate (9.4 g, 68 mmol), iodomethane (9.7 g, 68 mmol), and 1-methyl-2-pyrrolidone (500 mL) was stirred at 40° C. for 18 h and then cooled to room temperature. The mixture was poured into iced water and then extracted with toluene. The organic layer was successively washed with water and a saturated saline solution and dried over magnesium sulfate. The solid obtained by evaporating off the solvent under reduced pressure was washed with heptane and dried under reduced pressure to obtain 14.4 g (yield: 80%) of a pale yellow solid, which was identified as Compound 19 by FD-MS.

Synthesis Example 20

(t) Synthesis of Compound 20

Compound 20 was synthesized according to the following scheme.

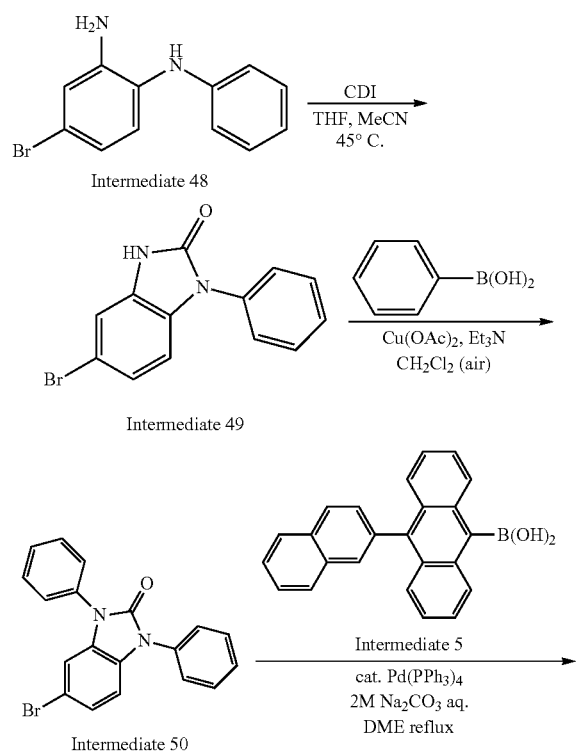

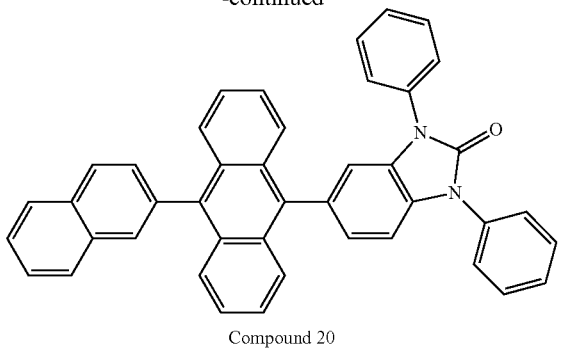

Compound 20

(t-1) Synthesis of Intermediate 49

The procedure of Synthesis Example 19 (s-3) was repeated except for using Intermediate 48 in place of Intermediate 46 to obtain Intermediate 49 (yield: 97%).

(t-2) Synthesis of Intermediate 50

The procedure of Synthesis Example 1 (a-3) was repeated except for using Intermediate 49 in place of Intermediate 3 to obtain Intermediate 50 (yield: 84%).

(t-3) Synthesis of Compound 20

The procedure of Synthesis Example 1 (a-4) was repeated except for using Intermediate 50 in place of Intermediate 4 to obtain a compound (yield: 98%), which was identified as Compound 20 by FD-MS.

Synthesis Example 21

(u) Synthesis of Compound 21

Compound 21 was synthesized according to the following scheme.

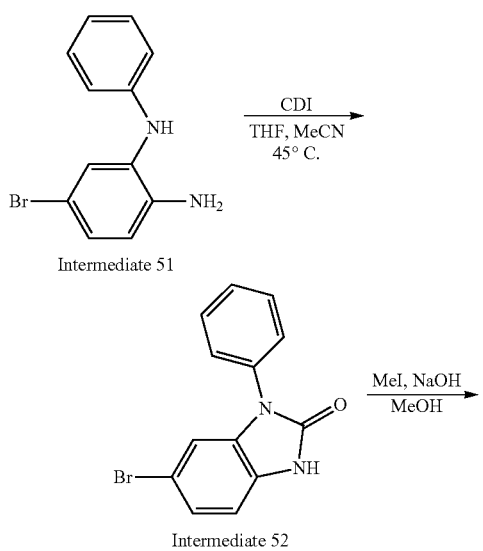

-continued

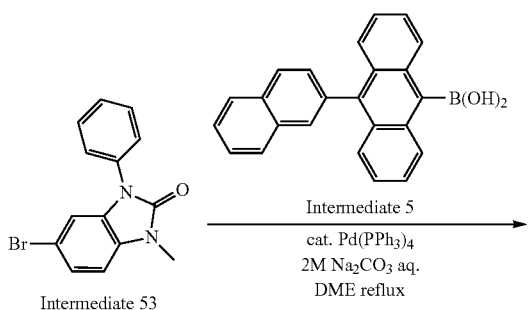

(u-1) Synthesis of Intermediate 52

The procedure of Synthesis Example 19 (s-3) was repeated except for using Intermediate 51 in place of Intermediate 46 to obtain Intermediate 52 (yield: 91%).

(u-2) Synthesis of Intermediate 53

The procedure of Synthesis Example 2 (b-2) was repeated except for using Intermediate 52 in place of Intermediate 3 to obtain Intermediate 53 (yield: 53%).

(u-3) Synthesis of Compound 21

The procedure of Synthesis Example 1 (a-4) was repeated except for using Intermediate 53 in place of Intermediate 4 to obtain a compound (yield: 65%), which was identified as Compound 21 by FD-MS.

Example 1

(1) Production of Organic EL Device

A glass substrate provided with an ITO transparent electrode (anode) having a size of 25 mm×75 mm and a thickness of 0.7 mm (manufactured by Geomatic Inc.) was subjected to ultrasonic cleaning in isopropyl alcohol for 5 min and then subjected to UV ozone cleaning for 30 min.

The cleaned glass substrate provided with transparent electrode lines was installed in a substrate holder of a vacuum vapor deposition apparatus and then a HT-1 film having a thickness of 50 nm was formed so as to cover the transparent electrode lines. The HT-1 film functions as a hole injecting layer. Subsequently, Compound HT-2 was vapor deposited, thereby forming an HT-2 film having a thickness of 45 nm on the HT-1 film. The HT-2 film functions as a hole transporting layer.

Compound BH-1 (host material) and Compound BD-1 (dopant material) were vapor deposited on the HT-2 film in a thickness ratio corresponding to 3% by mass of Compound BD-1, thereby forming an organic layer having a thickness of 20 nm. This organic layer functions as a light emitting layer. On the light emitting layer, Compound 1 was vapor deposited to form an electron transporting layer having a film thickness of 30 nm. Thereafter, LiF was deposited into a thickness of 1 nm. On the LiF film, metallic Al was vapor deposited into a thickness of 80 nm to form a metal cathode, thereby producing an organic EL device.

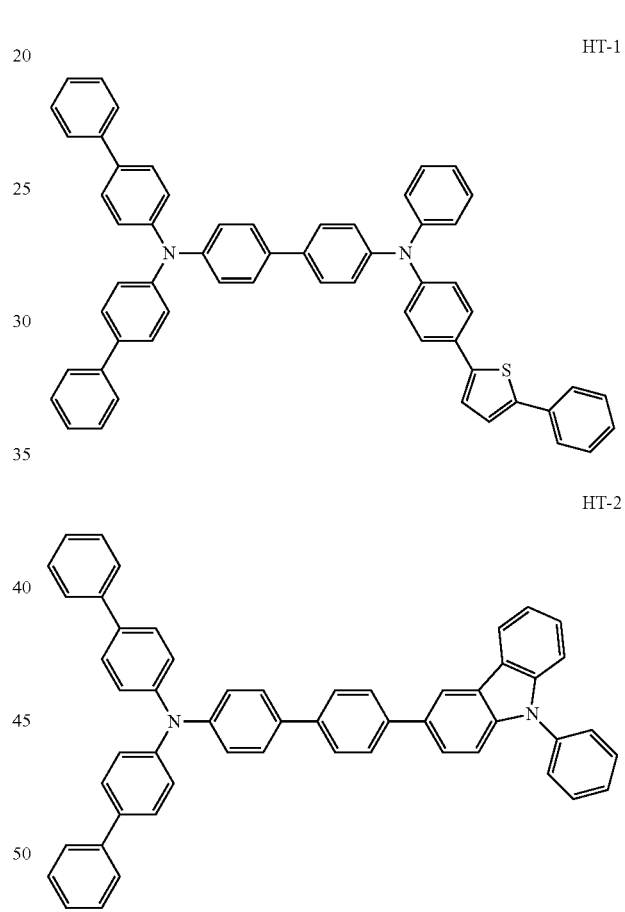

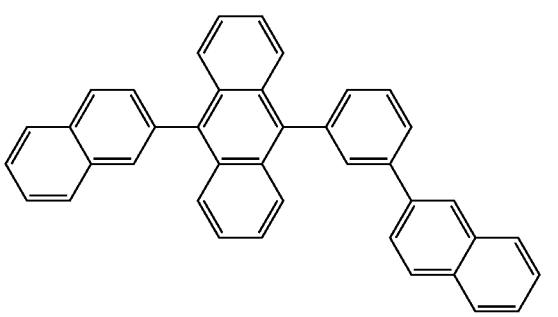

-continued

BD-1

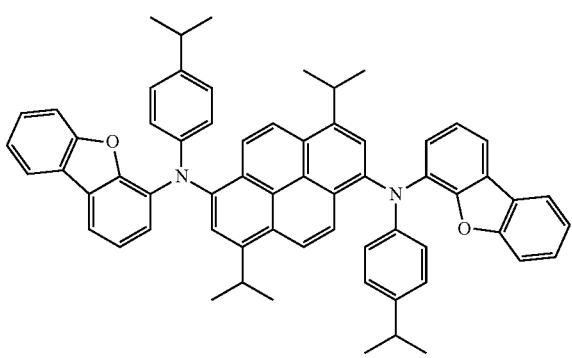

(2) Evaluation of Organic EL Device

The voltage (V) applied to the organic EL device thus produced where the current density was 10 mA/cm² was measured. Simultaneously, EL emission spectrum was measured by using a spectroradiometer (CS-1000 manufactured by Konica Minolta, Inc.). The external quantum efficiency (%) was calculated from the obtained spectral radiance. The results are shown in Table 1.

Examples 2 to 3 and Comparative Examples 1 to 3

Each organic EL device was produced in the same manner as in Example 1 except for forming the electron transporting layer by using Compound 3 (Example 2), Compound 20 (Example 3), Compound ET-1 (Comparative Example 1), Compound ET-2 (Comparative Example 2), and Compound ET-3 (Comparative Example 3) each in place of Compound 1. The results of evaluating the organic EL devices are shown in Table 1.

ET-1

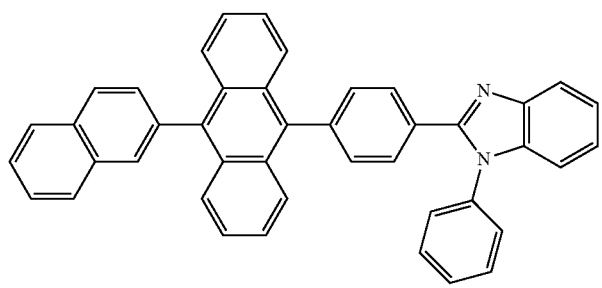

ET-2

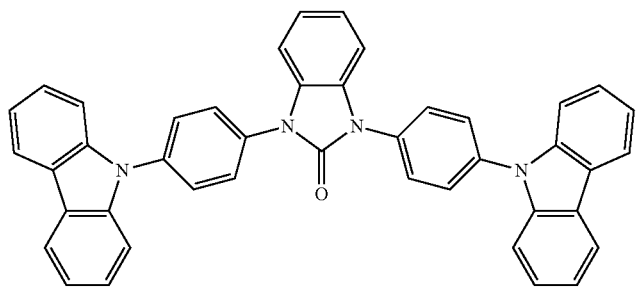

ET-3

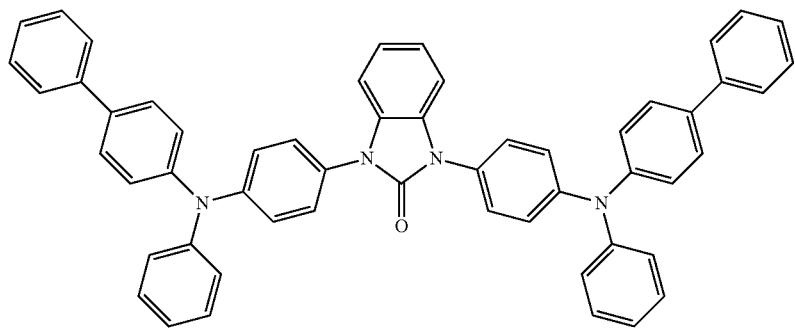

TABLE 1

|  | Electron transporting layer | Driving voltage (V) | External quantum efficiency (%) | Emission color |
|---|---|---|---|---|
| Examples |  |  |  |  |
| 1 | Compound 1 | 3.9 | 7.4 | blue |
| 2 | Compound 3 | 3.7 | 6.5 | blue |
| 3 | Compound 20 | 3.8 | 7.5 | blue |
| Comparative Examples |  |  |  |  |
| 1 | Compound ET-1 | 4.6 | 6.2 | blue |
| 2 | Compound ET-2 | 11.1 | 0.1 | blue |
| 3 | Compound ET-3 | 10.3 | 0.1 | blue |

Example 4

A glass substrate provided with an ITO transparent electrode (anode) having a size of 25 mm×75 mm and a thickness of 0.7 mm (manufactured by Geomatic Inc.) was subjected to ultrasonic cleaning in isopropyl alcohol for 5 min and then subjected to UV ozone cleaning for 30 min.

The cleaned glass substrate provided with transparent electrode lines was installed in a substrate holder of a vacuum vapor deposition apparatus and then an HT-1 film having a thickness of 50 nm was formed so as to cover the transparent electrode lines. The HT-1 film functions as a hole injecting layer. Subsequently, Compound HT-2 was vapor deposited, thereby forming an HT-2 film having a thickness of 45 nm on the HT-1 film. The HT-2 film functions as a hole transporting layer.

Compound BH-1 (host material) and Compound BD-1 (dopant material) were vapor deposited on the HT-2 film in a thickness ratio corresponding to 3% by mass of Compound BD-1, thereby forming a light emitting layer having a thickness of 20 nm. On the light emitting layer, Compound 1 and lithium ($L_1$) were vapor deposited in a thickness ratio corresponding to 2% by mass of $L_1$, thereby forming an electron transporting layer having a thickness of 30 nm. On the electron transporting layer, metallic Al was vapor deposited into a thickness of 80 nm to form a metal cathode, thereby producing an organic EL device.

The results of evaluating the obtained organic EL device in the same manner as in Example 1 are shown in Table 2.

Examples 5 to 12 and Comparative Examples 4 to 6

Each organic EL device was produced in the same manner as in Example 4 except for forming the electron transporting layer by using Compound 12 (Example 5), Compound 13 (Example 6), Compound 14 (Example 7), Compound 17 (Example 8), Compound 18 (Example 9), Compound 19 (Example 10), Compound 20 (Example 11), Compound 21 (Example 12), Compound ET-1 (Comparative Example 4), Compound ET-2 (Comparative Example 5), and Compound ET-3 (Comparative Example 6) each in place of Compound 1. The results of evaluating the organic EL devices are shown in Table 2.

TABLE 2

|  | Electron transporting layer | Driving voltage (V) | External quantum efficiency (%) | Emission color |
|---|---|---|---|---|
| Examples |  |  |  |  |
| 4 | Compound 1 + Li | 3.3 | 5.9 | blue |
| 5 | Compound 12 + Li | 3.5 | 5.9 | blue |
| 6 | Compound 13 + Li | 3.4 | 6.0 | blue |
| 7 | Compound 14 + Li | 3.2 | 5.1 | blue |
| 8 | Compound 17 + Li | 3.5 | 5.7 | blue |
| 9 | Compound 18 + Li | 3.5 | 6.0 | blue |
| 10 | Compound 19 + Li | 3.5 | 5.1 | blue |
| 11 | Compound 20 + Li | 3.2 | 5.1 | blue |
| 12 | Compound 21 + Li | 3.2 | 5.2 | blue |
| Comparative Examples |  |  |  |  |
| 4 | Compound ET-1 + Li | 3.7 | 5.1 | blue |
| 5 | Compound ET-2 + Li | 11.0 | 5.4 | blue |
| 6 | Compound ET-3 + Li | 10.7 | 5.4 | blue |

INDUSTRIAL APPLICABILITY

As described above in detail, by using the nitrogen-containing heterocyclic derivative of the invention in at lease one layer of the organic thin film layer of organic EL devices, a high emission efficiency is achieved even at low voltage and a high emission efficiency is also achieved because the electron transporting ability is excellent. Therefore, the organic EL device of the invention is extremely useful, for example, as light sources of various electronic equipments.

What is claimed is:

1. A nitrogen-comprising heterocyclic derivative of formula (1-1)

$$A_{11}(-L_{11}-L_{21}-L_{31}-L_{41}-Ar_{11})_p \quad (1\text{-}1)$$

wherein:

$L_{11}$, $L_{21}$, $L_{31}$, and $L_{41}$ are each independently a single bond;

$Ar_{11}$ is a substituted or unsubstituted alkyl group having 1 to 50 carbon atoms, a substituted or unsubstituted cycloalkyl group having 3 to 50 ring carbon atoms, a phenyl group, a 1-naphthyl group, a 2-naphthyl group, a 1-anthryl group, a 2-anthryl group, a 9-anthryl group, a 1-naphthacenyl group, a 2-naphthacenyl group, a 9-naphthacenyl group, a 1-pyrenyl group, a 2-pyrenyl group, a 4-pyrenyl group, o-tolyl group, m-tolyl group, p-tolyl group, p-t-butylphenyl group, 3-methyl-2-naphthyl group, 4-methyl-1-naphthyl group, 4-methyl-1-anthryl group, a fluoranthenyl group, a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(2-phenylpropyl)pyrrole-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, or a 4-t-butyl-3-indolyl group;

$A_{11}$ is a p-valent residue of a ring-comprising compound represented by formula (2-1-2-1);

p is an integer of 1 or more;

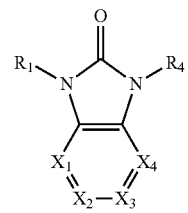

(2-1-2-1)

wherein:

$X_1$, $X_2$, $X_3$, and $X_4$ are each independently $CR_5$ $R_1$ and $R_4$ are each independently a hydrogen atom or a valence bonded to $L_{11}$;

$R_5$ is each independently a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{11}$; or each of $R_5$ is bonded to each other to form a ring that forms a part of a ring Y that is represented by a substituted or unsubstituted hydrocarbon ring or an unsubstituted heteroring.

2. The derivative according to claim 1, wherein the ring Y is selected from the group consisting of a substituted or unsubstituted non-fused aromatic hydrocarbon ring having 6 to 30 ring carbon atoms, a substituted or unsubstituted fused aromatic hydrocarbon ring having 10 to 30 ring carbon atoms, an unsubstituted non-fused heteroring having 5 to 30 ring atoms, and an unsubstituted fused heteroring having 10 to 30 ring atoms.

3. A material for organic electroluminescence devices comprising the aromatic heterocyclic derivative according to claim 1.

4. An organic electroluminescence device comprising a light emitting layer and an electron transporting layer which are disposed between a cathode and an anode, wherein the electron transporting layer comprises the derivative according to claim 1.

5. The electron transporting material according to claim 1, wherein the ring Y represents a substituted or unsubstituted non-fused aromatic hydrocarbon ring having 6 to 30 ring carbon atoms, a substituted or unsubstituted fused aromatic hydrocarbon ring having 10 to 30 ring carbon atoms, an unsubstituted non-fused heteroring having 5 to 30 ring atoms, an unsubstituted fused heteroring having 10 to 30 ring atoms.

6. The device according to claim 4, wherein the electron transporting layer further comprises a reducing dopant.

7. The device according to claim 6, wherein the reducing dopant is a compound comprising at least one metal selected from the group consisting of alkali metal, alkaline earth metal, and rare earth metal.

8. The device according to claim 7, wherein the reducing dopant is at least one selected from the group consisting of alkali metal, alkali metal oxide, alkali metal halide, alkaline earth metal oxide, alkaline earth metal halide, rare earth metal oxide, and rare earth metal halide.

9. The electron transporting material according to claim 1, wherein at least one $R_5$ is a substituted or unsubstituted aryl group having 6 to 30 ring carbon atoms.

10. The electron transporting material according to claim 1, wherein at least one of $R_5$ $R_5'_S$ is a substituted aryl group having 6 to 30 ring carbon atoms.

11. The electron transporting material according to claim 1, wherein at least one $R_5$ is a substituted or unsubstituted 1-anthryl group, a substituted or unsubstituted 2-anthryl group, or a substituted or unsubstituted 9-anthryl group.

12. The electron transporting material according to claim 1, wherein at least one $R_5$ is a substituted 1-anthryl group, a substituted 2-anthryl group, or a substituted 9-anthryl group.

13. The nitrogen-containing heterocyclic derivative according to claim 1, wherein at least one $R_5$ is a substituted or unsubstituted aryl group having 6 to 30 ring carbon atoms.

14. The nitrogen-containing heterocyclic derivative according to claim 1, wherein at least one $R_5$ is a substituted aryl group having 6 to 30 ring carbon atoms.

15. The nitrogen-containing heterocyclic derivative according to claim 1, wherein at least one $R_5$ is a substituted or unsubstituted 1-anthryl group, a substituted or unsubstituted 2-anthryl group, or a substituted or unsubstituted 9-anthryl group.

16. The nitrogen-containing heterocyclic derivative according to claim 1, wherein at least one $R_5$ is a substituted 1-anthryl group, a substituted 2-anthryl group, or a substituted 9-anthryl group.

17. The nitrogen-containing heterocyclic derivative according to claim 1, wherein $Ar_{11}$ is an unsubstituted aryl group having 6 to 30 ring carbon atoms, or an unsubstituted heteroaryl group having 5 to 30 ring atoms;

wherein the unsubstituted aryl group having 6 to 30 ring carbon atoms is selected from the group consisting of a phenyl group, a 1-naphthyl group, a 2-naphthyl group, a 1-anthryl group, a 2-anthryl group, a 9-anthryl group, naphthacenyl group, a 2-naphthacenyl group, a 9-naphthacenyl group, a 1-pyrenyl group, a 2-pyrenyl group, a 4-pyrenyl group, and a fluoranthenyl group; and the unsubstituted heteroaryl group having 5 to 30 ring atoms is a group selected from the group consisting of a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6- yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, and a 3-thienyl group.

18. The nitrogen-containing heterocyclic derivative according to claim 1, wherein $Ar_{11}$ is an unsubstituted alkyl group having 1 to 50 carbon atoms, or an unsubstituted aryl group having 6 to 30 ring carbon atoms.

19. The nitrogen-containing heterocyclic derivative according to claim 1, wherein $Ar_{11}$ is an unsubstituted alkyl group having 1 to 50 carbon atoms, an unsubstituted phenyl group, an unsubstituted 1-naphthyl group, or an unsubstituted 2-naphthyl group.

20. The nitrogen-containing heterocyclic derivative according to claim 1, wherein $Ar_{11}$ is an unsubstituted alkyl group having 1 to 50 carbon atoms, or an unsubstituted phenyl group.

21. The nitrogen-containing heterocyclic derivative according to claim 1, wherein $R_5$ is each independently a hydrogen atom, an unsubstituted alkyl group having 1 to 50 carbon atoms, or a substituted or unsubstituted aryl group having 6 to 30 ring carbon atoms.

22. The nitrogen-containing heterocyclic derivative according to claim 1, wherein $Ar_{11}$ is an unsubstituted alkyl group having 1 to 50 carbon atoms, or an unsubstituted phenyl group,
and $R_5$ is each independently a hydrogen atom, an unsubstituted alkyl group having 1 to 50 carbon atoms, or a substituted or unsubstituted aryl group having 6 to 30 ring carbon atoms.

23. A nitrogen-containing heterocyclic derivative of formula (1-1):

wherein:
$L_{11}$, $L_{21}$, $L_{31}$, and $L_{41}$ are each independently a single bond, a substituted or unsubstituted alkylene group having 1 to 50 carbon atoms, a substituted or unsubstituted alkenylene group having 1 to 50 carbon atoms, a substituted or unsubstituted alkynylene group having 1 to 50 carbon atoms, a substituted or unsubstituted cycloalkylene group having 3 to 50 ring carbon atoms, a substituted or unsubstituted arylene group having 6 to 30 ring carbon atoms, or a substituted or unsubstituted heteroarylene group having 5 to 30 ring atoms;
$Ar_{11}$ is a substituted or unsubstituted anthracene, or a substituted or unsubstituted pyrene;
$A_{11}$ is a p-valent residue of a ring-containing compound represented by formula (2-1-2-1); and
p is an integer of 1 or more:

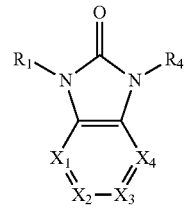

wherein:
$X_1$, $X_2$, $X_3$, and $X_4$ are each independently represents $CR_5$;
$R_1$, $R_4$, and $R_5$ are each independently a hydrogen atom, a substituted or unsubstituted alkyl group having 1 to 50 carbon atoms, a substituted or unsubstituted alkoxy group having 1 to 50 carbon atoms, a substituted or unsubstituted alkoxycarbonyl group having 1 to 50 carbon atoms, a substituted or unsubstituted cycloalkyl group having 3 to 50 ring carbon atoms, a substituted or unsubstituted aryl group having 6 to 30 ring carbon atoms, a substituted or unsubstituted aralkyl group having 6 to 50 ring carbon atoms, a substituted or unsubstituted aryloxy group having 6 to 50 ring carbon atoms, a substituted or unsubstituted heteroaryl group having 5 to 30 ring atoms, a substituted or unsubstituted alkylsilyl group having 1 to 50 carbon atoms, a substituted or unsubstituted arylsilyl group having 6 to 50 ring carbon atoms, a substituted or unsubstituted haloalkyl group having 1 to 50 carbon atoms, a substituted or unsubstituted alkenyl group having 1 to 50 carbon atoms, a substituted or unsubstituted alkynyl group having 1 to 50 carbon atoms, a substituted or unsubstituted alkylamino group having 1 to 50 carbon atoms, a substituted or unsubstituted arylamino group having 6 to 30 ring carbon atoms, a substituted or unsubstituted heteroarylamino group having 5 to 30 ring atoms, a substituted or unsubstituted acylamino group having 2 to 50 carbon atoms, a substituted or unsubstituted heteroaryloxy group having 5 to 30 ring atoms, a substituted or unsubstituted acyl group having 2 to 50 carbon atoms, a substituted or unsubstituted aryloxycarbonyl group having 6 to 30 ring carbon atoms, a substituted or unsubstituted alkylcarbonyl group having 1 to 50 carbon atoms, a mercapto group, a substituted or unsubstituted alkylthio group having 1 to 50 carbon atoms, a substituted or unsubstituted arylthio group having 6 to 30 ring carbon atoms, a sulfonyl group, an boryl group, a phosphino group, an amino group, a halogen atom, a cyano group, a nitro group, a hydroxyl group, a carboxyl group, or a valence bonded to $L_{11}$.

24. The nitrogen-containing heterocyclic derivative according to claim 23, wherein $L_3$, and $L_{41}$ are a single bond, and $L_{21}$ and $L_{11}$ are a single bond or the unsubstituted arylene group having 6 to 30 ring carbon atoms.

25. The nitrogen-containing heterocyclic derivative according to claim 23, wherein when $Ar_{11}$ has a substituent, the substituent represents an unsubstituted alkyl group having 1 to 50 carbon atoms or an unsubstituted aryl group having 6 to 30 ring carbon atoms.

26. The nitrogen-containing heterocyclic derivative according to claim 23, wherein $R_1$, $R_4$, and $R_5$ are each independently an unsubstituted alkyl group having 1 to 50 carbon atoms, or an unsubstituted aryl group having 6 to 30 ring carbon atoms.

27. The nitrogen-containing heterocyclic derivative according to claim 23, wherein $R_1$, $R_4$, and $R_5$ are each independently an unsubstituted alkyl group having 1 to 50 carbon atoms, an unsubstituted phenyl group, an unsubstituted 1-naphthyl group, or an unsubstituted 2-naphthyl group.

28. The nitrogen-containing heterocyclic derivative according to claim 23, wherein $R_1$, $R_4$, and $R_5$ are each independently an unsubstituted alkyl group having 1 to 50 carbon atoms, or an unsubstituted phenyl group.

29. The nitrogen-containing heterocyclic derivative according to claim 23, wherein $L_{31}$ and $L_{41}$ are a single bond, and $L_{21}$ and $L_{11}$ are a single bond or the unsubstituted arylene group having 6 to 30 ring carbon atoms, and when $Ar_{11}$ have a substituent, the substituent represents an unsubstituted alkyl group having 1 to 50 carbon atoms or an unsubstituted aryl group having 6 to 30 ring carbon atoms, and $R_1$, $R_4$, and $R_5$ are each independently an unsubstituted alkyl group having 1 to 50 carbon atoms, or an unsubstituted phenyl group.

30. An organic electroluminescence device comprising a light emitting layer and an electron transporting layer which are disposed between a cathode and an anode, wherein the electron transporting layer comprises the nitrogen-containing heterocyclic derivative according to claim 23.

31. The organic electroluminescence device according to claim 30, wherein the electron transporting layer further comprises a reducing dopant.

32. The organic electroluminescence device according to claim 31, wherein the reducing dopant is a compound comprising at least one metal selected from the group consisting of alkali metals, alkaline earth metals, and rare earth metals.

33. The organic electroluminescence device according to claim 32, wherein the reducing dopant is at least one selected from the group consisting of alkali metals, alkali metal oxides, alkali metal halides, alkaline earth metal oxides, alkaline earth metal halides, rare earth metal oxides, and rare earth metal halides.

* * * * *